US009701789B2

(12) United States Patent
Chen et al.

(10) Patent No.: US 9,701,789 B2
(45) Date of Patent: Jul. 11, 2017

(54) SULFONIC ACID GROUP-CONTAINING POLYMER, SULFONIC ACID GROUP-CONTAINING AROMATIC COMPOUND AND METHOD OF MAKING THE SAME, AS WELL AS POLYMER ELECTROLYTE MATERIAL, POLYMER ELECTROLYTE MOLDED PRODUCT AND SOLID POLYMER FUEL CELL USING THE SAME

(75) Inventors: Qiao Chen, Shanghai (CN); Fangke Shao, Shanghai (CN); Gang Wu, Shanghai (CN); Daisuke Izuhara, Shiga (JP); Hiroaki Umeda, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 70 days.

(21) Appl. No.: 14/346,288

(22) PCT Filed: Sep. 6, 2012

(86) PCT No.: PCT/CN2012/081062
§ 371 (c)(1),
(2), (4) Date: Oct. 14, 2014

(87) PCT Pub. No.: WO2013/040985
PCT Pub. Date: Mar. 28, 2013

(65) Prior Publication Data
US 2015/0094446 A1    Apr. 2, 2015

(30) Foreign Application Priority Data

Sep. 20, 2011  (JP) ................................ 2011-204253
Sep. 21, 2011  (WO) ............... PCT/CN2011/079958

(51) Int. Cl.
| | | |
|---|---|---|
| C08G 65/40 | (2006.01) | |
| C08G 65/00 | (2006.01) | |
| C07C 309/44 | (2006.01) | |
| H01B 1/12 | (2006.01) | |
| H01M 8/1023 | (2016.01) | |
| H01M 8/1025 | (2016.01) | |
| H01M 8/1032 | (2016.01) | |
| H01M 8/1034 | (2016.01) | |
| C07C 309/00 | (2006.01) | |
| C07C 317/14 | (2006.01) | |
| H01M 8/1018 | (2016.01) | |

(52) U.S. Cl.
CPC ............ *C08G 65/00* (2013.01); *C07C 309/00* (2013.01); *C07C 309/44* (2013.01); *C07C 317/14* (2013.01); *C08G 65/4043* (2013.01); *C08G 65/4056* (2013.01); *H01B 1/122* (2013.01); *H01M 8/1023* (2013.01); *H01M 8/1025* (2013.01); *H01M 8/1032* (2013.01); *H01M 8/1034* (2013.01); *H01M 2008/1095* (2013.01); *H01M 2300/0082* (2013.01); *Y02P 70/56* (2015.11)

(58) Field of Classification Search
CPC ....................... C08G 65/4006; C08G 65/4056
See application file for complete search history.

(56) References Cited

U.S. PATENT DOCUMENTS 5,362,836 A * 11/1994 Helmer-
                      Metzmann ............. B01D 71/52
                                              525/328.5
9,126,908 B2 * 9/2015 Izuhara ................... C08G 65/40
2001/0021764 A1 * 9/2001 Weisse ................... B01D 71/80
                                                   528/171

(Continued)

FOREIGN PATENT DOCUMENTS

| CN | 101218281 | 7/2008 |
|---|---|---|
| CN | 101463129 | 6/2009 |
| CN | 101485022 | 7/2009 |
| EP | 2338924 | 6/2011 |
| JP | 2005-126684 | 5/2005 |
| JP | 2006-70126 | 3/2006 |
| JP | 2006-310159 | 11/2006 |

(Continued)

OTHER PUBLICATIONS

Machine translation of JP 2007-84739, 2015.*
English translation of Japanese Office Action dated Jun. 5, 2015 in corresponding Japanese Patent Application No. 2011-204253(3 pages).
Extended European Search Report, dated Apr. 17, 2015.

*Primary Examiner* — Liam J Heincer
(74) *Attorney, Agent, or Firm* — Pillsbury Winthrop Shaw Pittman LLP

(57) ABSTRACT

It is an object of the present invention to provide a sulfonic acid group-containing polymer and a sulfonic acid group-containing aromatic compound, which have excellent proton conductivity even under the low humidification condition, are excellent in mechanical strength and chemical stability and, moreover, can attain high output and excellent physical durability when processed into a solid polymer fuel cell, as well as a polymer electrolyte material, a polymer electrolyte molded product and a solid polymer fuel cell respectively using the same. The sulfonic acid group-containing polymer of the present invention is a sulfonic acid group-containing polymer comprising a constituent unit containing a sulfonic acid group (A1), and a constituent unit not containing a sulfonic acid group (A2), wherein the polymer contains a constituent unit having a specified structure as at least one constituent unit containing a sulfonic acid group (A1) at 25 mol % or more based on a sum of the constituent unit containing a sulfonic acid group (A1). Further, the polymer electrolyte material, polymer electrolyte molded product and solid polymer fuel cell of the present invention are constituted using such a sulfonic acid group-containing polymer.

15 Claims, 3 Drawing Sheets

(56) References Cited

U.S. PATENT DOCUMENTS

| | | | |
|---|---|---|---|
| 2007/0142614 A1* | 6/2007 | Hung | C08G 75/23 528/220 |
| 2007/0292731 A1 | 12/2007 | Goa et al. | |
| 2008/0145669 A1* | 6/2008 | Ye | C08F 226/02 428/419 |
| 2009/0208806 A1* | 8/2009 | Izuhara | C08G 65/4056 429/450 |
| 2009/0233146 A1* | 9/2009 | Lee | C08G 65/4006 429/493 |
| 2010/0196782 A1* | 8/2010 | Izuhara | C08G 65/4012 429/483 |
| 2012/0164558 A1* | 6/2012 | Hida | C07C 309/73 429/494 |
| 2014/0193742 A1* | 7/2014 | Izuhara | H01M 8/1025 429/492 |
| 2014/0213671 A1* | 7/2014 | Izuhara | C08G 65/40 521/25 |
| 2014/0322628 A1* | 10/2014 | Umeda | C08G 81/00 429/492 |

FOREIGN PATENT DOCUMENTS

| | | |
|---|---|---|
| JP | 2007-84739 | 4/2007 |
| JP | 2009-185250 | 8/2009 |
| WO | 2007/064809 | 6/2007 |
| WO | WO2011016444 | 2/2011 |
| WO | 2011/030921 | 3/2011 |

* cited by examiner

SULFONIC ACID GROUP-CONTAINING POLYMER, SULFONIC ACID GROUP-CONTAINING AROMATIC COMPOUND AND METHOD OF MAKING THE SAME, AS WELL AS POLYMER ELECTROLYTE MATERIAL, POLYMER ELECTROLYTE MOLDED PRODUCT AND SOLID POLYMER FUEL CELL USING THE SAME

CROSS REFERENCE TO RELATED APPLICATIONS

This application is a national stage entry of International Application No. PCT/CN2012/081062 filed on Sep. 6, 2012 which claims priority to Japanese Patent Application No. 2011-204253 filed on Sep. 20, 2011 and International Application No. PCT/CN2011/079958, the entire contents of which are herein incorporated by reference.

TECHNICAL FIELD

The present invention relates to a sulfonic acid group-containing polymer, a sulfonic acid group-containing aromatic compound and a method of making the same, inter alia, a polymer electrolyte material excellent in practicability, which has excellent proton conductivity even under the low humidification condition, and can attain excellent mechanical strength, chemical stability and physical durability, as well as a polymer electrolyte molded product and a solid polymer fuel cell each using the same.

BACKGROUND ART

A fuel cell is one kind of electrical generators which take out electric energy by electrochemically oxidizing a fuel such as hydrogen or methanol, and has been paid attention as a clean energy supply source, in recent years. Inter alia, since a solid polymer fuel cell has a low standard working temperature of around 100° C., and has high energy density, wide application as an electrical generator for a dispersion-type electric power generation facility at a relatively small scale or a movable body such as an automobile or a ship is expected. The fuel cell is also paid attention as an electric supply for a small movable equipment or a portable equipment, and installation into a portable telephone, a personal computer or the like, in place of secondary cells such as nickel metal hydride and a lithium ion cell, is expected.

In the fuel cell, usually, anode and cathode electrodes in which a reaction bearing electric power generation occurs, and a polymer electrolyte membrane which is to be a proton conductor between the anode and the cathode constitute a membrane electrode assembly (hereinafter, abbreviated as MEA in some cases), and the fuel cell is constituted of, as a unit, a cell in which this MEA is sandwiched by separators. The polymer electrode membrane is mainly constituted of a polymer electrolyte material. The polymer electrolyte material is also used in a binder of an electrode catalyst layer or the like. Examples of the required property of the polymer electrolyte membrane include firstly high proton conductivity, and it is necessary that the polymer electrolyte membrane has high proton conductivity particularly even under high temperature and the low humidification condition. Since the polymer electrolyte membrane bears a function as a barrier which prevents a direct reaction between a fuel and oxygen, the membrane is required to have low permeability of the fuel. In addition, examples of the required properties include chemical stability for enduring a strong oxidative atmosphere during fuel cell operation, mechanical strength and physical durability which can endure membrane thinning and repeating of swelling and drying, and the like.

Previously, in the polymer electrolyte membrane, Nafion (registered trademark) (manufactured by Du Pont) which is a perfluorosulfonic acid polymer has been widely used. Since Nafion (registered trademark) is made via multistage synthesis, there are problems that Nafion is very expensive, and has great fuel crossover. In addition, a problem that mechanical strength and physical durability of a membrane are lost due to swelling and drying, a problem that a softening point is low, and use at a high temperature is not possible and, further, a problem of disposal after use, and a problem that recycle of the material is difficult have been pointed out.

Under such circumstances, development of a hydrocarbon electrolyte membrane as a polymer electrolyte material, which can replace Nafion (registered trademark), is inexpensive and is excellent in membrane properties, has been activated in recent years.

For example, a block copolymer having a hydrophobic segment in which a sulfonic acid group has not been substantially introduced, and a hydrophilic segment in which a sulfonic acid group has been introduced, the hydrophobic segment containing polyether sulfone (PES) or polyether ketone, and the hydrophilic segment containing sulfonated polyether sulfone or sulfonated polyether ketone, has been proposed (Patent Documents 1 and 2). In the documents, as the hydrophilic segment, a constituent unit in which a sulfonic acid group has been introduced into 50% of all phenyl groups, that is, an alternate copolymer of aromatic dihalide in which two sulfonic acid groups have been introduced into two phenyl groups, and bisphenol in which a sulfonic acid group has not been introduced into two phenyl groups is used. Usually, since these PESs and polyether ketones are synthesized using an aromatic nucleophilic substitution reaction of electron withdrawing aromatic dihalide and electron donating bisphenol, introduction of an electron withdrawing sulfonic acid group is limited to an aromatic dihalide side, and it is known that it is difficult to introduce a sulfonic acid group into more than 50% of all phenyl groups. Therefore, the present inventors have considered that, in the prior art, there is limitation in further local densification of a sulfonic acid group in a hydrophilic domain, and improvement in proton conductivity under the low humidification condition.

In Patent Document 3, there is described a trial of synthesizing a mixture comprising a disulfonated product, trisulfonated product and tetrasulfonated product of 4,4'-difluorobenzophenone at 50, 30 and 20 mol %, respectively, and copolymerizing the mixture with a fluorene bisphenol. However, since a content mole ratio of the tetrasulfonated product contained in the constituent unit containing a sulfonic acid group is 20 mol %, there is limitation in improvement in low humidification proton conductivity. In the document, as far as the tetrasulfonated product is not selectively synthesized, and usually, these disulfonated product, trisulfonated product and tetrasulfonated product have similar polarity, it is difficult to separate and purify them even using chromatography or the like and, further, it is not possible to enhance a content mole ratio of the tetrasulfonated product.

In Non-Patent Document 1, there is described regarding a block copolymer containing polyether sulfone (PES) as a hydrophobic segment, and sulfonated polyether sulfone in which a sulfonic acid group has been introduced into 100% of all phenyl groups as a hydrophilic segment. The present inventors have confirmed that, in the document, after a polymer similar to that of Patent Document 1 is obtained, a sulfonic acid group is introduced into a phenyl group having high electron density adjacent to an ether group, and thus desulfonation due to a reverse reaction easily proceeds. Further, the present inventors have considered that there is a problem that chemical stability is insufficient, moreover, a post-sulfonation reaction and re-precipitation are necessary, and the number of steps is increased, and thus the cost becomes high.

Like this, the polymer electrolyte material obtained by the prior art is insufficient as a means for improving economical property, processability, proton conductivity, mechanical strength, chemical stability and physical durability, and can not be an industrially useful polymer electrolyte material.

PRIOR ART DOCUMENTS

Patent Documents

Patent Document 1: Japanese Patent Laid-open Publication No. 2009-235158

Patent Document 2: WO 08/018487

Patent Literature 3: Japanese Patent Laid-open Publication No. 2007-84739

Non-Patent Document

Non-Patent Document 1: Journal of Polymer Science A Polymer Chemistry, 48, 2757, 2010.

SUMMARY OF THE INVENTION

Problems to be Solved by the Invention

In view of such background of the prior art, it is an object of the present invention to provide a sulfonic acid group-containing polymer and a sulfonic acid group-containing aromatic compound, which have excellent proton conductivity even under the low humidification condition, are excellent in mechanical strength and chemical stability and, moreover, can attain high output and excellent physical durability when processed into a solid polymer fuel cell, as well as a polymer electrolyte material, a polymer electrolyte molded product and a solid polymer fuel cell respectively using the same.

Solutions to the Problems

In order to solve such problems, the present invention adopts the following means. That is, the sulfonic acid group-containing polymer of the present invention is a sulfonic acid group-containing polymer comprising a constituent unit containing a sulfonic acid group (A1), and a constituent unit not containing a sulfonic acid group (A2), wherein the constituent unit containing a sulfonic acid group (A1) contains one or more identical or different constituent units having the following formula (S1) at 25 mol % or more based on the total molar amount thereof

[Chemical Formula 1]

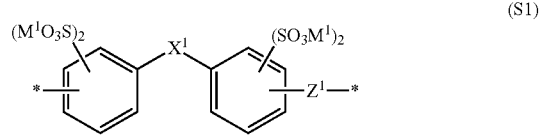

(S1)

In the constituent units having formula (S1), each $X^1$ is independently one of a ketone group, a sulfone group, a direct linkage, —PO($R^1$)— (where $R^1$ is an organic group), —($CF_2$)$_f$— (where f is an integer from 1 to 5) or —C($CF_3$)$_2$—; and each $Z^1$ is independently O or S; each $M^1$ is independently hydrogen, a metal cation, an ammonium cation or a hydrocarbon group having 1 to 20 carbon atoms; * is a bonding site with a moiety having the formula (S1) or other constituent units.

The sulfonic acid group-containing aromatic compound of the present invention has the following formula (M1), and is characterized in that a content of an aromatic compound having the following formula (M2) is 5% by weight or less. Further, the polymer electrolyte material, polymer electrolyte molded product and solid polymer fuel cell of the present invention are characterized in that they are constituted by using such a block polymer.

[Chemical Formula 2]

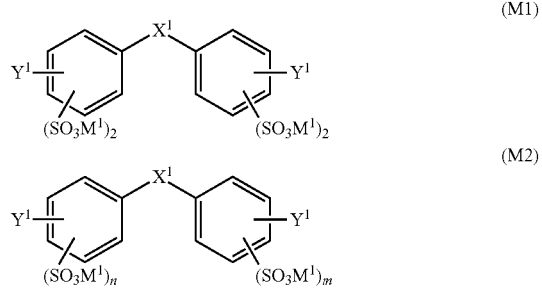

(M1)

(M2)

In the formulas (M1) and (M2), each $X^1$ is independently one of a ketone group, a sulfone group, a direct linkage, —PO($R^1$)— (where $R^1$ is an organic group), —($CF_2$)$_f$— (where f is an integer from 1 to 5) or —C($CF_3$)$_2$—; and each $Y^1$ is independently at least one of F, Cl, Br, and I; each $M^1$ is independently hydrogen, a metal cation, an ammonium cation or a hydrocarbon group having 1 to 20 carbon atoms; m is 0 or 1; n is 0 or 1.

Effects of the Invention

According to the present invention, a sulfonic acid group-containing polymer and a sulfonic acid group-containing aromatic compound which have excellent proton conductivity even under the low humidification condition, are excellent in mechanical strength and chemical stability and, moreover, can attain high output and excellent physical durability when processed into a solid polymer fuel cell, and a method of making the same, as well as a polymer electrolyte material, a polymer electrolyte molded product and a solid polymer fuel cell respectively using the same can be provided.

MODE FOR CARRYING OUT THE INVENTION

Figure 1:
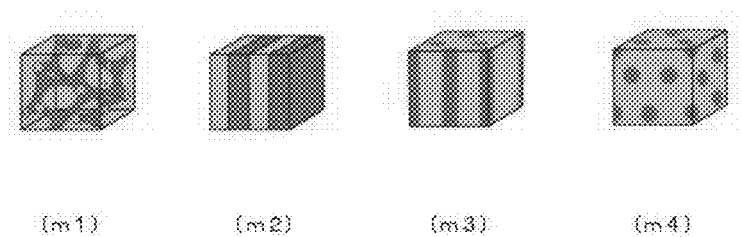
FIG. 1 shows an aspect of a phase-separated structure.

The present invention will be described in more detail below.

In order to overcome the aforementioned problems, the present inventors have studied intensively and, as a result, found out that, by using a specified constituent unit in which four sulfonic acid groups have been introduced into two benzene rings, a sulfonic acid group-containing polymer and a sulfonic acid group-containing aromatic compound which can locally enhance sulfonic acid group density to form a proton conducting channel can exert excellent performance in proton conductivity under the low humidification condition and electric power generation property, processability such as membrane making property, chemical stability such as oxidation resistance, radical resistance or hydrolysis resistance, mechanical strength of a membrane, and physical durability such as hot water resistance as a polymer electrolyte material, particularly, as an electrolyte membrane for a fuel cell, and such problems can be solved at once and, at the same time, further studied variously, resulting in completion of the present invention.

That is, the sulfonic acid group-containing polymer of the present invention is a sulfonic acid group-containing polymer comprising a constituent unit containing a sulfonic acid group (A1), and a constituent unit not containing a sulfonic acid group (A2), wherein the constituent unit containing a sulfonic acid group (A1) contains one or more identical or different constituent units having the following formula (S1) at 25 mol % or more based on the total molar amount thereof

[Chemical Formula 3]

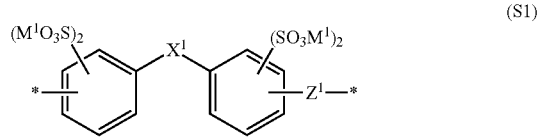

(S1)

In the constituent units having formula (S1), each $X^1$ is independently one of a ketone group, a sulfone group, a direct linkage, —PO($R^1$)— (where $R^1$ is an organic group), —($CF_2$)$_f$— (where f is an integer from 1 to 5) or —C($CF_3$)$_2$—; and each $Z^1$ is independently O or S; each $M^1$ is independently hydrogen, a metal cation, an ammonium cation or a hydrocarbon group having 1 to 20 carbon atoms. * is a bonding site with a moiety having the formula (S1) or other constituent units.

In the present invention, the constituent unit is defined as a constituent unit in which a main chain is partitioned with $Z^1$ (O or S), like the constituent unit having the formula (S1).

The sulfonic acid group-containing polymer of the present invention includes a constituent unit containing a sulfonic acid group (A1), and a constituent unit not containing a sulfonic acid group (A2). The sulfonic acid group-containing polymer of the present invention may have a plurality of different constituent units containing a sulfonic acid group (A1). The polymer may have a plurality of different constituent units not containing a sulfonic acid group (A2).

The sulfonic acid group-containing polymer of the present invention can form a proton conducting channel and enhance low humidification proton conductivity by containing the constituent unit having the formula (S1) as a constituent unit containing a sulfonic acid group (A1) at 25 mol % or more based on the total molar amount of the constituent units containing a sulfonic acid group (A1), that is, enhancing sulfonic acid group density more than the previous constituent unit containing two sulfonic acid groups.

A mole ratio (%) of the constituent units having the formula (S1) based on the molar amount of the constituent units containing a sulfonic acid group (A1) is preferably greater from the view of low humidification proton conductivity, and needs to be 25 mol % or more, and is more preferably 50 mol % or more, further preferably 75 mol %, and most preferably 95% or more. When the mole ratio of the constituent units having the formula (S1) is less than 25 mol %, low humidification proton conductivity is deficient in some cases, and this is not preferable.

In the present invention, examples of $M^1$ include any metal cation, an ammonium cation $NR^{4+}$ (R is an organic group) and the like. In the case of the metal cation, the metal cation can be used without particular limitation of a valence thereof and the like. Specific examples of a preferable metal ion include Li, Na, K, Cs, Rh, Mg, Ca, Sr, Ti, Al, Fe, Pt, Rh, Ru, Ir, Pd and the like. Among them, Na, K, Cs and Li which are inexpensive, and can easily replace proton are more preferably used in the sulfonic acid group-containing polymer of the present invention. A preferable example of R is an alkyl group having 1 to 10 carbon atoms.

In the present invention, $X^1$ is more preferably a ketone group (—CO—), a sulfone group (—$SO_2$—), or a direct linkage from the view of chemical stability and cost, further preferably a ketone group, or a sulfone group, and most preferably a ketone group from the view of physical durability. $Z^1$ is O or S from the view of cost and physical durability, and most preferably O. That is, it is most preferable that $X^1$ is a ketone group, and $Z^1$ is O.

Since the constituent unit having the formula (S1), due to the effects of an electron withdrawing $X^1$ group and a sulfonic acid group, is excellent in chemical stability, and has high dissociability of a proton and, moreover, can locally enhance sulfonic acid group density when processed into a sulfonic acid group-containing polymer, particularly into a block copolymer, a proton conductive channel is formed, and excellent proton conductivity can be realized even under the low humidification condition.

Preferably specific examples of the constituent unit having the formula (S1) include constituent units having the following formulas (S1-1) to (S1-114). The present invention is not limited thereto. Among them, from the view of production cost and physical durability, constituent units having the following formulas (S1-1), (S1-2), (S1-5), and (S1-9) to (S1-11) are more preferable, constituent units having the following formulas (S1-1), (S1-2) and (S1-5) are further preferable, and a constituent unit having the following formula (S1-1) is most preferable. In the present invention, it is also preferable to use a plurality of these constituent units. A position of a sulfonic acid group is further changed in some cases, depending on a kind of a sulfonating agent and a substituent of a raw material compound, and a constituent unit having a different introduction position of a sulfonic acid group is also preferably used.

[Chemical Formula 4]

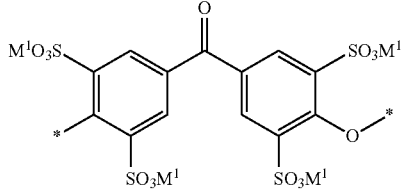
(S1-1)

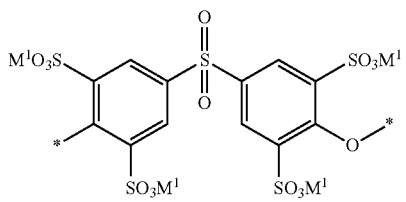
(S1-2)

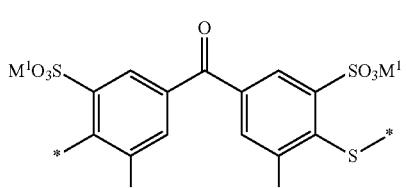
(S1-3)

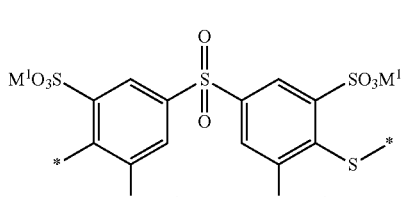
(S1-4)

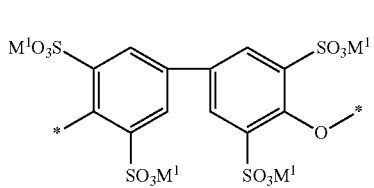
(S1-5)

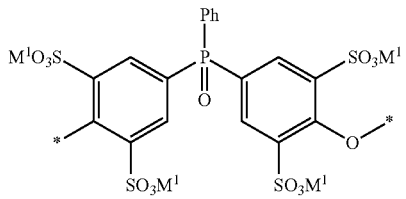
(S1-6)

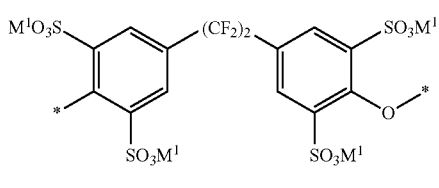
(S1-7)

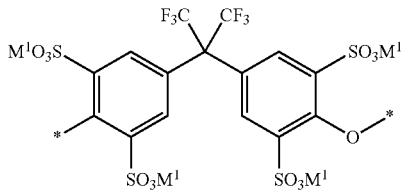
(S1-8)

[Chemical Formula 5]

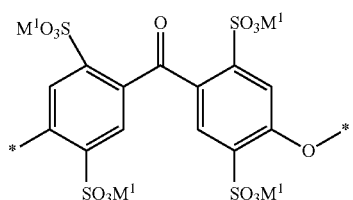
(S1-9)

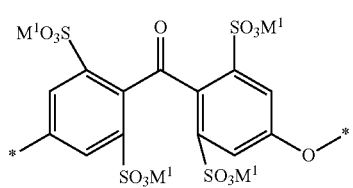
(S1-10)

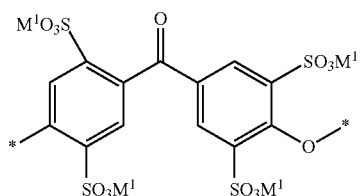
(S1-11)

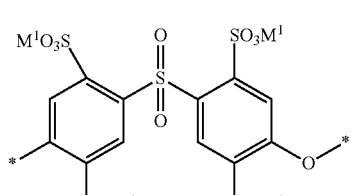
(S1-12)

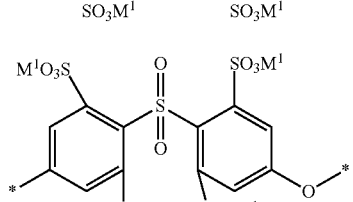
(S1-13)

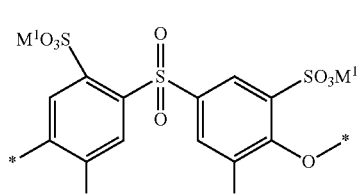
(S1-14)

In the formulas (S1-1) to (S1-14), $M^1$ is hydrogen, a metal cation, an ammonium cation or a hydrocarbon group having 1 to 20 carbon atoms.

Then, the sulfonic acid group-containing polymer of the present invention will be described.

A kind of the sulfonic acid group-containing polymer of the present invention is not particularly limited.

Specific examples thereof include sulfonic acid group-containing aromatic polyethers such as sulfonic acid group-containing aromatic polyether ketones, sulfonic acid group-containing aromatic polyether sulfones, and sulfonic acid group-containing aromatic polyether phosphine oxides, sulfonic acid group-containing aromatic polysulfides such as sulfonic acid group-containing aromatic polysulfide ketones, sulfonic acid group-containing aromatic polysulfide sulfones, and sulfonic acid group-containing aromatic polysulfide phosphine oxides, and the like.

Sulfonic acid group-containing polymers which are these sulfonic acid-containing aromatic polyethers and sulfonic acid group-containing aromatic polysulfides, and have one or more identical or different repeating structures having the following formula (S2) are a preferably specific example in the present invention.

[Chemical Formula 6]

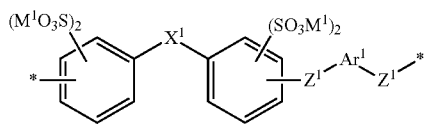

(S2)

In the repeating structures having formula (S2), each $X^1$ is independently one of a ketone group, a sulfone group, a direct linkage, $-PO(R^1)-$ (where $R^1$ is an organic group), $-(CF_2)_f-$ (where f is an integer from 1 to 5) or $-C(CF_3)_2-$; and each $Z^1$ is independently O or S; each $M^1$ is independently hydrogen, a metal cation, an ammonium cation or a hydrocarbon group having 1 to 20 carbon atoms. $Ar^1$ is an divalent group containing an aromatic ring. * is a bonding site with a moiety having the formula (S2) or other repeating structures.

In the present invention, the repeating structure includes one or a plurality of constituent unit(s), and is (are) present in a polymer repeatedly, and these constituent units may not necessarily be present adjacently and repeatedly, and another constituent unit may be present between repeating structures. Alternatively, the repeating structure may be present with a plurality of repeating structures, and another repeating structure may be present between repeating structures.

$X^1$ is more preferably a ketone group ($-CO-$), a sulfone group ($-SO_2-$), or a direct linkage from the view of chemical stability and cost, further preferably a ketone group or a sulfone group, and most preferably a ketone group from the view of physical durability. $Z^1$ is O or S from the view of cost and physical durability, and most preferably O. That is, it is most preferable that $X^1$ is a ketone group, and $Z^1$ is O.

From the view of cost and chemical stability, sulfonic acid group-containing aromatic polyether ketones, and sulfonic acid group-containing aromatic polyether sulfones are more preferable, and sulfonic group-containing aromatic polyether ketones are most preferable.

These sulfonic acid group-containing aromatic polyethers can be synthesized by an aromatic nucleophilic substitution reaction of a sulfonic acid group-containing aromatic compound (dihalide compound) having the following formula (M1) and any dihydric phenol compound. The dihydric phenol compound is not particularly limited, and can be appropriately selected in view of chemical stability, physical durability, cost and the like. Dihydric phenol compounds to which a sulfonic acid group has been introduced can be also used as a monomer in such a range that the effect of the present invention is not adversely affected, but from the view of reactivity, it is more preferable that the sulfonic acid group may not be contained.

[Chemical Formula 7]

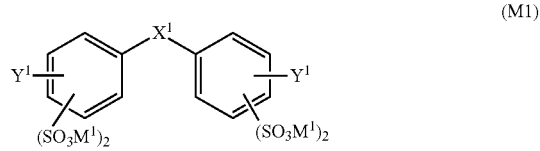

(M1)

In the compounds having formula (M1), each $X^1$ is independently one of a ketone group, a sulfone group, a direct linkage, $-PO(R^1)-$ (where $R^1$ is an organic group), $-(CF_2)_f-$ (where f is an integer from 1 to 5) or $-C(CF_3)_2-$; and each $Y^1$ is independently at least one of F, Cl, Br and I; each $M^1$ is independently hydrogen, a metal cation, an ammonium cation or a hydrocarbon group having 1 to 20 carbon atoms.

In the most preferable example of the sulfonic acid group-containing aromatic compound, a sulfonic acid group-containing aromatic compound having the following formula (M1-2) or (M1-3) is more preferable from the view of chemical stability and production cost, and a sulfonic acid group-containing aromatic compound having the following formula (M1-3) is most preferable. Usually, since these sulfonic acid group-containing aromatic compounds are synthesized by sulfonation of an aromatic compound, a sulfonic acid group is introduced into the ortho-position to a halogen atom, and the meta-position to an electron withdrawing $X^1$ group, provided that as in the constituent unit having the formulas (S1-9) to (S1-14), the position is not limited to the ortho-position to a halogen atom, and a sulfonation position can be selected by appropriately selecting a sulfonating agent and a functional group.

[Chemical Formula 8]

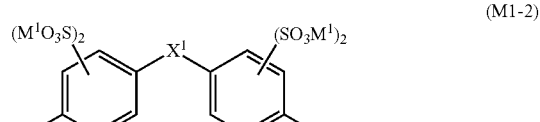

(M1-2)

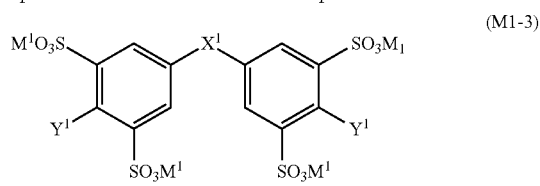

(M1-3)

In the compounds having formula (M1-2) and (M1-3), each $X^1$ is independently one of a ketone group, a sulfone group, a direct linkage, $-PO(R^1)-$ (where $R^1$ is an organic group), $-(CF_2)_f-$ (where f is an integer from 1 to 5) or $-C(CF_3)_2-$; and each $Y^1$ is independently at least one of F, Cl, Br and I; each $M^1$ is independently hydrogen, a metal cation, an ammonium cation or a hydrocarbon group having 1 to 20 carbon atoms.

Herein, specific examples of $Y^1$ include fluorine, chlorine, bromine and iodine, and from the view of reactivity, among them, fluorine and chlorine are more preferable, and fluorine is most preferable. Specific examples of the electron withdrawing group $X^1$ include a ketone group, a sulfone group, a direct linkage, —PO($R^1$)— (where $R^1$ is an organic group), —($CF_2$)$_f$— (where f is an integer from 1 to 5) and —C($CF_3$)$_2$—. Among them, from the view of chemical stability and cost, a ketone group (—CO—), a sulfone group (—$SO_2$—) and a direct linkage are more preferable, a ketone group and a sulfone group are further preferable, and from the view of physical durability, a ketone group is most preferable. That is, it is most preferable that $X^1$ is a ketone group, and $Y^1$ is F.

Since the aromatic sulfonic acid derivative of the present invention, due to the effect of the electron withdrawing group $X^1$, is excellent in chemical stability and, moreover, can locally enhance sulfonic acid group density when processed into a sulfonic acid group-containing polymer, excellent proton conductivity even under the low humidification condition can be realized.

By appropriately selecting a chemical structure, content mole ratio and the like of the aromatic sulfonic acid derivative of the present invention, it is possible to control various properties such as processability, a domain size, crystallinity/non-crystallinity, mechanical strength, proton conductivity, and dimensional stability.

In the present invention, $Ar^1$ in the formula (S2) is a divalent group including an aromatic ring, and is not particularly limited. Inter alia, from the view of chemical stability and physical durability, as $Ar^1$, a divalent group having the following formula (q1) or (q2) is more preferable. Further preferably a divalent group having the following formula (q1). $X^2$ is more preferably a ketone group (—CO—), a sulfone group (—$SO_2$—), or a direct linkage from the view of chemical stability and cost, further preferably a ketone group or a sulfone group, and most preferably a ketone group from the view of physical durability.

As the formula (S2), inter alia, from the view of chemical stability and production cost, a repeating structure having the following formula (S2-1) is further preferable:

[Chemical Formula 9]

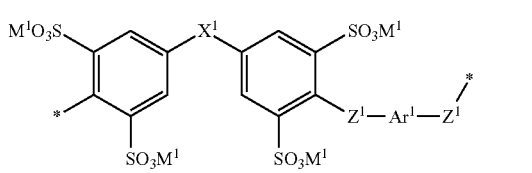

(S2-1)

In the repeating structure having formula (S2-1), each $X^1$ is independently one of a ketone group, a sulfone group, a direct linkage, —PO($R^1$)— (where $R^1$ is an organic group), —($CF_2$)$_f$— (where f is an integer from 1 to 5) or —C($CF_3$)$_2$—; and each $Z^1$ is independently O or S; each $M^1$ is independently hydrogen, a metal cation, an ammonium cation or a hydrocarbon group having 1 to 20 carbon atoms. $Ar^1$ is a divalent group having the following formula (q1) or (q2). $X^1$, $Z^1$, $Ar^1$ and $M^1$ may be different two or more kinds of groups. * is a bonding site with a moiety having the formula (S2) or other repeating structures.

[Chemical Formula 10]

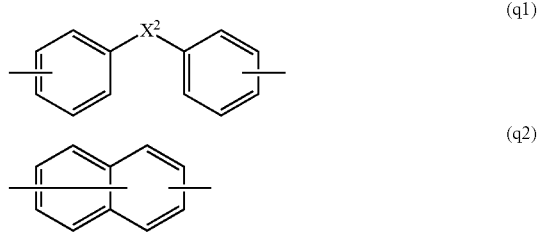

(q1)

(q2)

In the formula (q1), $X^2$ is one of a ketone group, a sulfone group, a direct linkage, —PO($R^1$)— (where $R^1$ is an organic group), —($CF_2$)$_f$— (where f is an integer from 1 to 5) or —C($CF_3$)$_2$—. A group having the formulas (q1) or (q2) may be substituted with any group including a sulfonic acid group.

$X^1$ is more preferably a ketone group (—CO—), a sulfone group (—$SO_2$—), or a direct linkage from the view of chemical stability and cost, further preferably a ketone group, or a sulfone group, and most preferably a ketone group from the view of physical durability. $Z^1$ is O or S from the view of cost and physical durability, and most preferably O. That is, it is most preferable that $X^1$ is a ketone group, and $Z^1$ is O. That is, it is a most preferably specific example that the repeating structure having the formula (S2) is a repeating structure having the following formula (S3):

[Chemical Formula 11]

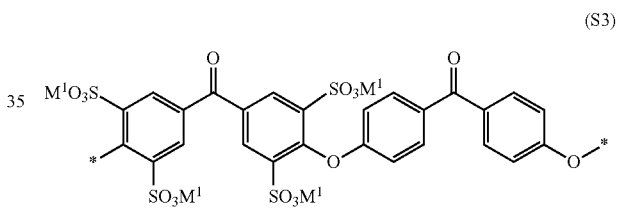

(S3)

In the formula (S3), each $M^1$ is independently hydrogen, a metal cation, an ammonium cation or a hydrocarbon group having 1 to 20 carbon atoms. * is a bonding site with a moiety having the formula (S3) or other constituent repeating structures.

A particularly preferably specific example among the repeating structures having the following formula (S2), that is, a structure in which $X^2$ in the formula (q1) is a ketone group (—CO—), a sulfone group (—$SO_2$—), or a direct linkage, and a structure having a group having the formula (q2) can be synthesized by an aromatic nucleophilic substitution reaction of a sulfonic acid group-containing aromatic compound (dihalide compound) having the formula (M2) and a dihydric phenol compound having the following formulas (Y-1) to (Y-4). A divalent thiol compound which is a hetero atom derivative of the dihydric phenol compound is also a preferable example.

[Chemical Formula 12]

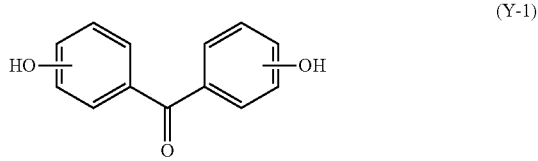

(Y-1)

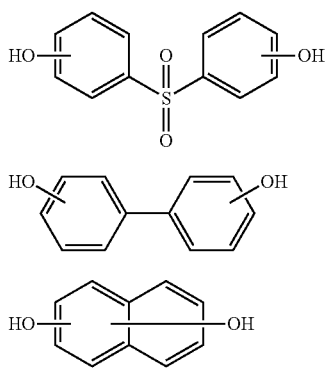

(Y-2)

(Y-3)

(Y-4)

Inter alia, from the view of low electron in benzene ring, and suppression of electrophilic reaction with hydroxyl radical, a dihydric phenol compound having the formulas (Y-1) to (Y-2) is more preferable, and from the view of water resistance and crystallinity, a dihydric phenol compound having (Y-1) is most preferable.

The dihydric phenol compound used in the sulfonic acid group-containing polymer of the present invention is not particularly limited thereto, and in view of chemical stability, physical durability, cost and the like, it can be appropriately copolymerized. Dihydric phenol compounds to which a sulfonic acid group has been introduced can be also used as a monomer in such a range and a position that the effect of the present invention is not adversely affected, that is, reactivity of a hydroxyl group is not reduced, but from the view of reactivity, it is more preferable that a sulfonic acid group may not be contained. Specific examples of the other dihydric phenols are dihydric phenol compounds having the following formulas (Y-5) to (Y-30):

[Chemical Formula 13]

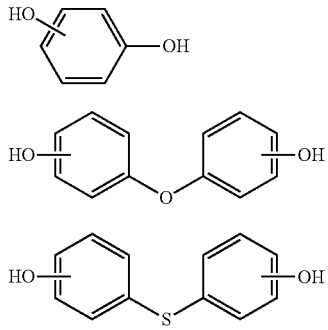

(Y-5)

(Y-6)

(Y-7)

Dihydric phenol compounds having the formulas (Y-5) to (Y-7) may be optionally substituted.

[Chemical Formula 14]

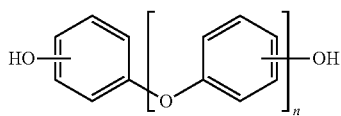

(Y-8)

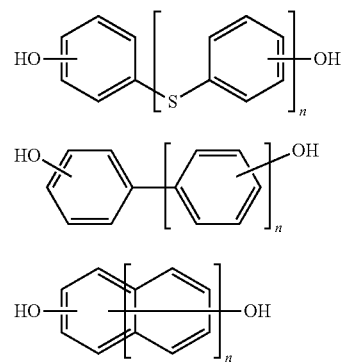

(Y-9)

(Y-10)

(Y-11)

Divalent phenol compounds having the formulas (Y-8) to (Y-11) may be optionally substituted, and n is an integer of 1 or more.

[Chemical Formula 15]

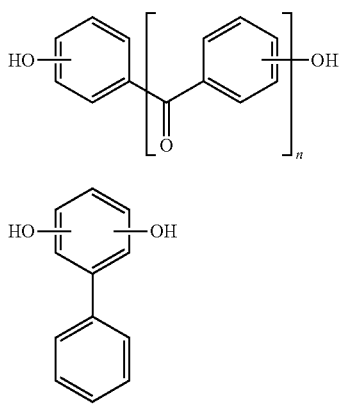

(Y-12)

(Y-13)

(Y-14)

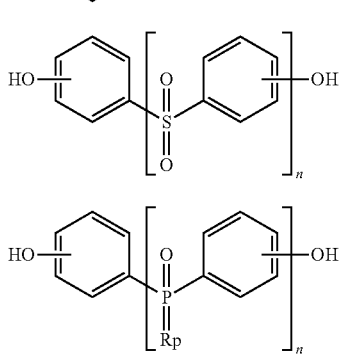

(Y-15)

(Y-16)

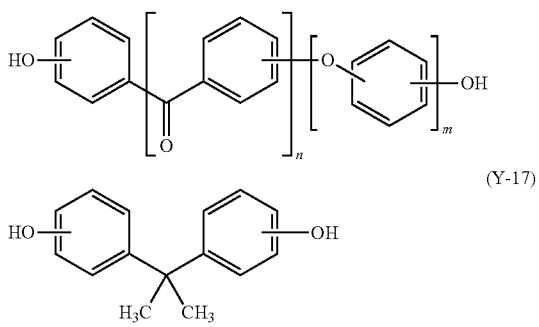

(Y-17)

(Y-18)
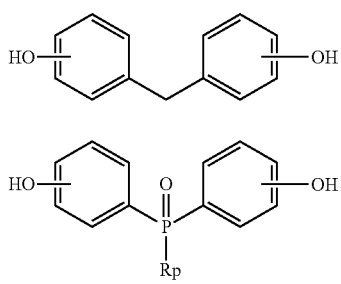

(Y-19)

Dihydric phenol compounds having the formulas (Y-12) to (Y-19) may be optionally substituted, n and m are respectively an integer of 1 or more, and Rp is an organic group.

[Chemical Formula 16]

(Y-20)
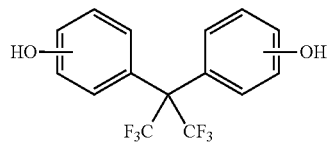

(Y-21)
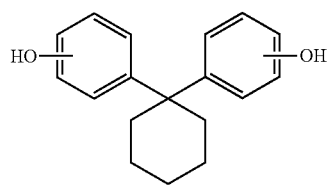

(Y-22)
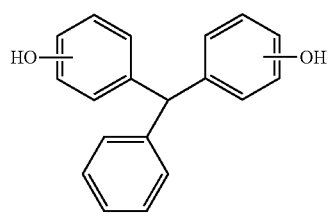

(Y-23)
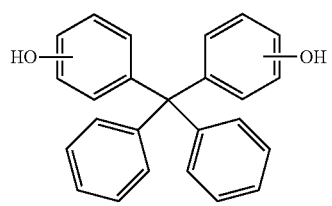

(Y-24)
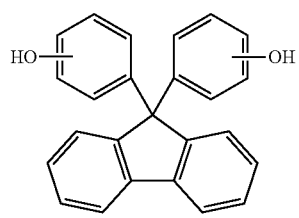

(Y-25)
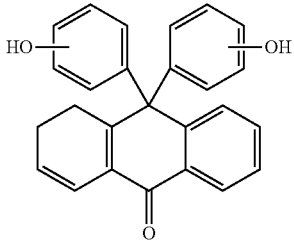

(Y-26)
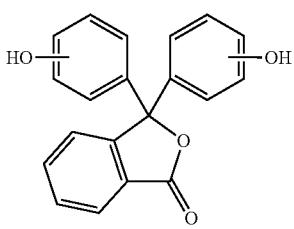

(Y-27)
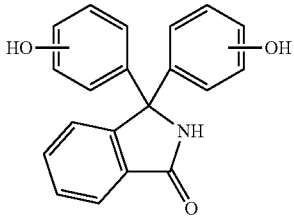

(Y-28)
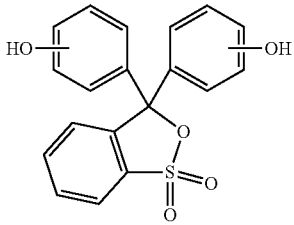

(Y-29)
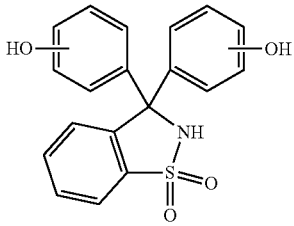

(Y-30)
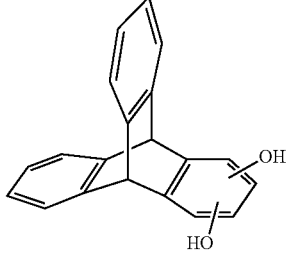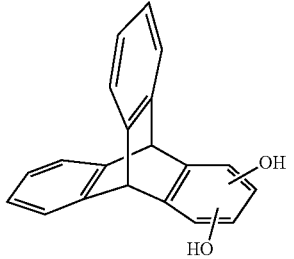

Dihydric phenol compounds having the formulas (Y-20) to (Y-30) may be optionally substituted.

In the present invention, it is also preferable that, in order to obtain the repeating structure having the formula (S3), a protective group is introduced into a dihydric phenol compound and, after polymerization or after molding, the compound is deprotected to convert into the repeating structure having the formula (S3). Preferably specific examples of a dihydric phenol compound having a protective group include compounds having the following formulas (r1) to (r10), and derivatives derived from these dihydric phenol compounds from the view of reactivity and chemical stability.

[Chemical Formula 17]

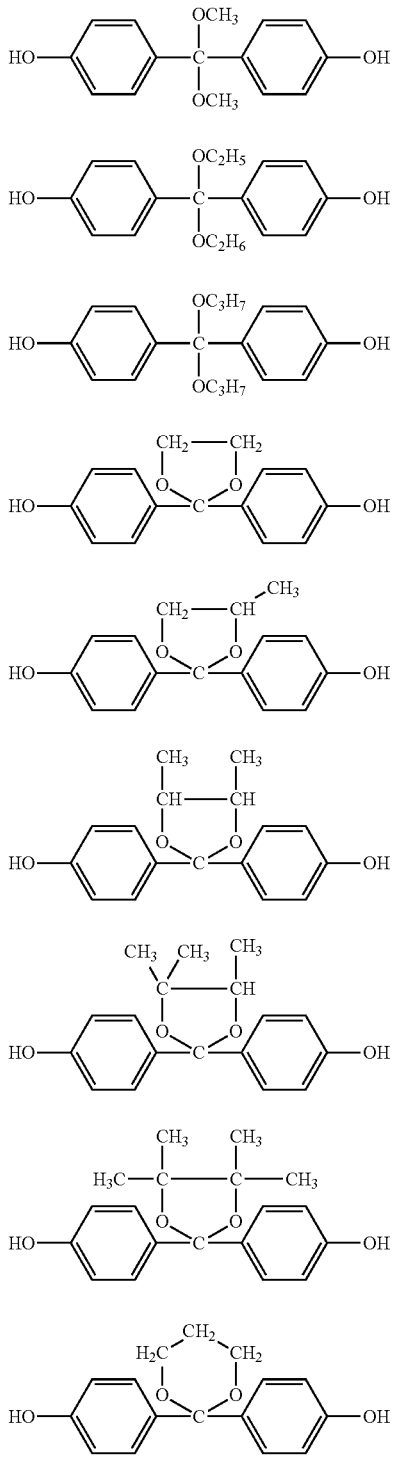

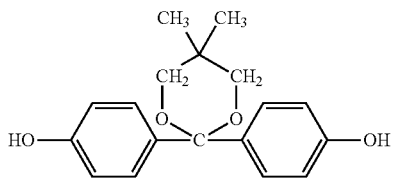

Among these dihydric phenol compounds, from the view of stability, compounds having the formulas (r4) to (r10) are more preferable, compounds having the formulas (r4), (r5) and (r9) are further preferable, and a compound having the formula (r4) is most preferable.

In the present invention, as a constituent unit containing a sulfonic acid group, a sulfonic acid group-containing aromatic active dihalide compound other than the formulas (M1) and (M2) can be copolymerized in such a range that the effect of the present invention is not deteriorated, that is, in such a range that low humidification proton conductivity can be maintained. Preferably specific examples of a monomer having a sulfonic acid group include, but are not limited to, 3,3'-disulfonate-4,4'-dichlorodiphenyl sulfone, 3,3'-disulfonate-4,4'-difluorodiphenyl sulfone, 3,3'-disulfonate-4,4'-dichlorodiphenyl ketone, 3,3'-disulfonate-4,4'-difluorodiphenyl ketone, 3,3'-disulfonate-4,4'-dichlorodiphenylphenylphosphine oxide, 3,3'-disulfonate-4,4'-difluorodiphenylphenylphosphine oxide, and the like.

In the aromatic active dihalide compound, a compound having a sulfonic acid group and a compound not having a sulfonic acid group are copolymerized, or a compound having a different introduction amount of a sulfonic acid group is copolymerized, and thus sulfonic acid group density can be also controlled. However, when the sulfonic acid group-containing polymer of the present invention is a block copolymer, from the view of securement of continuity in a proton conducting path, and improvement in low humidification proton conductivity, it is more preferable not to copolymerize an aromatic active dihalide compound not having a sulfonic acid group or an aromatic active dihalide compound having a small introduction amount of a sulfonic acid group.

More preferably specific examples of the aromatic active dihalide compound not having a sulfonic acid group include 4,4'-dichlorodiphenyl sulfone, 4,4'-difluorodiphenyl sulfone, 4,4'-dichlorodiphenyl ketone, 4,4'-difluorodiphenyl ketone, 4,4'-dichlorodiphenylphenylphosphine oxide, 4,4'-difluorodiphenylphenylphosphine oxide, 2,6-dichlorobenzonitrile, 2,6-difluorobenzonitrile, and the like. Among them, 4,4'-dichlorodiphenyl ketone, and 4,4'-difluorodiphenyl ketone are more preferable from the view of crystallinity impartation, mechanical strength, physical durability, and hot water resistance, and 4,4'-difluorodiphenyl ketone is most preferable from the view of polymerization activity. These aromatic active dihalide compounds can be used alone, and a plurality of the aromatic active dihalide compounds can be also used in combination.

A halogenated aromatic hydroxy compound is not particularly limited, and examples thereof include 4-hydroxy-4'-chlorobenzophenone, 4-hydroxy-4'-fluorobenzophenone, 4-hydroxy-4'-chlorodiphenyl sulfone, 4-hydroxy-4'-fluorodiphenyl sulfone, 4-(4'-hydroxybiphenyl) (4-chlorophenyl) sulfone, 4-(4'-hydroxybiphenyl) (4-fluorophenyl) sulfone, 4-(4'-hydroxybiphenyl) (4-chlorophenyl) ketone, 4-(4'-hydroxybiphenyl) (4-fluorophenyl) ketone, and the like. These compounds can be used alone, or can be also used as a mixture of two or more kinds. Further, these halogenated aromatic hydroxy compounds may be also reacted together in a reaction of an activated dihalogenated aromatic compound and an aromatic dihydroxy compound to synthesize an aromatic polyether compound.

It is preferable that the sulfonic acid group-containing polymer of the present invention is a block copolymer containing one or more segments containing a sulfonic acid group (B1) and one or more segments not containing a sulfonic acid group (B2), both containing the constituent unit having the formula (S1), from the view of formation of a proton conducting channel and low humidification proton conductivity. Also herein, when the constituent unit having the formula (S1) is less than 25 mol %, proton conductivity under the low humidification condition, which is the effect of the present invention, is deficient in some cases, and this is not preferable.

In the present invention, the segment is a partial structure in a block copolymer, includes one kind of a repeating structure or a combination of a plurality of kinds of repeating structures, and has a molecular weight of 2000 or more.

In the present invention, the segment containing a sulfonic acid group (B1) is a segment including a repeating structure having a sulfonic acid group, and includes a repeating structure containing one or a plurality of sulfonic acid group(s). This repeating structure containing a sulfonic acid group may be present in the segment repeatedly, but may not be necessarily present adjacently and repeatedly, and another constituent unit may be present between repeating structures. Alternatively, the repeating structure may be present with a plurality of repeating structures, and another repeating structure may be present between repeating structures.

In the present invention, the segment not containing a sulfonic acid group (B2) is a segment including a repeating structure not having a sulfonic acid group, and includes a repeating structure not containing one or a plurality of sulfonic acid group(s). This repeating structure not containing a sulfonic acid group may be present in the segment repeatedly, but may not be necessarily present adjacently and repeatedly, and another constituent unit may be present between repeating structures. Alternatively, the repeating structure may be present with a plurality of repeating structures, and another repeating structure may be present between repeating structures.

In the present invention, the above segment is described as "segment not containing a sulfonic acid group", however the segment (B2) may contain a small amount of a sulfonic acid group in such a range that the effect of the present invention is not adversely affected. Hereinafter, "not containing a sulfonic acid group" is used in the similar sense, in some cases.

A block copolymer obtained from the present invention is such that two or more kinds of mutually incompatible segment chains, that is, a hydrophilic segment containing a sulfonic acid group, and a hydrophobic segment not containing a sulfonic acid group are linked to form one polymer chain. In the block copolymer, due to short distance interaction generated from repulsion between chemically different segment chains, the block copolymer is phase-separated into nano- or micro-domains including each segment chain, and due to the effect of long distance interaction generated from mutual covalent bond of segment chains, each domain is made to be arranged having a specified order. A high order structure created by aggregation of domains including each segment chain is referred to as a nano or micro phase-separated structure, and regarding ion conduction of a polymer electrolyte membrane, spatial arrangement of ion conductive segments in the membrane, that is, a nano or micro phase-separated structure becomes important. Herein, the domain means a mass generated by aggregation of similar segments in one or a plurality of polymer chain(s).

The block copolymer obtained from the present invention can realize chemical durability or physical durability and excellent proton conductivity, particularly, high proton conductivity even under the low humidification condition through formation of a proton conductive channel in which sulfonic acid group density is locally enhanced, by containing the constituent unit having the formula (S1) in the segment containing a sulfonic acid group (B1) as a chemical structure, and controlling the nano or micro phase-separated structure as a polymer high order structure.

By appropriately selecting a chemical structure, segment chain length, molecular weight, ion exchange capacity and the like of the block copolymer obtained from the present invention, various properties such as processability, a domain size, crystallinity/non-crystallinity, mechanical strength, proton conductivity, and dimensional stability of a polymer electrode material can be controlled.

The block copolymer obtained from the present invention can realize excellent proton conductivity even under the low humidification condition as a polymer electrode material or a polymer electrolyte membrane, by formation of a domain by the segment containing a sulfonic acid group (B1).

Then, the segment containing a sulfonic acid group (B1) will be described.

The segment containing a sulfonic acid group (B1) is characterized in that it contains the constituent unit having the formula (S1), a segment which is chemically stable, has high acidity due to the electron withdrawing effect, and has a sulfonic acid group introduced thereinto at high density is more preferable, and a block copolymer excellent in proton conductivity under the low humidification condition can be obtained.

The polymers listed as preferably specific examples of the sulfonic acid group-containing polymer of the present invention, and the polymers listed as particularly preferable examples thereof are also preferable as the segment containing a sulfonic acid group (B1) similarly from the view of low humidification proton conductivity. Examples thereof include, as described above, the repeating structure having the formula (S2-1), more preferably the repeating structure having the formula (S2), and further preferably the repeating structure having the formula (S3).

Then, the segment not containing a sulfonic acid group (B2) will be specifically described.

As the segment not containing a sulfonic acid group (B2), a constituent unit which is chemically stable and, moreover, exhibits crystallinity due to a strong intermolecular aggregation force is more preferable, and a block copolymer excellent in mechanical strength, dimensional stability and physical durability can be obtained.

The block copolymer obtained from the present invention is more preferably such that the segment not containing a sulfonic acid group (B2) contains a repeating structure having the following formula (P1):

[Chemical Formula 18]

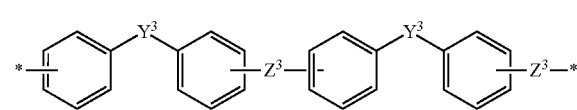

(P1)

A site having the formula (P1) may be optionally substituted, but does not contain a sulfonic acid group. $Y^3$ is an electron withdrawing group, and $Z^3$ is an electron withdrawing group, O or S. * is a bonding site with a moiety having the formula (P1) or other constituent units.

Herein, specific examples of the electron withdrawing group $Y^3$ include —CO—, —$(CF_2)_n$— (where n is an integer from 1 to 5), —$C(CF_3)_2$—, —$SO_2$—, —$PO(R^1)$— (where $R^1$ is an organic group) and the like. Among them, from the view of chemical stability and cost, —CO— and —$SO_2$— are more preferable, and from the view of physical durability, —CO— is most preferable.

Specific examples of $Z^3$ include electron withdrawing groups such as —CO—, —$(CF_2)_n$— (where n is an integer from 1 to 5), —$C(CF_3)_2$—, —$SO_2$—, and —$PO(R^1)$— (where $R^1$ is an organic group); —O— and —S—, and from the view of cost and physical durability, —O— and —S— are more preferable, and —O— is most preferable.

Since the constituent unit having the formula (P1), due to the effect of the electron withdrawing group $Y^1$, is excellent in chemical stability and, moreover, can enhance mechanical strength and water resistance when processed into a block copolymer, a reinforcing three-dimensional network is formed, and excellent physical durability can be realized.

A proportion of the constituent unit having the formula (P1) relative to the segment not containing a sulfonic acid group is preferably higher from the view of physical durability and chemical stability, more preferably 25 mol %, further preferably 50 mol % or more, particularly preferably 75 mol % or more, and most preferably 90 mol % or more.

More preferably specific examples of the constituent unit having the formula (P1) contained in the segment not containing a sulfonic acid group (B2) include constituent units having the following formulas (P2-1), (P2), and (P4-1) to (P4-8) from the view of raw material availability. Among them, from the view of mechanical strength, dimensional stability and physical durability due to crystallinity, a constituent unit having the following formula (P2), (P4-1) or (P4-2) is further preferable, and a constituent unit having the following formula (P2) is most preferable.

A content of the constituent unit having the formula (P2) contained in the segment not containing a sulfonic acid group (B2) is preferably greater, more preferably 25 mol % or more, further preferably 50 mol % or more, and most preferably 75 mol % or more. When the content is less than 25 mol %, the effect of the present invention on mechanical strength, dimensional stability and physical durability due to crystallinity is deficient in some cases, and this is not preferable.

[Chemical Formula 19]

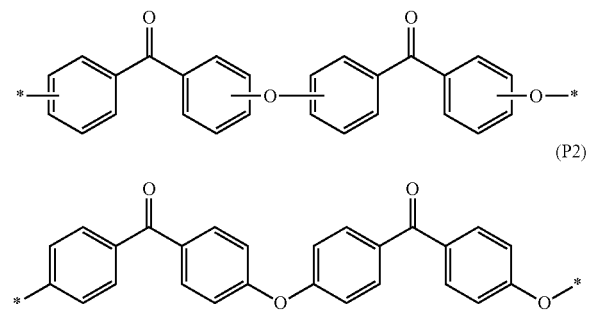

(P2-1)

(P2)

[Chemical Formula 20]

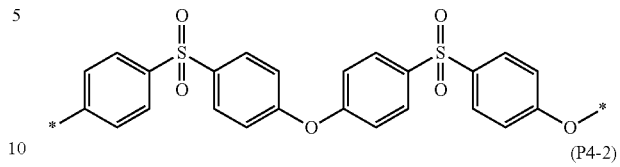

(P4-1)

(P4-2)

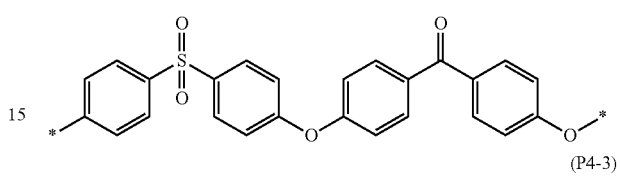

(P4-3)

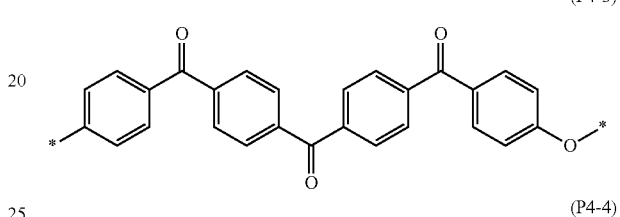

(P4-4)

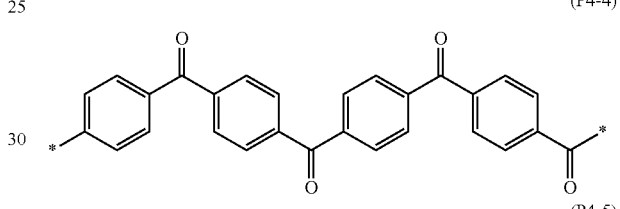

(P4-5)

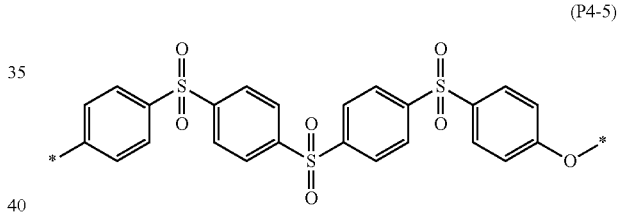

(P4-6)

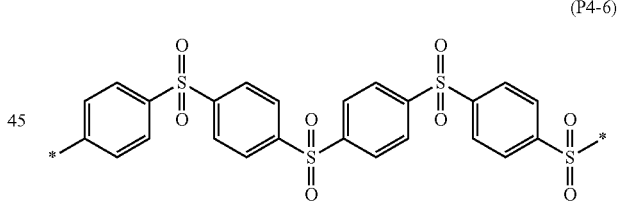

(P4-7)

(P4-8)

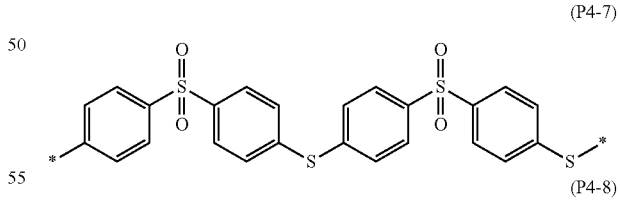

Preferable examples of a constituent unit to be copolymerized other than the constituent unit having the formula (P1), as the segment not containing a sulfonic acid group (B2), include a constituent unit having an aromatic polyether polymer containing a ketone group, that is, a constituent unit which has the following formula (Q1), and dose not contain a sulfonic acid group:

[Chemical Formula 21]

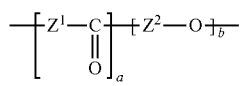
(Q1)

In the formula (Q1), $Z^1$ and $Z^2$ are a divalent organic group containing an aromatic ring, and each of them may be two or more kinds of groups, but does not contain a sulfonic acid group. a and b each are independently a positive integer.

As a preferable organic group as $Z^1$ and $Z^2$ in the formula (Q1), it is more preferable that $Z^1$ is a phenylene group, and $Z^2$ is at least one of the following formulas (X-1), (X-2), (X-4) and (X-5). The organic group may be substituted with a group other than a sulfonic acid group, but it is more preferable that the organic group is not substituted, from the view of crystallinity impartation. $Z^1$ and $Z^2$ are further preferably a phenylene group, and most preferably a p-phenylene group.

[Chemical Formula 22]

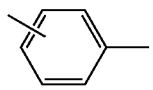
(X-1)

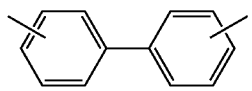
(X-2)

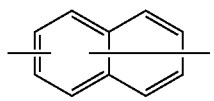
(X-4)

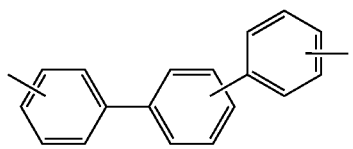
(X-5)

Groups having the formulas (X-1), (X-2), (X-4) and (X-5) may be optionally substituted with a group other than a sulfonic acid group.

Preferably specific examples of the constituent unit having the formula (Q1) include, but are not limited to, constituent units having the following formulas (Q2) to (Q7) and the like, and the constituent unit having the formula (Q1) can be appropriately selected in view of crystallinity and mechanical strength. Among them, from the view of crystallinity and production cost, as the constituent unit having the formula (Q1), the following formulas (Q2), (Q3), (Q6) and (Q7) are more preferable, and the formulas (Q2) and (Q7) are most preferable:

[Chemical Formula 23]

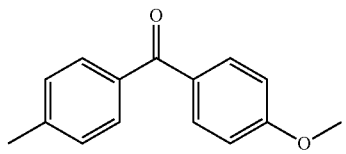
(Q2)

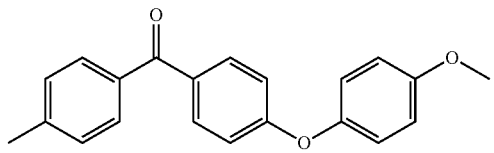
(Q3)

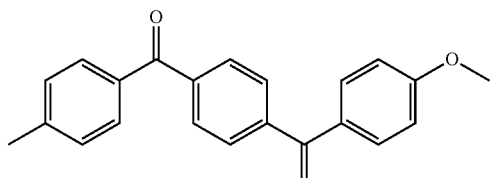
(Q4)

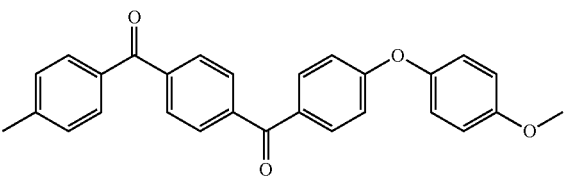
(Q5)

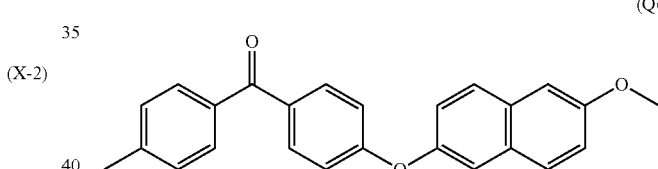
(Q6)

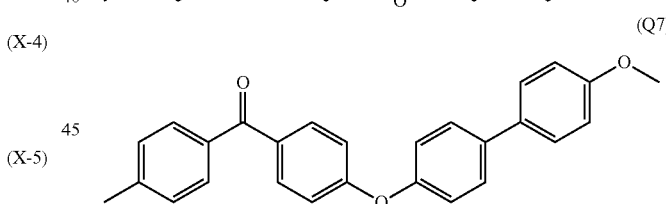
(Q7)

The formulas (Q2) to (Q7) are all expressed at the para-position, but when they have crystallinity, other binding position such as the ortho-position or the meta-position may be contained. However, from the view of crystallinity, the para-position is more preferable.

It is further preferable that the block copolymer obtained from the present invention further contains one or more linker site(s) linking between the segment containing a sulfonic acid group (B1) and the segment not containing a sulfonic acid group (B2).

Herein, in the present invention, the linker is defined as a site linking between the segment containing a sulfonic acid group (B1) and the segment not containing a sulfonic acid group (B2), and having a chemical structure different from that of the segment containing a sulfonic acid group (B1) and the segment not containing a sulfonic acid group (B2). Since this linker can link different segments while randomization, segment cutting and a side reaction due to an ether exchange reaction are suppressed, it is particularly preferable for obtaining the block copolymer obtained from the present invention. When there is no linker, segment cutting such as randomization occurs in some cases, and the effect of the present invention is not sufficiently obtained in some cases.

It is necessary that the linker used in the present invention is a compound having such high reactivity that different segments can be linked, while randomization and segment cutting due to the ether exchange reaction are suppressed, and specific examples thereof which are preferable in the present invention include, but are not limited to, decafluorobiphenyl, hexafluorobenzene, 4,4'-difluorodiphenyl sulfone, 2,6-difluorobenzonitrile, and the like. When a polyfunctional linker such as decafluorobiphenyl or hexafluorobenzene is used, a block copolymer having a branched structure can be made by controlling the reaction condition. At this time, by changing preparation composition of a polymer having an unsulfonated segment of the formula (P1) and a polymer having a sulfonated segment of the formula (S2), a block copolymer of a linear structure and a block copolymer having a branched structure can be also made individually.

A method of synthesizing the sulfonic acid group-containing aromatic compounds (M1) and (M2) of the present invention will be described.

The sulfonic acid group-containing aromatic compound of the present invention is characterized in that it locally enhances sulfonic acid group density by introducing two sulfonic acid groups into one benzene ring. It is known that since a sulfonation reaction is an electrophilic substitution reaction on a benzene ring, reactivity of the benzene ring to which a sulfonic acid group has been introduced becomes extremely low. Therefore, in the prior art, such a feature has been hardly studied.

In order to attain disulfonation on a benzene ring, the present inventors have studied intensively and, as a result, found out that by carrying out a high temperature reaction while evaporation of sulfur trioxide is suppressed, a disulfonation reaction on a benzene ring favorably proceeds, a side reaction hardly occurs and, further, an inorganic salt which is made as a byproduct can be removed by recrystallization and, at the same time, further studied variously, and succeeded in obtaining the sulfonic acid group-containing aromatic compound of the present invention at high purity. However, a method of synthesizing the sulfonic acid group-containing aromatic compounds (M1) and (M2) of the present invention is not limited thereto.

A method of making a sulfonic group-containing aromatic compound comprising reacting an aromatic compound having the following formula (M1) with fuming sulfuric acid, wherein the reaction is carried out at 120° C. to 250° C. in a closed system under an elevated pressure; and wherein the sulfonic group-containing aromatic compound have the following formula (M2):

[Chemical Formula 24]

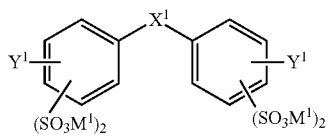

(M1)

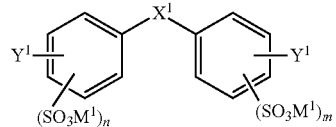

(M2)

In the formulas (M1) and (M2), each $X^1$ is independently one of a ketone group, a sulfone group, a direct linkage, —PO($R^1$)— (where $R^1$ is an organic group), —($CF_2$)$_f$— (where f is an integer from 1 to 5) or —C($CF_3$)$_2$—; and each $Y^1$ is independently at least one of F, Cl, Br and I; each $M^1$ is independently hydrogen, a metal cation, an ammonium cation or a hydrocarbon group having 1 to 20 carbon atoms. m is 0 or 1; n is 0 or 1.

Herein, specific examples of $Y^1$ include fluorine, chlorine, bromine and iodine, and from the view of reactivity, among them, fluorine and chlorine are more preferable, and fluorine is most preferable. Specific examples of the electron withdrawing group $X^1$ include a ketone group, a sulfone group, a direct linkage, —PO($R^1$)— (where $R^1$ is an organic group), —($CF_2$)$_f$— (where f is an integer from 1 to 5) and —C($CF_3$)$_2$—. Among them, from the view of chemical stability and cost, a ketone group (—CO—), a sulfone group (—$SO_2$—) and a direct linkage are more preferable, a ketone group and a sulfone group are further preferable, and from the view of physical durability, a ketone group is most preferable. That is, it is most preferable that $X^1$ is a ketone group, and $Y^1$ is F.

From the view of chemical point, $R^1$ is preferably at least one of hydroxyl, carboxyl, amino, halogen, alkyl, cycloalkyl, alkenyl, cycloalkene, aryl, silyl, ester group, oxyalkyl, oxyaryl or their derivatives. From the view of structure stability, $R^1$ is more preferably at least one of alkyl with C1~C10, cycloalkyl with C3~C10, aryl, sulfonic group-containing aryl, oxyalkyl with C1~C10, oxyaryl, sulfonic group-containing oxyaryl or their derivatives. From the view of difficulty to obtain the compounds, $R^1$ is particularly preferable at least one of aryl, sulfonic group-containing aryl or their derivatives. Sulfonic group-containing phenyl is most preferred.

$M^1$ is a metal cation or an ammonium cation, wherein the metal cation is preferably at least one ion of sodium, potassium, aluminum, magnesium, calcium, copper, nickel, cobalt, lead, zinc, tin, antimony, bismuth, silver, platinum, ruthenium, rhodium, palladium, osmium, tungsten, molybdenum, tantalum, niobium, zirconium, hafnium, vanadium, titanium, indium, thallium, germanium, selenium or tellurium. From the view of the cost and availability of the starting compound, sodium, potassium, aluminum, magnesium, calcium, copper, zinc or silver are more preferred.

In the method of making a sulfonic group-containing aromatic compound according to the present invention, the reaction is carried out at 120° C. to 250° C. in a closed system and under an elevated pressure. In the closed system with pressure, vaporization of sulfuric trioxide in fuming sulfuric acid can be prevented; on the other hand, the collision between reaction molecules can be increased and the reaction efficiency can thus be improved.

If the reaction temperature is lower than 120° C., the desired reaction scarcely proceeds, and if the temperature is higher than 250° C., thermal decomposition of the raw material and the reaction product may occur. In the method according to the present invention, the reaction time is directly correlated with the reaction temperature, and is therefore not particularly limited. Less reaction time is needed at a higher temperature, and much reaction time is required at a lower temperature. The reaction time should be controlled such that the sulfonic group-containing aromatic compound having the formula (M2) can be obtained. The reaction time is preferably in the range of 1 to 48 hrs. If the time is shorter than 1 hr, it may be difficult to obtain the desired compound; on the other hand, if the reaction time is more than 48 hrs, the side reactions such as decomposition reaction of the reaction product may occur.

In the method according to the present invention, the closed system is a pressure-resistant, heat-resistant and corrosion-resistant sealed container, and is preferably an autoclave lined with polytetrafluoroethene (PTFE), silicon dioxide hastelloy alloy and titanium. In the present invention, the closed system also includes the vigorous nitrogen flow system as well as the sealed container because, as noted above, it is important to carry out a high temperature reaction while evaporation of sulfur trioxide is suppressed and vigorous nitrogen flow system practically has the similar effects of the suppression of sulfur trioxide evaporation to the sealed container. The sealed container like an autoclave is described specifically by the Example 17-27 and the vigorous nitrogen flow system is described specifically by the Example 1-3.

In the method according to the present invention, the reaction pressure should be higher than a normal atmosphere. It will be hard to obtain the sulfonic group-containing aromatic compound having the formula (M2) under a normal atmosphere. In the method according to the present invention, there are no limitations on the upper limit of the reaction pressure. However, from the view of reaction safety, the higher the reaction pressure, the more dangerous the reaction is. In view of that the sulfur trioxide used in the method has high causticity, and considering the cost of equipment, the reaction pressure is preferably in a range of 0.12 MPa to 5.0 MPa, and more preferably 0.15 MPa to 3.0 MPa, and particularly preferably 0.2 MPa to 1.5 MPa.

In the method according to the present invention, the concentration of sulfur trioxide in fuming sulfuric acid is 20% to 65% by weight. A fuming sulfuric acid having a concentration of sulfur trioxide in the range of 20% to 65% by weight is commercially available.

In the method according to the present invention, from the view of the difficulty of occurrence of substitution reaction, the sulfonic group-containing aromatic compound of formula (M1) preferably has the formula (M3) as shown below:

[Chemical Formula 25]

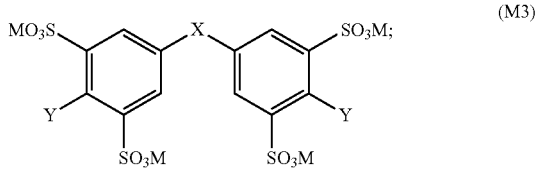

In the formula (M3), X is one of a ketone group, a sulfone group, a direct linkage, —PO($R^1$)— (where $R^1$ is an organic group), —(CF$_2$)$_f$— (where f is an integer from 1 to 5) or —C(CF$_3$)$_2$—; Y is at least one F, Cl, Br or I; m is 0 or 1; n is 0 or 1; M is a metal cation or an ammonium cation.

From the view of availability of the starting compound, X is preferably one kind of a ketone group, or a sulfone group. From the view of the reactivity, Y is preferably at least one of F, or Cl.

From the view of structure stability, $R^1$ is further preferably at least one of alkyl with C1~C10, cycloalkyl with C3~C10, aryl, sulfonic group-containing aryl, oxyalkyl with C1~C10, oxyaryl, sulfonic group-containing oxyaryl or their derivatives. Further, taking the availability of the starting compound into consideration, at least one of aryl, sulfonic group-containing aryl or their derivatives is preferred.

M is a metal cation or an ammonium cation. In view of the cost and availability of the starting compound, sodium, potassium, aluminum, magnesium, calcium, copper, zinc or silver are preferred.

From the view of the cost and reactivity, the resulting sulfonic group-containing aromatic compound particularly preferably has the formula (M4) as shown below:

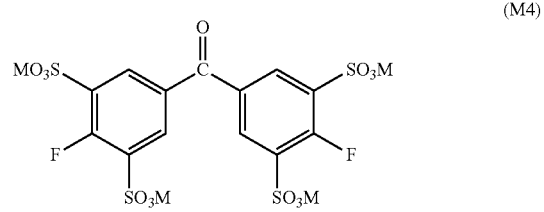

In the formula (M4), M is a metal cation or an ammonium cation.

M is preferable as described above.

In the present invention, in addition to the step of reacting an aromatic compound having the formula (M1) with fuming sulfuric acid, the method of making a sulfonic group-containing aromatic compound having the formula (M2) further comprises the steps (1) to (3):
(1) reacting an aromatic compound having the formula (M1) with fuming sulfuric acid, and then neutralizing the reaction mixture, and removing the solvent therein;
(2) redissolving the reaction mixture obtained from the step (1) with a solvent, removing the undissolved matter in the reaction mixture, and then removing the solvent;
(3) recrystallizing the reaction mixture obtained from the step (2) in a solvent.

During the method of reacting an aromatic compound having the formula (M1) with fuming sulfuric acid to form a sulfonic group-containing aromatic compound having the formula (M2), sulfuric trioxide in the fuming sulfuric acid plays a major role, so the structure of the final product is greatly affected by the equivalent ratio of sulfur trioxide in the fuming sulfuric acid to the aromatic compound having the formula (M1). The equivalent ratio of sulfur trioxide in the fuming sulfuric acid to the aromatic compound having the formula (M1) is 2-30:1. If the equivalent ratio is lower than 2:1, a sulfonic group-containing aromatic compound having the formula (M2) may not be obtained. On the other hand, if the equivalent ratio is higher than 30:1, the concentration of sulfur trioxide is too high, and may not be favorable for the post treatment of the reaction product.

During the synthesis method of a sulfonic group-containing aromatic compound having the formula (M2), fuming sulfuric acid is used as the raw materials, and therefore, when the reaction is completed, the reaction system is acidic. Thus, the system is firstly neutralized with a base until the pH value thereof reaches to 7.0~7.5. In the method according to the present invention, the base used for neutralizing is at least one kind of alkali metal hydroxide, alkali metal carbonate, alkali metal bicarbonate or ammonia. In view of the cost and availability thereof, the base is preferably at least one kind of sodium hydroxide, potassium hydroxide, sodium carbonate, potassium carbonate, sodium bicarbonate, potassium bicarbonate or ammonia water.

In the method of making a sulfonic group-containing aromatic compound according to the present invention, the solvent used for redissolving in the step (2) is at least one kind of dimethyl sulfoxide, thionyl chloride, 4,4'-diaminodiphenyl sulfone, 4,4'-sulfonyl diphenol, 4,4'-dimethyl diphenyl sulfoxide, sulfolane, diphenyl sulfone or phenyl sulfoxide. From the view of the properties, cost and toxicity of the solvent, dimethyl sulfoxide is most preferred.

In the method of making a sulfonic group-containing aromatic compound according to the present invention, removal of the dissolved matter in the step (2) is achieved through precipitation and separation processes of the sulfone solution of the reaction product. In the precipitation process, the sulfone solution of the reaction product is precipitated in an alcohol or ketone solvent. The alcohol solvent is at least one kind of methanol, ethanol, isopropanol, n-propanol, n-butanol, tertiary butyl alcohol, isopropyl alcohol, n-butyl alcohol, isoamyl alcohol, amyl alcohol, tertiary amyl alcohol, cyclopentanol, hexanol, octanol, cyclohexanol, octanol, decanol, or benzyl alcohol; the ketone solvent is at least one kind of acetone, methyl ethyl ketone, methyl amyl ketone, methyl isopropyl ketone, methyl isobutyl ketone or cyclohexanone. Considering the properties, cost and toxicity of the solvent, the alcohol solvent is preferably at least one kind of methanol or ethanol, and the ketone solvent is preferably acetone. The separation process is usually a filtration or centrifugation process.

In the method of making a sulfonic group-containing aromatic compound according to the present invention, removal of the solvent in the step (2) is a drying process, which is carried out at 100 to 150° C. for 6 to 72 hrs. To completely remove the residual solvent and water in the reaction product, the drying process is preferably carried out in vacuum condition.

In the method of making a sulfonic group-containing aromatic compound according to the present invention, recrystallizing in the step (3) is carried out at 4 to 25° C. in deionized water or a mixture of deionized water and an alcohol or ketone solvent. The volume ratio of alcohol or ketone and deionized water in the mixture is 0 to 4:1.

By the making method of the present invention, a sulfonic acid group-containing aromatic compound having the formula (M1) at high purity, in which a content of the aromatic compound having the formula (M2) is 5% by weight or less, can be obtained, and since a sulfonic acid group-containing polymer and block copolymer obtained from the resulting sulfonic acid group-containing aromatic compound can attain an extremely high ion exchange capacity, they are excellent in proton conductivity and, therefore, they can be particularly preferably used.

When the block copolymer obtained from the present invention has a sulfonic acid group, an ion exchange capacity thereof is preferably 0.1 to 5 meq/g, more preferably 1.5 meq/g or more, further preferably 2 meq/g or more, and most preferably 2.5 meq/g from the view of a balance between proton conductivity and water resistance. Further, it is more preferably 4 meq/g or less, further preferably 3.5 meq/g or less, and most preferably 3 meq/g or less. When the ion exchange capacity is smaller than 0.1 meq/g, proton conductivity is deficient in some cases, and when the ion exchange capacity is greater than 5 meq/g, water resistance is deficient in some cases.

In the block copolymer obtained from the present invention, a molar composition ratio (B1/B2) of the segment containing a sulfonic acid group (B1) and the segment not containing a sulfonic acid group (B2) is more preferably 0.2 or more, further preferably 0.33 or more, and most preferably 0.5 or more. Further, it is more preferably 5 or less, further preferably 3 or less, and most preferably 2 or less. When the molar composition ratio B1/B2 is less than 0.2, or is more than 5, the effect of the present invention becomes insufficient in some cases, proton conductivity under the low humidification condition is deficient, and hot water resistance and physical durability are deficient in some cases, and this is not preferable.

Herein, the molar composition ratio (B1/B2) is a ratio of a mol number of a repeating structure present in the segment (B1) and a mol number of a repeating structure present in the segment (B2). For example, when the segment (B1) includes the constituent unit containing a sulfonic acid group (S2), and the segment (B2) includes the constituent unit not containing a sulfonic acid group (P1), the molar composition ratio means a ratio of a value obtained by dividing a number average molecular weight of each segment by a molecular weight of the constituent unit (S2) corresponding each of them. When each segment is not a homopolymer, but is a random copolymer, an alternate copolymer, or a block copolymer, the molar composition ratio means a ratio of a value obtained by dividing a number average molecular weight of each segment by an average molecular weight calculated in view of each content mole ratio.

An ion exchange capacity of the segment containing a sulfonic acid group (B1) is preferably high from the view of proton conductivity under the low humidification condition, more preferably 2.5 meq/g or more, further preferably 3.5 meq/g or more, and most preferably 4.5 meq/g or more. Further, it is more preferably 7.5 meq/g or less, further preferably 6.5 meq/g or less, and most preferably 5 meq/g or less. When the ion exchange capacity of the segment containing a sulfonic acid group (B1) is less than 2.5 meq/g, proton conductivity under the low humidification condition is deficient in some cases, and when the capacity is more than 7.5 meq/g, hot water resistance or physical durability is deficient in some cases, and this is not preferable.

An ion exchange capacity of the segment not containing a sulfonic acid group (B2) is preferably low from the view of hot water resistance, mechanical strength, dimensional stability and physical durability, more preferably 1 meq/g or less, further preferably 0.5 meq/g, and most preferably 0.1 meq/g or less. When the ion exchange capacity of the segment not containing a sulfonic acid group (B2) is more than 1 meq/g, since hot water resistance, mechanical strength, dimensional stability and physical durability are deficient in some cases, this is not preferable.

Herein, the ion exchange capacity is a mole amount of a sulfonic acid group which has been introduced per unit dry weight of the block copolymer, polymer electrolyte material and polymer electrolyte membrane, and it is indicated that as this value is greater, a degree of sulfonation is higher. The ion exchange capacity can be measured by an elementary analysis method, a neutralization titration method or the like. The ion exchange capacity can be also calculated from an S/C ratio using the elementary analysis method, but it is difficult to measure the capacity when a sulfur source other than a sulfonic acid group is contained. Therefore, in the present invention, the ion exchange capacity is defined as a value obtained by the neutralization titration method. The polymer electrolyte material and polymer electrolyte membrane of the present invention encompass an aspect of being a composite including the block copolymer obtained from the present invention and other components as described later, and in this case, the ion exchange capacity is obtained based on a total amount of the composite.

A measurement example of neutralization titration is as follows. The measurements are carried out three or more times, and an average thereof is taken.

(1) Proton replacement is carried out, and moisture content on a surface of an electrolyte membrane which has been sufficiently washed with pure water is wiped and, thereafter, the membrane is dried in vacuum at 100° C. for 12 hrs or more, and a dry weight thereof is obtained.

(2) To the electrolyte is added 50 mL of a 5 wt % aqueous sodium sulfate solution, and this is allowed to stand for 12 hrs to perform ion exchange.

(3) Using a 0.01 mol/L aqueous sodium hydroxide solution, generated sulfuric acid is titrated. As an indicator, a commercially available 0.1 w/v % phenolphthalein solution for titration is added, and a point at which a solution turns faint red-violet is regarded as an end point.

(4) The ion exchange capacity is obtained by the following equation:

Ion exchange capacity (meq/g)=[concentration of aqueous sodium hydroxide solution (mmol/ml)× dropwise addition amount (ml)]/dry weight of sample (g).

A molecular weight of the thus obtained block copolymer obtained from the present invention is 50000 to 1000000, and preferably 100000 to 500000 as expressed by a weight average molecular weight in terms of polystyrene. When the molecular weight is less than 50000, any of mechanical strength, physical durability and solvent resistance such as occurrence of a crack on a molded membrane is insufficient in some cases. On the other hand, when the molecular weight is more than 1000000, there is a problem that solubility becomes insufficient, solution viscosity is high, and processability becomes deteriorated.

Number average molecular weights of the segment containing a sulfonic acid group (B1) and the segment not containing a sulfonic acid group (B2) relates to a domain size of a phase-separated structure, and from the view of a balance between proton conductivity under low humidification and physical durability, the number average molecular weight is more preferably 5000 or more, further preferably 10000 or more, and most preferably 15000 or more. Further, it is more preferably 50000 or less, further preferably 40000 or less, and most preferably 30000 or less.

Examples of a method of introducing a sulfonic acid group into the block copolymer obtained from the present invention include a method of polymerizing a monomer having a sulfonic acid group, and a method of introducing a sulfonic acid group by a polymer reaction.

As the method of polymerizing a monomer having a sulfonic acid group, a monomer having a sulfonic acid group in a repeating unit may be used. Such a method is described in, for example, Journal of Membrane Science, 197, 2002, p. 231-242. This method is easily applied industrially to control of an ion exchange capacity of a polymer, and is particularly preferable.

The method of introducing a sulfonic acid group by a polymer reaction will be described by way of an example. As a method of sulfonating an aromatic polymer, that is, a method of introducing a sulfonic acid group, the method described in, for example, Japanese Patent Laid-open Publication No. 2-16126 or Japanese Patent Laid-open Publication No. 2-208322 can be used. Specifically, for example, an aromatic polymer can be sulfonated by reacting the aromatic polymer with a sulfonating agent such as chlorosulfonic acid in a solvent such as chloroform and the like, or by reacting the aromatic polymer in concentrated sulfuric acid or fuming sulfuric acid. The sulfonating agent is not particularly limited as far as it sulfonates the aromatic polymer, and sulfur trioxide and the like in addition to the aforementioned sulfonating agent can be used. When the aromatic polymer is sulfonated by this method, a degree of sulfonation can be controlled by a use amount of the sulfonating agent, a reaction temperature and a reaction time.

The sulfonic acid group-containing polymer of the present invention is suitable as a polymer electrolyte material and, particularly, is suitably used as a polymer electrolyte molded product. In the present invention, the polymer electrolyte molded product means a molded product containing the polymer electrolyte material of the present invention. The polymer electrolyte molded product of the present invention can take a variety of forms depending on use application, such as plates, fibers, hollow yarns, particles, masses, micropores, coatings, and foams in addition to membranes (including films and film-like shapes). Since improvement in degree of free design of the polymer and improvement in various properties such as a mechanical property and solvent resistance can be performed, the sulfonic acid group-containing polymer can be applied to wide applications. Particularly, the sulfonic acid group-containing polymer is suitable when the polymer electrolyte molded product is membranes.

When the polymer electrolyte material of the present invention is used for a solid polymer fuel cell, it is suitably used in a polymer electrolyte membrane, an electrode catalyst layer and the like. Among them, the polymer electrolyte material is suitably used in the polymer electrolyte membrane. This is because when the polymer electrolyte material is used for a solid polymer fuel cell, usually, it is used as the polymer electrolyte membrane or the electrode catalyst layer binder in the state of a membrane.

The polymer electrolyte molded product of the present invention can be applied to a variety of applications. For example, the molded product can be applied to medical applications such as extracorporeal circulation column and artificial skin, filtration applications, ion exchange resin applications such as chlorine resistant reverse osmosis membranes, applications of various structural materials, electrochemical applications, humidification membranes, antifogging membranes, antistatic membranes, membranes for solar cells, and gas barrier materials. Alternatively, it is also suitable as artificial muscle, and actuator materials. Among them, it can be more preferably utilized in various electrochemical applications. Examples of the electrochemical application include a fuel cell, a redox flow cell, a water electrolysis device, a chloroalkali electrolysis device and the like and, among them, a fuel cell is most preferable.

Then, a making method for obtaining the polymer electrolyte molded product of the present invention will be specifically described.

For example, the polymer electrolyte molded product of the present invention is constituted of a block copolymer containing the segment not containing a sulfonic acid group (B2) containing the constituent unit having the formula (P2). Since the segment not containing a sulfonic acid group (B2) is a segment exhibiting crystallinity, the polymer electrolyte molded product can be made by, at least, molding a block copolymer precursor in which a protective group has been introduced into the segment not containing a sulfonic acid group (B2) and, thereafter, deprotecting at least a part of the protective group contained in the molded product. In the block copolymer, since there is a tendency that crystallization of the polymer with a domain formed thereon rather than a random polymer causes processability to be deteriorated, it is preferable that at least a protective group is introduced into the segment not containing a sulfonic acid group (B2) to improve processability, and it is preferable that a protective group is introduced into the segment containing a sulfonic acid group (B1) when processability is deteriorated.

Examples of the protective group used in the present invention include protective groups which are generally used in organic synthesis, and the protective group is a substituent which is temporarily introduced provided that it is removed at a later stage, and protects a functional group having high reactivity to make it inactive to a reaction thereafter, and the functional group can be deprotected after the reaction, and can be returned to the original functional group. That is, the protective group is paired with the functional group to be protected. For example, there is the case where a t-butyl group is used as a protective group for a hydroxyl group, but in the case where the same t-butyl group has been introduced into an alkylene chain, this is not referred to as a protective group. A reaction of introducing the protective group is referred to as a protection (reaction) and, a reaction of removing the protective group is referred to as a deprotection (reaction).

Such a protection reaction is described in detail in, for example, Theodora W. Greene, Protective Groups in Organic Synthesis, USA, John Wiley & Sons, Inc., 1981, and such a reaction can be preferably used. It can be appropriately selected in view of the reactivity and yield of the protection reaction and the deprotection reaction, stability of the state where the protective group is contained, the production cost and the like. A stage at which the protective group is introduced in a polymerization reaction may be a monomer stage, an oligomer stage or a polymer stage, and can be appropriately selected.

Examples of the protection reaction include a method of protecting/deprotecting a ketone site with a ketal site, and a method of protecting/deprotecting a ketone site as a hetero atom analogue of a ketal site, for example, thioketal. These methods are described in Chapter 4 in the Protective Groups in Organic Synthesis. Additionally, examples thereof include a method of protection/deprotection between sulfonic acid and a soluble ester derivative, a method of protection/deprotection by introduction of a t-butyl group as a soluble group into an aromatic ring, and de-t-butylation of the ring with an acid, and the like. However, the protective group is not limited thereto, and a group can be preferably used as far as it is a protective group. An aliphatic group, particularly, an aliphatic group containing a cyclic portion is preferably used as the protective group from the view of great steric hindrance, for the purpose of improving solubility to a solvent.

The protection reaction is further preferably a method of protecting/deprotecting a ketone site as a ketal site, or a method of protecting/deprotecting a ketone site as a hetero atom analogue of a ketal site, for example, thioketal from the view of reactivity and stability. In the polymer electrolyte material and polymer electrolyte membrane of the present invention, a constituent unit containing the protective group more preferably contains at least one kind of the following formulas (U1) and (U2):

[Chemical Formula 26]

(U1)

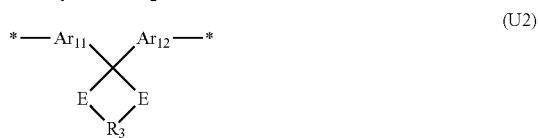
(U2)

In the formulas (U1) and (U2), $Ar_9$ to $Ar_{12}$ are divalent arylene groups, $R_1$ and $R_2$ are at least one of H and an alkyl group, $R_3$ is an alkylene group, E is O or S, and each of them may be two or more kinds of groups. Groups having the formulas (U1) and (U2) may be optionally substituted.

Among them, from the view of odor, reactivity, stability or the like of the compound, the method in which E is O in the formulas (U1) and (U2), that is, the method of protecting/deprotecting a ketone site as a ketal site is most preferable.

$R_1$ and $R_2$ in the formula (U1) are more preferably an alkyl group from the view of stability, further preferably an alkyl group having 1 to 6 carbon atoms, and most preferably an alkyl group having al to 3 carbon atoms. $R_3$ in the formula (P4) is more preferably an alkylene group having 1 to 7 carbon atoms from the view of stability, and most preferably an alkylene group having 1 to 4 carbon atoms. Specific examples of $R_3$ include, but are not limited to, —$CH_2CH_2$—, —$CH(CH_3)CH_2$—, —$CH(CH_3)CH(CH_3)$—, —$C(CH3)_2CH_2$—, —$C(CH_3)_2CH(CH_3)$—, —$C(CH_3)_2O(CH_3)_2$—, —$CH_2CH_2CH_2$—, —$CH_2C(CH_3)_2CH_2$— and the like.

Among the constituent units having the formulas (U1) and (U2), from the view of stability such as hydrolysis resistance, a constituent unit having at least the formula (U2) is more preferably used. Further, $R_3$ in the formula (U2) is preferably an alkylene group having 1 to 7 carbon atoms, that is, a group having $C_{n1}H_{2n1}$ (where n1 is an integer from 1 to 7), and from the view of stability and easiness of synthesis, it is most preferably at least one kind of —$CH_2CH_2$—, —$CH(CH_3)CH_2$—, or —$CH_2CH_2CH_2$—.

An organic group which is preferable as $Ar_9$ to $Ar_{12}$ in the formulas (U1) and (U2) is a phenylene group, a naphthylene group, or a biphenylene group. These groups may be optionally substituted. In the block copolymer obtained from the present invention, from the view of solubility and easiness of raw material availability, it is more preferable that both of $Ar_{11}$ and $Ar_{12}$ in the formula (U2) are a phenylene group, and it is most preferable that both of $Ar_{11}$ and $Ar_{12}$ are a p-phenylene group.

In the present invention, examples of a method of protecting a ketone site with ketal include methods of reacting a precursor compound having a ketone group with a monofunctional and/or bifunctional alcohol in the presence of an acid catalyst. For example, a ketal monomer can be made by reacting 4,4'-dihydroxybenzophenone which is a ketone precursor with a monofunctional and/or bifunctional alcohol in a solvent such as an aliphatic or aromatic hydrocarbon in the presence of an acid catalyst such as hydrogen bromide. The alcohol is an aliphatic alcohol having 1 to 20 carbon atoms. An improved method of making a ketal monomer to be used in the present invention includes reacting 4,4'-dihydroxybenzophenone which is a ketone precursor with a bifunctional alcohol in the presence of an alkyl orthoester and a solid catalyst.

In the present invention, a method of deprotecting at least a part of a ketone site protected with ketal to convert into a ketone site is not particularly limited. It is possible to perform the deprotection reaction in the presence of water and an acid under the heterogeneous or homogeneous condition, but from the view of mechanical strength, physical durability and solvent resistance, a method of performing acid treatment after molded into a membrane or the like is more preferable. Specifically, deprotection is possible by immersing a molded membrane in an aqueous hydrochloric acid solution or an aqueous sulfuric acid solution, and a concentration of the acid and a temperature of the aqueous solution can be appropriately selected.

A weight ratio of a necessary acidic aqueous solution relative to the polymer is preferably 1 to 100-fold, and a further large amount of water can be also used. The acid catalyst is preferably used at a concentration of 0.1 to 50% by weight of the water to be existed. Examples of the preferable acid catalyst include strong mineral acids such as hydrochloric acid, nitric acid, fluorosulfonic acid and sulfuric acid, and strong organic acids such as p-toluenesulfonic acid and trifluoromethanesulfonic acid. Amounts of the acid catalyst and excessive water, reaction pressure and the like can be appropriately selected depending on a membrane thickness of the polymer or the like.

For example, in the case of a membrane having a thickness of 25 μm, approximately all amount of the membrane can be easily deprotected by immersing the membrane in an acidic aqueous solution such as a 6N aqueous hydrochloric acid solution or a 5 wt % aqueous sulfuric acid solution, and heating at room temperature to 95° C. for 1 to 48 hrs. Alternatively, even when the membrane is immersed in a 1N aqueous hydrochloric acid solution at 25° C. for 24 hrs, substantially all of protective groups can be deprotected. However, the deprotection condition is not limited thereto, and deprotection may be performed by an acidic gas, an organic acid or heat treatment.

Specifically, for example, a precursor of a block copolymer containing the constituent units having the formula (U1) and (U2) can be synthesized by an aromatic nucleophilic substitution reaction with an aromatic active dihalide compound, using compounds having the following formulas (U1-1) and (U2-1), respectively, as a dihydric phenol compound. The constituent units having the formulas (U1) and (U2) may by derived from either of the dihydric phenol compound or the aromatic active dihalide compound, but it is more preferable to use a constituent unit derived from the dihydric phenol compound in view of reactivity of the monomer.

[Chemical Formula 27]

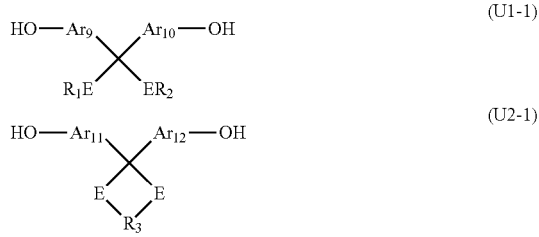

In the formulas (U1-1) and (U2-1), $Ar_9$ to $Ar_{12}$ are divalent arylene groups; $R_1$ and $R_2$ are at least one of H and an alkyl group; $R_3$ is an alkylene group; and E is O or S. The compounds having the formula (U1-1) and the formula (U2-1) may be optionally substituted.

Specific examples of the particularly preferable dihydric phenol compound used in the present invention include the compounds having the formulas (r1) to (r10), as well as derivatives derived from these dihydric phenol compounds. Among these dihydric phenol compounds, from the view of stability, the compounds having the formulas (r4) to (r10) are more preferable, the compounds having the formulas (r4), (r5) and (r9) are further preferable, and the compound having the formula (r4) is most preferable.

In oligomer synthesis by the aromatic nucleophilic substitution reaction which is performed in order to obtain the segment to be used in the present invention, a polymer can be obtained by reacting the monomer mixture in the presence of a basic compound. The polymerization can be performed in a temperature range of 0 to 350° C., and preferably at a temperature of 50 to 250° C. When the temperature is lower than 0° C., there is a tendency that the reaction does not proceed sufficiently, and when the temperature is higher than 350° C., there is a tendency that decomposition of the polymer begins to occur. The reaction can be also performed in the absence of a solvent, but is performed preferably in a solvent. Examples of the usable solvent include, but are not limited to, aprotic polar solvents such as N,N-dimethylacetamide, N,N-dimethylformamide, N-methyl-2-pyrrolidone, dimethyl sulfoxide, sulfolane, 1,3-dimethyl-2-imidazolidinone, hexamethylphosphonetriamide and the like, and a solvent which can be used as a stable solvent in the aromatic nucleophilic substitution reaction may be used. These organic solvents may be used alone, or as a mixture of two or more kinds.

Examples of the basic compound include sodium hydroxide, potassium hydroxide, sodium carbonate, potassium carbonate, sodium bicarbonate, potassium bicarbonate and the like, and a basic compound which can render aromatic diols an active phenoxide structure can be used without limitation thereto. In order to enhance nucleophilicity of phenoxide, a crown ether such as 18-crown-6 is suitably added. Sodium ions or potassium ions of a sulfonic acid group are coordinated with these crown ethers to improve solubility in an organic solvent in some cases, and these crown ethers can be preferably used.

In the aromatic nucleophilic substitution reaction, water is made as a byproduct in some cases. In this case, toluene or the like is allowed to exist in the reaction system regardless of polymerization solvents, and water can be also removed to outside of the system as an azeotrope. In a method of removing water to outside of the system, a water-absorbing agent such as molecular sieve can be also used.

An azeotropic agent used for removing reaction water or water which has been introduced during the reaction is generally any inactive compound which does not substantially hinder polymerization, is subjected to codistillation with water, and is boiled at between about 25° C. to about 250° C. A normal azeotropic agent includes benzene, toluene, xylene, chlorobenzene, methylene chloride, dichlorobenzene, trichlorobenzene, cyclohexanone and the like. Naturally, it is advantageous to select an azeotropic agent having a boiling point lower than that of the bipolar solvent used. The azeotropic agent is usually used, but when a high reaction temperature, for example, a temperature of 200° C. or higher is used, particularly, when an inert gas is continuously sprayed on the reaction mixture, it is not necessarily required. Generally, it is desirable to carry out the reaction under the inert atmosphere in the state where no oxygen is present.

When the aromatic nucleophilic substitution reaction is performed in a solvent, it is preferable to charge the monomer so that a concentration of the resulting polymer becomes 5 to 50 wt %. When the concentration is lower than 5 wt %, there is a tendency that a degree of polymerization is increased with difficulty. On the other hand, when the concentration is higher than 50 wt %, there is a tendency that viscosity of the reaction system becomes too high, and it becomes difficult to perform post treatment of a reaction product.

After completion of the polymerization reaction, the solvent is removed from the reaction solution by evaporation, and the residue is washed as necessary, thereby a desired polymer is obtained. Alternatively, the polymer can be also obtained by adding the reaction solution to a solvent having low solubility of a polymer, and high solubility of an inorganic salt made as a byproduct, thereby removing the inorganic salt, precipitating the polymer as a solid, and filtering the precipitate off. The recovered polymer is optionally washed with water, an alcohol or other solvents, and dried. When a desired molecular weight is obtained, a halide or phenoxide terminal group can be optionally reacted by introducing a phenoxide or halide terminal blocking agent which forms a stable terminal group.

In addition, a chemical structure of the sulfonic acid group-containing polymer of the present invention can be confirmed by S=O absorption at 1,030 to 1,045 $cm^{-1}$, and 1,160 to 1,190 $cm^{-1}$, C—O—C absorption at 1,130 to 1,250 $cm^{-1}$, C=O absorption at 1,640 to 1,660 $cm^{-1}$ or the like by infrared absorption spectrum, and a composition ratio thereof can be known by neutralization titration of a sulfonic acid group, or elementary analysis. A structure thereof can be confirmed by nuclear magnetic resonance spectrum ($^1$H-NMR), for example, from peaks of an aromatic proton at 6.8 to 8.0 ppm. A position of attachment of a sulfonic acid group and a way of arranging sulfonic acid groups can be confirmed by solution $^{13}$C-NMR or solid $^{13}$C-NMR.

Then, a specific method of synthesizing a block copolymer containing each one or more of the segment(s) containing a sulfonic acid group (B1), the segment(s) not containing a sulfonic acid group (B2), and the linker site(s) linking between the segments will be described. However, the present invention is not limited thereto.

The block copolymer obtained from the present invention can be made by synthesizing a block copolymer precursor and, thereafter, deprotecting at least a part of a protective group contained in the precursor.

Specific examples of a method of making the blocking copolymer obtained from the present invention and the blocking copolymer precursor include: a. a method of reacting a dihalide linker with any of a segment having the formula (S2) of a both ends hydroxyl group and/or a segment precursor, and a segment having the formula (P1) of a both ends hydroxyl group and/or a segment precursor and, thereafter, polymerizing alternately with another segment to make a block copolymer; b. a method of randomly polymerizing a segment having the formula (S2) of a both ends hydroxyl group and/or a segment precursor, and a segment having the formula (P1) of a both ends hydroxyl group and/or a segment precursor, and a dihalide linker to make a block copolymer; c. a method of making a block copolymer by the method described in a or b using an unsulfonated product of a segment having the formula (S2) and/or a segment precursor and, thereafter, selectively introducing a sulfonic acid group into an unsulfonated portion of the segment having the formula (S2) and/or the segment precursor; and d. a method of a combination of a to c, and the like. Among them, from the view of being capable of controlling a phase-separated domain size by alternate copolymerization, and making a chemically stable block copolymer, the method a is most preferable.

That is, it is more preferable that the method of making the block copolymer obtained from the present invention includes at least the following steps (1) to (4). By including these steps, improvement in mechanical strength and durability due to having high molecular weight can be attained, and by alternate introduction of both segments, a block copolymer excellent in low humidification proton conductivity, in which a phase-separated structure and a domain size are strictly controlled, can be obtained.

(1) A step of synthesizing the segment containing a sulfonic aid group (B1), which contains the constituent unit having the formula (S2), and/or a constituent unit which is to be a precursor of the constituent unit having the formula (S2), and has a both ends hydroxyl group;

(2) a step of synthesizing the segment not containing a sulfonic acid group (B2), which contains the constituent unit having the formula (P1), and/or a constituent unit which is to be a precursor of the constituent unit having the formula (P1), and has a both ends hydroxyl group;

(3) a step of introducing a linker site into a both ends hydroxyl group of the segment containing a sulfonic acid group (B1) or the segment not containing a sulfonic acid group (B2); and (4) a step of making a block copolymer and a block copolymer precursor by polymerizing a both ends linker site of the segment synthesized in (3), and a both ends hydroxyl group of the other segment.

In the method a, specific examples of the segment having the formula (S2) of a both ends hydroxyl group include the following formulas (H3-1) and (H3-2), respectively, and specific examples of the segment which is reacted with a dihalide linker include the following formulas (H3-3) and (H3-4), respectively. However, the present invention is not limited thereto.

[Chemical Formula 28]

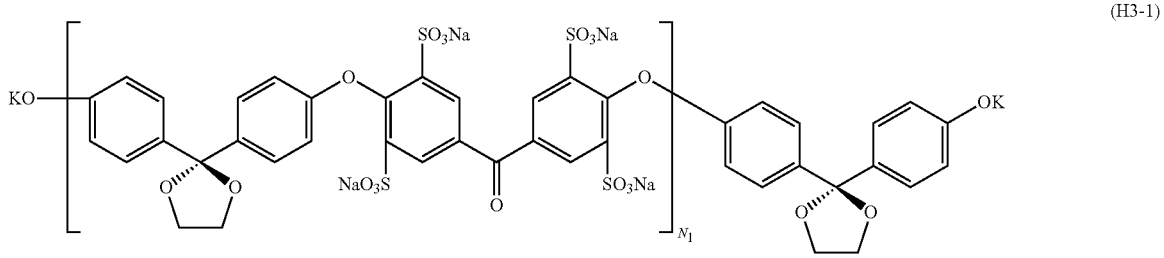

(H3-1)

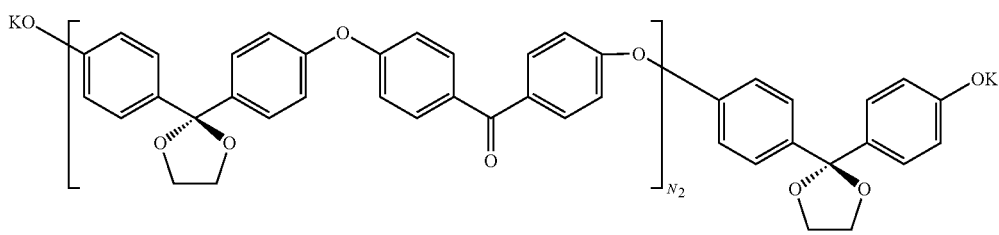

(H3-2)

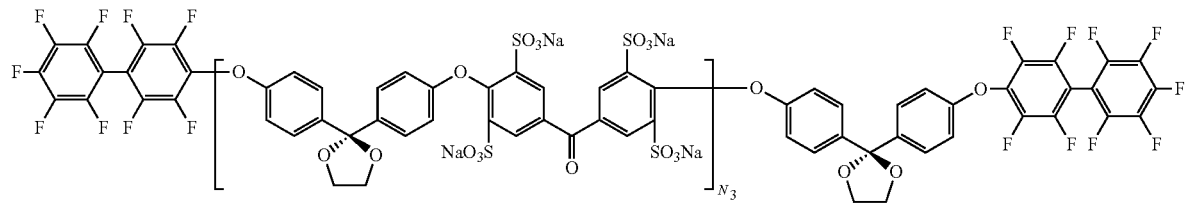

(H3-3)

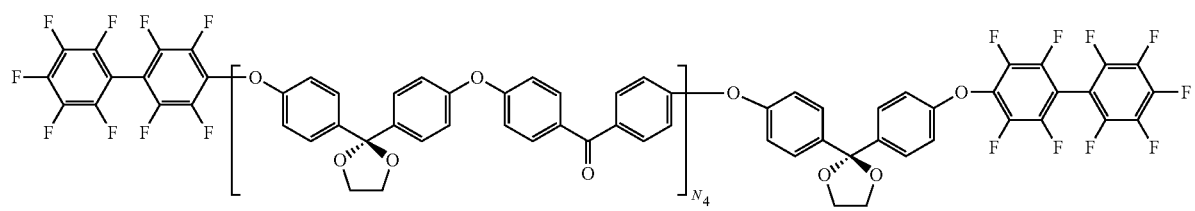

(H3-4)

In the formulas (H3-1) to (H3-4), a halogen atom is indicated by F, and an alkali metal is indicated by Na and K, but the halogen atom and the alkali metal can be used without limitation thereto. The aforementioned formulas are inserted for the purpose of assisting understanding of a reader, and do not necessarily exactly express a chemical structure, exact composition, and way of arrangement of polymerization components of the polymer, a position, number, molecular weight of a sulfonic acid group, and the like, and are not limited thereto.

Further, in the formulas (H3-1) to (H3-4), a ketal group as a protective group is introduced into every segment, but in the present invention, it may be enough that the protective group is introduced into a component having high crystallinity and low solubility, the protective group is not necessarily required in the segment containing a sulfonic acid group (B1) having the formulas (H3-1) and (H3-3), and from the view of durability and dimensional stability, a segment not having a protective group can be also preferably used.

In a block exemplified by the formula (H3-1), it is possible to synthesize an oligomer having a controlled molecular weight, by reacting a bisphenol component and an aromatic dihalide component at $(N_1+1):N_1$. This is also true in the formula (H3-2).

A reaction temperature of the block copolymerization using a linker is preferably under the warming condition at 140° C. or lower. It is more preferably 80° C. or higher and 120° C. or lower. By adopting 120° C. or lower as the reaction temperature, randomization of a polymer structure due to an ether exchange reaction during reaction can be sufficiently suppressed. On the other hand, if the temperature is set at 180° C. or higher, a polymer having a random polymer structure is obtained.

In the block copolymer obtained from the present invention, a cocontinuous phase-separated structure can be observed with transmission electron microscope observation. By controlling a phase-separated structure of the block copolymer, that is, aggregation state of the segment containing a sulfonic acid group (B1) and the segment not containing a sulfonic acid group, and a shape thereof, excellent proton conductivity can be realized even under the low humidification condition. It is possible to analyze the phase-separated structure with a transmission electron microscope (TEM), an atomic force microscope (AFM) or the like.

It is preferable that a polymer electrolyte membrane including the block copolymer obtained from the present invention is such that the phase-separated structure is cocontinuity-like structure or lamella-like structure. The phase-separated structure can be manifested in a polymer including two or more kinds of incompatible segments, for example, a polymer constituted of a block copolymer containing the segment containing a sulfonic acid group (B1) and the segment not containing a sulfonic acid group (B2), and a structural aspect thereof is roughly classified into four kinds of a cocontinuous structure (m1), a lamella structure (m2), a cylinder structure (m3), and a sea island structure (m4) (FIG. 1).

Such a phase-separated structure is described in, for example, Annual Review of Physical Chemistry, 41, 1990, p. 525 or the like. By controlling a high order structure or shape of these segment containing a sulfonic acid group (B1) and segment not containing a sulfonic acid group (B2), it becomes possible to realize excellent proton conductivity even under the low humidification and low temperature conditions, and particularly, when a structure thereof is (m1) or (m2) of FIG. 1, that is, the cocontinuous or lamella structure, a continuous proton conductive channel is formed and, at the same time, due to crystallinity of a domain including the segment not containing a sulfonic acid group (B2), it becomes possible to realize a polymer electrolyte membrane which is not only excellent in proton conductivity but also has extremely excellent fuel blocking property, solvent resistance, mechanical strength and physical durability, and thus this is preferable.

On the other hand, even in the case of (m3) or (m4) of FIG. 1, that is, the cylinder structure or the sea island structure, it is considered that a continuous proton conductive channel can be also formed. However, both structures are structures which can be constructed when a ratio of the segment containing a sulfonic acid group is relatively small based on a ratio of the segment not containing a sulfonic acid group, or when a ratio of the segment not containing a sulfonic acid group is relatively small based on a ratio of the segment containing a sulfonic acid group, and in the case of the former, an amount of the sulfonic acid group bearing proton conduction is absolutely decreased and, particularly, in the sea island structure, a continuous proton conductive channel itself is not formed, and thus proton conductivity is inferior and, in the case of the latter, proton conductivity is excellent but an amount of a crystalline nonionic domain is small, and thus a fuel blocking property, solvent resistance, mechanical strength and physical durability are inferior, and the effect of the present invention is not sufficiently obtained.

The polymer electrolyte membrane including the block copolymer obtained from the present invention is preferably a polymer electrolyte membrane in which a phase-separated structure is observed when observed with TEM at magnification of 50000, and an average interlayer distance or an average interparticle distance measured by image processing is 8 nm or more and 100 nm or less. Inter alia, an average interlayer distance or an average interparticle distance is more preferably 10 nm or more and 50 nm or less, and most preferably 15 nm or more and 30 nm or less. When the phase-separated structure is not observed with a transmission electron microscope, or the average interlayer distance or the average interparticle distance is less than 8 nm, since continuity of an ion channel is deficient, and conductivity is deficient in some cases, this is not preferable. In addition, when the interlayer distance is more than 5000 nm, mechanical strength and dimensional stability become deteriorated in some cases, and this is not preferable.

The block copolymer obtained from the present invention is characterized in that it has crystallinity while having the phase-separated structure, and the crystallinity is recognized by differential scanning calorimetry (DSC) or wide angle X-ray diffraction. That is, the block copolymer is a block copolymer having a crystallization heat amount measured by differential scanning calorimetry of 0.1 J/g or more, or a crystallinity measured by wide angle X-ray diffraction of 0.5% or more.

In the present invention, "having crystallinity" means that a polymer can be crystallized when a temperature is raised, has nature of being crystallizable, or has been already crystallized. A non-crystalline polymer means a polymer which is not a crystalline polymer, or a polymer, crystallization of which does not substantially proceed. Therefore, even in the case where a polymer is a crystalline polymer, but crystallization does not sufficiently proceed, it is in the non-crystalline state as the state of the polymer in some cases.

A method of molding the polymer electrolyte material of the present invention into the polymer electrolyte membrane is not particularly limited, and a method of making a membrane from the solution state or a method of making a membrane from the molten state, at a stage having a protective group such as ketal and the like is possible. In the former, for example, a method of making a membrane by dissolving the polymer electrolyte material in a solvent such as N-methyl-2-pyrrolidone, casting-coating the solution on a glass plate or the like, and removing the solvent can be exemplified.

The solvent used in making a membrane may be enough as far as it is a solvent which dissolves the polymer electrolyte material and, thereafter, can be removed, and aprotic polar solvents such as N,N-dimethylacetamide, N,N-dimethylformamide, N-methyl-2-pyrrolidone, dimethyl sulfoxide, sulfolane, 1,3-dimethyl-2-imidazolidinone, and hexamethylphosphonetriamide, ester solvents such as γ-butyrolactone and butyl acetate, carbonate solvents such as ethylene carbonate and propylene carbonate, alkylene glycol monoalkyl ethers such as ethylene glycol monomethyl ether, ethylene glycol monoethyl ether, propylene glycol monomethyl ether, and propylene glycol monoethyl ether, or alcohol solvents such as isopropanol, water and a mixture thereof are suitably used, and aprotic polar solvents have highest solubility, and are preferable. In addition, in order to enhance solubility of the segment containing a sulfonic acid group (B1), it is also suitable to add a crown ether such as 18-crown-6.

In the present invention, when the block copolymer is used, selection of the solvent is important for the phase-separated structure, and use of an aprotic polar solvent and a solvent having low polarity as a mixture is also a suitable method.

It is a preferable method for obtaining a tough membrane that a polymer solution which has been adjusted to a necessary solid matter concentration is subjected to filtration under normal pressure or filtration under pressure to remove foreign matters existing in the polymer electrolyte solution. A Filter material used herein is not particularly limited, and a glass filter and a metallic filter are suitable. At the time of filtration, The smallest pore diameter of a filter through which the polymer solution passes is preferably 1 μm or less. When filtration is not performed, it results in allowing contamination of foreign matters to cause membrane breakage or insufficient durability and, therefore, this is not preferable.

Then, it is preferable to heat-treat at least a part of a sulfonic acid group in the state of a metal salt in the resulting polymer electrolyte membrane. When the polymer electrolyte material to be used is polymerized in the state of a metal salt at the time of polymerization, it is preferable to make the material into a membrane as it is, and to heat-treat the membrane. A metal of the metal salt may be enough as far as it is a metal which can form a salt with sulfonic acid, and from the view of price and environmental load, Li, Na, K, Rb, Cs, Mg, Ca, Sr, Ba, Ti, V, Mn, Fe, Co, Ni, Cu, Zn, Zr, Mo, W and the like are preferable and, among them, Li, Na, K, Ca, Sr and Ba are more preferable, and Li, Na and K are further preferable.

A temperature for this heat treatment is preferably 80 to 350° C., further preferably 100 to 200° C., and particularly preferably 120 to 150° C. A heat treatment hour is preferably 10 seconds to 12 hrs, further preferably 30 seconds to 6 hrs, and particularly preferably 1 minute to 1 hr. When the heat treatment temperature is too low, mechanical strength and physical durability are deficient in some cases. On the other hand, when the heat treatment temperature is too high, chemical decomposition of the membrane material proceeds in some cases. When the heat treatment time is shorter than 10 seconds, the effect of the heat treatment is deficient. On the other hand, when the heat treatment time is longer than 12 hrs, deterioration of the membrane material easily occurs. The polymer electrolyte membrane obtained by heat treatment can be subjected to proton substitution, if necessary, by immersing it in an acidic aqueous solution. By molding through this method, the polymer electrolyte membrane of the present invention can attain both of proton conductivity and physical durability at a better balance.

A method of converting the polymer electrolyte material used in the present invention into a membrane is to manufacture a membrane constituted of the polymer electrolyte material by the aforementioned procedure, thereafter, deprotect at least a part of a ketone site protected with ketal into a ketone site. According to this method, it is possible to make a membrane in solution of a block copolymer containing a block not containing a sulfonic acid group poor in solubility, and proton conductivity, mechanical strength and physical durability can be attained.

The polymer electrolyte membrane of the present invention having a thickness of preferably 1 to 2000 µm is suitably used. In order to obtain mechanical strength and physical durability which are suitable for practical use, a thickness having more than 1 µm is more preferable, and in order to reduce membrane resistance, that is, improve electric power generation performance, a thickness having smaller than 2000 µm is preferable. A further preferable range of such a membrane thickness is 3 to 50 µm, and particularly preferably 10 to 30 µm. The membrane thickness can be controlled by a solution concentration or a thickness of coating on a substrate.

Further, usual additives such as a crystallization nucleating agent, a plasticizer, a stabilizer, an antioxidant and a releasing agent, which are used in polymer compounds, can be added to the polymer electrolyte membrane obtained by the present invention in a range not contrary to the object of the present invention.

The polymer electrolyte membrane obtained by the present invention may contain various polymers, elastomers, fillers, fine particles, and various additives in such a range that the aforementioned various properties are not adversely affected, for the purpose of improving mechanical strength, heat stability and processability. The polymer electrolyte membrane may be reinforced with microporous membranes, non-woven fabrics, meshes or the like.

A method of joining the polymer electrolyte membrane and an electrode when the polymer electrolyte membrane is used as a fuel cell is not particularly limited, and known methods (e.g., chemical plating method described in Electrochemistry, 1985, 53, p. 269, method of heat press joining gas diffusion electrode described in Electrochemical Science and Technology edited by J. Electrochem. Soc., 1988, 135, 9, p. 2209, etc.) can be applied.

Solid polymer fuel cells use a hydrogen ion conductive polymer electrolyte membrane as an electrolyte membrane, and have a structure in which a catalyst layer, an electrode substrate and a separator are sequentially laminated on both sides thereof. Of these, an electrolyte membrane in which a catalyst layer is laminated on both sides thereof (i.e., layer constitution of catalyst layer/electrolyte membrane/catalyst layer) is referred to as a catalyst coated membrane (CCM) and, further, an electrolyte membrane in which a catalyst layer and a gas diffusion substrate are sequentially laminated on both sides thereof (i.e., layer constitution of gas diffusion substrate/catalyst layer/electrolyte membrane/catalyst layer/gas diffusion substrate) is referred to as a electrode-electrolyte membrane assembly (MEA).

As a method of making this catalyst coated membrane, a coating manner of coating a catalyst layer paste composition for forming a catalyst layer on an electrolyte membrane surface, followed by drying is generally performed. However, in this coating manner, a problem arises such that the electrolyte membrane is swollen and deformed by a solvent such as water or an alcohol contained in the paste, and it is difficult to form a desired catalyst layer on the electrolyte membrane surface. Further, a problem also arises such that since the electrolyte membrane is also exposed to a high temperature at a drying step, the electrolyte membrane causes thermal expansion or the like, and is deformed. In order to overcome this problem, a method of preparing only a catalyst layer on a substrate in advance, and transferring this catalyst layer, thereby laminating the catalyst layer on an electrolyte membrane (transferring method) has been proposed (e.g., Japanese Patent Laid-open Publication No. 2009-9910).

Since the polymer electrolyte membrane obtained by the present invention is tough and excellent in solvent resistance due to crystallinity, it can be particularly suitably used as the catalyst coated membrane in any case of the coating manner and the transferring method.

When MEA is manufactured by heat pressing, a temperature and pressure therefor may be appropriately selected depending on a thickness and water content of the electrolyte membrane, the catalyst layer and the electrode substrate. In the present invention, conjugation by pressing is also possible in the state where the electrolyte membrane is dried, or water is absorbed. Specific examples of a pressing method include roll pressing defining pressure and clearance, and plate pressing defining pressure, and from the view of industrial productivity and suppression of thermal decomposition of a polymer material having a sulfonic acid group, the pressing method is performed preferably in a range of 0° C. to 250° C. From the view of protection of the electrolyte membrane and the electrode, pressurization is preferably as weak as possible, and in the case of the plate pressing, a pressure of 10 MPa or lower is preferable, and lamination of the electrode and the electrolyte membrane to form a fuel cell without performing conjugation by heat pressing step is also one of preferable options from the view of preventing short circuit between anode and cathode electrodes. In the case of this method, there is a tendency that when electric power generation is repeated as a fuel cell, deterioration of the electrolyte membrane, which is presumed to be a cause of short circuit location, is suppressed, and durability as a fuel cell becomes good.

Further, applications of a solid polymer fuel cell using the polymer electrolyte material and polymer electrolyte membrane of the present invention are not particularly limited, and are preferably electric power supply sources for a moving body. Particularly, the solid polymer fuel cell is preferably used as a substitute for a previous primary cell or secondary cell such as an electric power supply source and a stationary electric power generator of potable devices including a potable phone, a personal computer, PDA, a television, a radio, a music player, a game machine, a head set, a DVD player and the like; human-type and animal type various robots for industry; electric appliances including a cordless cleaner and the like; toys; and moving bodies including vehicles, for example, an electric bicycle, a motorcycle, an automobile, a bus, and a truck; ships and trains; or as a hybrid electric power supply with the previous primary cell or secondary cell.

EXAMPLES

The present invention will be described in more detail by way of Examples, but the present invention is not limited thereto. In addition, conditions for measuring various physical properties are as follows.

(1) Ion Exchange Capacity

An ion exchange capacity per unit gram (meq/g) was calculated by neutralization titration.

(2) Proton Conductivity

A membrane-like sample was immersed in pure water at 25° C. for 24 hrs, thereafter, was kept in a constant temperature and humidity tank at 80° C. and a relative humidity of 25 to 95% at each step for 30 minutes, and proton productivity was measured by a constant potential alternating current impedance method.

Using an electrochemistry measurement system manufactured by Solartron (Solartron 1287 Electrochemical Interface and Solartron 1255B Frequency Response Analyzer) as a measurement device, constant potential impedance measurement was performed by a two-terminal method to obtain proton conductivity. An alternating current amplitude was set to 50 mV. As a sample, a membrane having a width of 10 mm and a length of 50 mm was used. A measurement jig was made of a phenolic resin, and a measurement portion was released. As an electrode, platinum plates (thickness 100 μm, 2 plates) were used. The electrodes were arranged on a front side and rear side of the sample membrane at an interelectrode distance of 10 mm so as to be parallel with each other and be orthogonal with the longitudinal direction of the sample membrane.

(3) Number Average Molecular Weight, Weight Average Molecular Weight

A number average molecular weight and weight average molecular weight of a polymer were measured by GPC. Using HLC-8022GPC manufactured by TOSOH CORPORATION as an integrated apparatus of an ultraviolet detector and a differential refractometer, and two columns of TSK gel SuperHM-H (internal diameter 6.0 mm, length 15 cm) manufactured by TOSOH CORPORATION as a GPC column, measurement was performed at a sample concentration of 0.1 wt %, a flow rate of 0.2 mL/minute and a temperature of 40° C. in a N-methyl-2-pyrrolidone solvent (N-methyl-2-pyrrolidone solvent containing 10 mmol/L lithium bromide), to obtain a number average molecular weight and a weight average molecular weight in terms of standard polystyrene.

(4) Membrane Thickness

A membrane thickness was measured using Model ID-C112 manufactured by Mitutoyo Corporation set in a granite comparator stand BSG-20 manufactured by Mitutoyo Corporation.

(5) Observation of Phase-Separated Structure with Transmission Electron Microscope (TEM)

A sample piece was immersed in a 2 wt % aqueous lead acetate solution as a dyeing agent, and allowed to stand at 25° C. for 24 hrs. The dyeing-treated sample was taken out, embedded with a visible curable resin, and irradiated with visible light for 30 seconds to fix the sample.

A 100 nm thin section was cut at room temperature using an ultramicrotome, and the resulting thin section was recovered on a Cu grid, and subjected to TEM observation. The observation was performed at an acceleration voltage of 100 kV, and photographing was performed at a photograph magnification of ×8,000, ×20,000, or ×100,000. As an instrument, TEM H7100FA (manufactured by Hitachi Ltd.) was used.

(6) Purity Analysis of Bisphenol Compound

Quantitative analysis was performed by gas chromatography (GC) under the following conditions.

Column: DB-5 (manufactured by J & W) L=30 m φ=0.53 mm D=1.50 μm
Carrier: Helium (linear velocity=35.0 cm/second)
Analysis Conditions
Inj. temp. 300° C.
Detct. temp. 320° C.
Oven 50° C.×1 min
Rate 10° C./min
Final 300° C.×15 min
SP ratio 50:1

(7) Hot Water Resistance

Hot water resistance of the electrolyte membrane was evaluated by measuring a rate of dimensional change in hot water at 95° C. The electrolyte membrane was cut into a strip of a length of about 5 cm and a width of about 1 cm, and immersed in water at 25° C. for 24 hrs, and a length (L1) was measured with a vernier caliper. After the electrolyte membrane was immersed in hot water at 95° C. for 8 hrs, a length (L2) was measured again with a vernier caliper, and a magnitude of dimensional change thereof was observed visually.

(8) Nuclear Magnetic Resonance Spectrum (NMR)

Under the following measuring conditions, measurement of $^1$H-NMR was performed, and structural confirmation, and confirmation of a constituent unit containing a sulfonic acid group were performed.

Apparatus: EX-270 manufactured by JEOL Ltd.
Resonance frequency: 270 MHz ($^1$H-NMR)
Measurement temperature: Room temperature
Dissolving solvent: DMSO-d6
Internal standard substance: TMS (0 ppm)
Integration time: 16 times Under the following measurement conditions, measurement of solid $^{13}$C-CP/MAS spectrum was performed, and the presence or absence of a remaining ketal group was confirmed.

Apparatus: CMX-300 Infinity manufactured by Chemagnetics
Measurement temperature: Room temperature
Internal standard substance: Si rubber (1.56 ppm)
Measurement nucleus: 75.188829 MHz
Pulse width: 90° pulse, 4.5 μsec
Pulse repeating time: ACQTM=0.03413 sec, PD=9 sec
Spectral width: 30.003 kHz
Sample rotation: 7 kHz
Contact time: 4 msec Synthesis Example 1

Synthesis of 2,2-bis(4-hydroxyphenyl)-1,3-dioxolane (K-DHBP) Having Following Formula (G1)

[Chemical Formula 29]

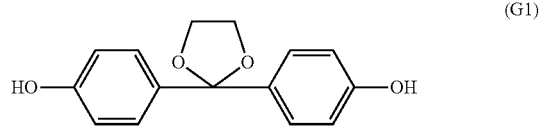

(G1)

A 500 ml flask equipped with a stirrer, a thermometer and a distilling tube was charged with 49.5 g of 4,4'-dihydroxybenzophenone, 134 g of ethylene glycol, 96.9 g of trimethyl orthoformate and 0.50 g of p-toluenesulfonic acid monohydrate, and the materials were dissolved. Thereafter, the mixture was stirred for 2 hrs while a temperature was kept at 78 to 82° C. Further, an internal temperature was gradually raised to 120° C., and the mixture was heated until distillation of methyl formate, methanol and trimethyl orthoformate was completely ceased. After cooled to room temperature, the reaction solution was diluted with ethyl acetate, the organic layer was washed with 100 ml of a 5% aqueous potassium carbonate solution, the layers were separated, and the solvent was distilled off. To the residue was added 80 ml of dichloromethane to precipitate a crystal, which was filtered and dried to obtain 52.0 g of 2,2-bis(4-hydroxyphenyl)-1,3-dioxolane. This crystal was subjected to GC-analysis, and was found to be 99.8% of 2,2-bis(4-hydroxyphenyl)-1,3-dioxolane and 0.2% of 4,4'-dihydroxybenzophenone.

Synthesis Example 2

Synthesis of disodium 3,3'-disulfonate-4,4'-difluorobenzophenone Having Following Formula (H1)

[Chemical Formula 30]

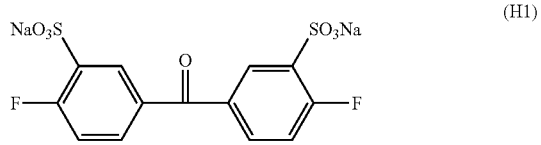

(H1)

109.1 g of 4,4'-difluorobenzophenone (Aldrich reagent) was reacted in 150 mL of fuming sulfuric acid (50% $SO_3$) (Wako Pure Chemical Industries, Ltd. reagent) at 100° C. for 10 hrs. Thereafter, the reaction was gradually placed into a large amount of water, this was neutralized with NaOH, and then 200 g of sodium chloride was added to precipitate a synthesized product. The resulting precipitate was filtered off, and recrystallized with an aqueous ethanol solution to obtain disodium 3,3'-disulfonate-4,4'-difluorobenzophenone having the formula (H1). It had a purity of 99.3%. The structure was confirmed by $^1$H-NMR. Impurities were quantitatively analyzed by capillary electrophoresis (organic substance) and ion chromatography (inorganic substance).

Example 1

Synthesis of tetrasodium 3,5,3',5'-tetrasulfonate-4,4'-difluorobenzophenone Having Formula (G2)

To a 1000 mL 3-neck flask equipped with a stirrer and a concentrator were added 109.1 g of 4,4'-difluorobenzophenone (Aldrich reagent), and 210 mL of fuming sulfuric acid (60% $SO_3$) (Aldrich reagent), followed by a reaction at 180° C. for 24 hrs while nitrogen was vigorously flown to a nitrogen introducing tube connected to an upper part of the concentrator, and a bubbler directed to the outside of the system. At this time, by vigorously flowing nitrogen, evaporation of sulfur trioxide was suppressed. After the reaction was gradually placed into a large amount of water, and neutralized with NaOH, sodium sulfate was removed by precipitating with ethanol three times, to obtain a sulfonic acid group-containing aromatic compound having the following formula (G2). The structure was confirmed by $^1$H-NMR. A raw material, a disulfonated product and a trisulfonated product were not entirely recognized, and a tetrasulfonated product at high purity could be obtained.

[Chemical Formula 31]

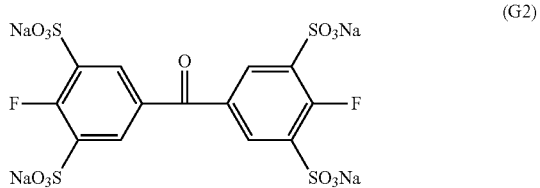

(G2)

Comparative Example 1

Synthesis of the formula (G2) was tried by the method described in Japanese Patent Laid-open Publication No. 2007-84739. That is, 109.1 g of 4,4'-difluorobenzophenone, 150 mL of fuming sulfuric acid (50% $SO_3$) and 50 g of sulfur trioxide were reacted at 180° C. for 24 hrs. Thereafter, the reaction was gradually placed into a large amount of water, this was neutralized with NaOH, and then 200 g of sodium chloride was added to precipitate a synthesized product. Purification was performed by filtering the resulting precipitate off.

A disulfonated product of 4,4'-difluorobenzophenone was a main product, and small amounts of a trisulfonated product and tetrasulfonated product were confirmed. As described in Japanese Patent Laid-open Publication No. 2007-84739, only a mixture of a disulfonated product, trisulfonated product and tetrasulfonated product was obtained, a mole amount relative to bisphenol could not be strictly adapted, and it was difficult to obtain a high-molecular product using this monomer mixture.

Example 2

Synthesis of tetrasodium 3,5,3',5'-tetrasulfonate-4,4'-dichlorodiphenyl sulfone Having Following Formula (G3)

To a 1000 mL 3-neck flask equipped with a stirrer and a concentrator were added 143.6 g of 4,4'-dichlorodiphenyl sulfone (Aldrich reagent), and 210 mL of fuming sulfuric acid (60% $SO_3$) (Aldrich reagent), followed by a reaction at 200° C. for 24 hrs while nitrogen was vigorously flown to a nitrogen introducing tube connected to an upper part of the concentrator, and a bubbler directed to the outside of the system. At this time, by vigorously flowing nitrogen, evaporation of sulfur trioxide was suppressed. After the reaction was gradually placed into a large amount of water, and neutralized with NaOH, sodium sulfate was removed by precipitating with ethanol three times, to obtain a sulfonic acid group-containing aromatic compound having the following formula (G3). The structure was confirmed by $^1$H-NMR. A raw material, a disulfonated product and a trisulfonated product were not entirely recognized, and a tetrasulfonated product at high purity could be obtained.

[Chemical Formula 32]

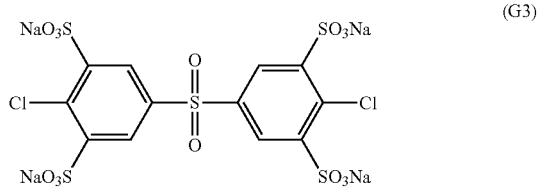

(G3)

Example 3

Synthesis of tetrasodium 3,5,3',5'-tetrasulfonate-4, 4'-difluorobiphenyl Having Following Formula (G4)

To a 1000 mL 3-neck flask equipped with a stirrer and a concentrator were added 95.0 g of 4,4'-difluorobiphenyl (Aldrich reagent), and 210 mL of fuming sulfuric acid (60% $SO_3$) (Aldrich reagent), followed by a reaction at 160° C. for 24 hrs while nitrogen was vigorously flown to a nitrogen introducing tube connected to an upper part of the concentrator, and a bubbler directed to the outside of the system. At this time, by vigorously flowing nitrogen, evaporation of sulfur trioxide was suppressed. After the reaction was gradually placed into a large amount of water, and neutralized with NaOH, sodium sulfate was removed by precipitating with ethanol three times, to obtain a sulfonic acid group-containing aromatic compound having the following formula (G4). The structure was confirmed by $^1$H-NMR. A raw material, a disulfonated product and a trisulfonated product were not entirely recognized, and a tetrasulfonated product at high purity could be obtained.

[Chemical Formula 33]

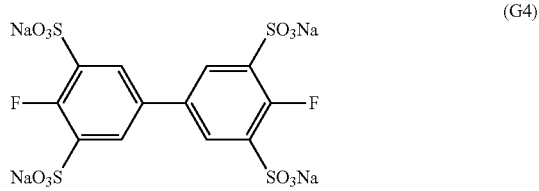

(G4)

Example 4

Sulfonic Acid Group-Containing Polymer Having Following Formula (G5)

In the formula, * represents that the right end of the upper formula and the left end of the lower formula are bonded at that position. Hereinafter, * indicates the same.

In a 500 mL 3-neck flask equipped with a stirrer, a nitrogen introducing tube and a Dean-Stark trap, using 5.5 g of potassium carbonate, 5.2 g of the 2,2-bis(4-hydroxyphenyl)-1,3-dioxane mixture obtained in Synthesis Example 1, 2.2 g of 4,4'-difluorobenzophenone, 6.3 g of the sulfonic acid group-containing aromatic compound having the formula (G2), which was obtained in Example 1, and 2.6 g of 18-crown-6-ether, dehydration was performed at 180° C. in 50 mL of N-methylpyrrolidone (NMP)/40 mL of toluene, thereafter, a temperature was raised to remove the toluene, and polymerization was performed at 240° C. for 3 hrs. Purification was performed by re-precipitation with a large amount of water, to obtain a precursor polymer having a ketal group. The polymer had a weight average molecular weight of 220000.

A 25 wt % N-methylpyrrolidone (NMP) solution in which the resulting precursor polymer had been dissolved was casting-coated on a glass substrate, and this was dried at 100° C. for 4 hrs, and heat-treated at 150° C. for 30 minutes under nitrogen to obtain a membrane. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G5) was obtained.

The sulfonic acid group-containing polymer having the formula (G5) contained 100 mol % of the constituent unit having the formula (S1), among constituent units containing a sulfonic acid group.

The resulting membrane had a thickness of 25 μm, and an ion exchange capacity obtained from neutralization titration of 3.4 meq/g, and remaining of a ketal group was not recognized. The membrane was a free standing membrane, and was a membrane which was transparent and uniform visually. The membrane had a proton conductivity of 410 mS/cm at 80° C. and a relative humidity of 85%, and had that of 1 mS/cm at 80° C. and a relative humidity of 25%, and it was excellent in low humidification proton conductivity.

[Chemical Formula 34]

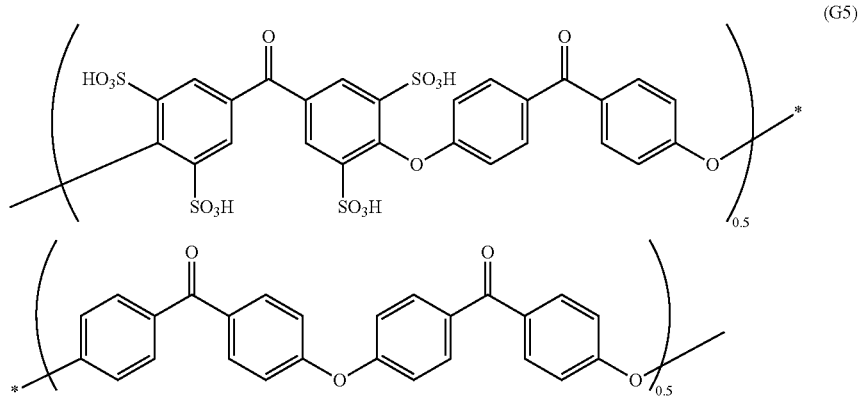

(G5)

Example 5

Sulfonic Acid Group-Containing Polymer Having Following Formula (G6)

[Chemical Formula 35]

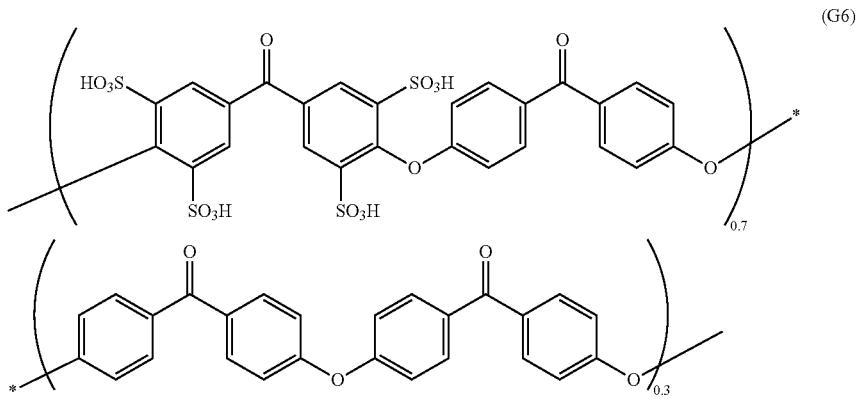

In a 500 mL 3-neck flask equipped with a stirrer, a nitrogen introducing tube and a Dean-Stark trap, using 3.9 g of potassium carbonate, 5.2 g of the 2,2-bis(4-hydroxyphenyl)-1,3-dioxane mixture obtained in Synthesis Example 1, 1.3 g of 4,4'-difluorobenzophenone, 8.8 g of the sulfonic acid group-containing aromatic compound having the formula (G2), which was obtained in Example 1, and 3.6 g of 18-crown-6-ether, dehydration was performed at 180° C. in 50 mL of N-methylpyrrolidone (NMP)/40 mL of toluene, a temperature was raised to remove the toluene, and polymerization was performed at 240° C. for 3 hrs. Purification was performed by re-precipitation with a large amount of water, to obtain a precursor polymer having a ketal group. The polymer had a weight average molecular weight of 200000.

A 25 wt % N-methylpyrrolidone (NMP) solution in which the resulting precursor polymer had been dissolved was casting-coated on a glass substrate, and this was dried at 100° C. for 4 hrs, and heat-treated at 150° C. for 30 minutes under nitrogen to obtain a membrane. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G6) was obtained.

The sulfonic acid group-containing polymer having the formula (G6) contained 100 mol % of the constituent unit having the formula (S1), among constituent units containing a sulfonic acid group.

The resulting membrane had a thickness of 25 μm, and an ion exchange capacity obtained from neutralization titration of 4.2 meq/g, and remaining of a ketal group was not recognized. The membrane was a free standing membrane, and was a membrane which was transparent and uniform visually. The membrane had a proton conductivity of 700 mS/cm at 80° C. and a relative humidity of 85%, and had that of 1.5 mS/cm at 80° C. and a relative humidity of 25%, and it was excellent in low humidification proton conductivity.

Example 6

Sulfonic Acid Group-Containing Polymer Having Following Formula (G7)

[Chemical Formula 36]

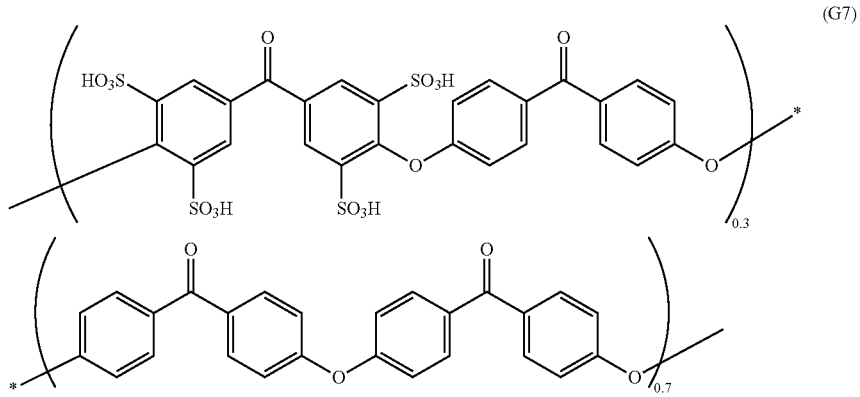

In a 500 mL 3-neck flask equipped with a stirrer, a nitrogen introducing tube and a Dean-Stark trap, using 3.3 g of potassium carbonate, 5.2 g of the 2,2-bis(4-hydroxyphenyl)-1,3-dioxane mixture obtained in Synthesis Example 1, 3.1 g of 4,4'-difluorobenzophenone, 3.8 g of the sulfonic acid group-containing aromatic compound having the formula (G2), which was obtained in Example 1, and 1.6 g of 18-crown-6-ether, dehydration was performed at 180° C. in 50 mL of N-methylpyrrolidone (NMP)/40 mL of toluene, thereafter, a temperature was raised to remove the toluene, and polymerization was performed at 240° C. for 3 hrs. Purification was performed by re-precipitation with a large amount of water, to obtain a precursor polymer having a ketal group. The polymer had a weight average molecular weight of 280000.

A 25 wt % N-methylpyrrolidone (NMP) solution in which the resulting precursor polymer had been dissolved was casting-coated on a glass substrate, and this was dried at 100° C. for 4 hrs, and heat-treated at 150° C. for 30 minutes under nitrogen to obtain a membrane. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G7) was obtained.

The sulfonic acid group-containing polymer having the formula (G7) contained 100 mol % of the constituent unit having the formula (S1), among constituent units containing a sulfonic acid group.

The resulting membrane had a thickness of 25 μm, and an ion exchange capacity obtained from neutralization titration of 2.4 meq/g, and remaining of a ketal group was not recognized. The membrane was an extremely tough free standing membrane, and was a membrane which was transparent and uniform visually. The membrane had a proton conductivity of 350 mS/cm at 80° C. and a relative humidity of 85%, and had that of 0.5 mS/cm at 80° C. and a relative humidity of 25%, and it was excellent in low humidification proton conductivity.

Example 7

Sulfonic Acid Group-Containing Polymer Having Following Formula (G8)

[Chemical Formula 37]

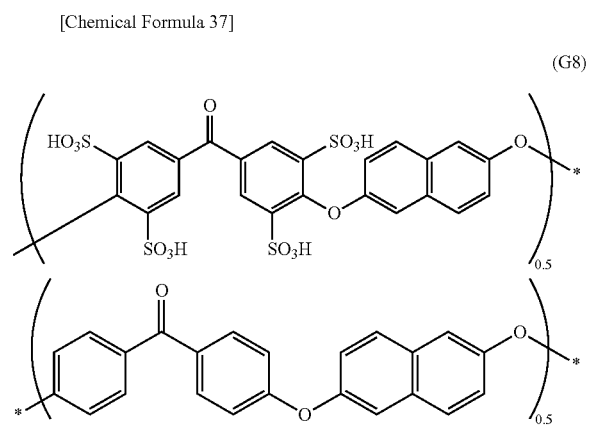

(G8)

According to the same method as that of Example 4 except that 3.2 g of 2,6-dihydroxynaphthalene was placed in place of the 2,2-bis(4-hydroxyphenyl)-1,3-dioxane mixture obtained in Synthesis Example 1, polymerization was performed to obtain a polymer containing a sodium sulfonate group. The polymer had a weight average molecular weight of 170000.

The resulting polymer was made into a membrane according to the same method as that of Example 4. Solubility of a sulfonic acid group-containing polymer before molding was good. After the membrane was immersed in a 10 wt % aqueous sulfuric acid solution at 25° C. for 24 hrs to perform proton substitution, this was immersed in a largely excessive amount of pure water for 24 hrs to sufficiently wash the membrane, and whereby a polymer electrolyte membrane including a sulfonic acid group-containing polymer having the formula (G8) was obtained.

The sulfonic acid group-containing polymer having the formula (G8) contained 100 mol % of the constituent unit having the formula (S1), among constituent units containing a sulfonic acid group.

The resulting membrane had a thickness of 25 μm, and an ion exchange capacity obtained from neutralization titration of 3.3 meq/g. The membrane was a free standing membrane, and was a membrane which was transparent and uniform visually. The membrane had a proton conductivity of 380 mS/cm at 80° C. and a relative humidity of 85%, and had that of 0.8 mS/cm at 80° C. and a relative humidity of 25%, and it was excellent in low humidification proton conductivity.

Example 8

Sulfonic Acid Group-Containing Polymer Having Following Formula (G9)

[Chemical Formula 38]

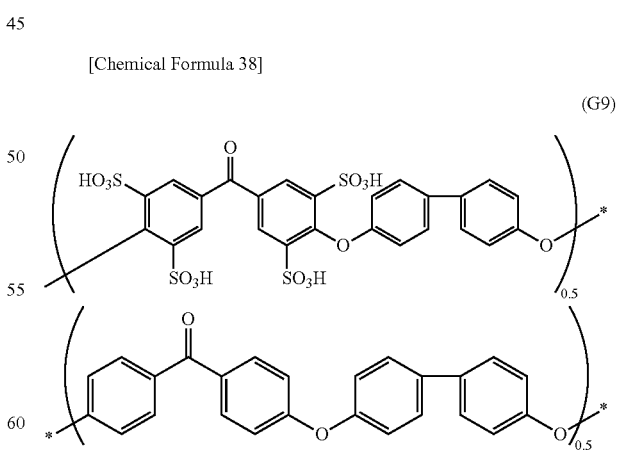

(G9)

According to the same method as that of Example 4 except that 3.7 g of 4,4'-biphenol was placed in place of the 2,2-bis(4-hydroxyphenyl)-1,3-dioxane mixture obtained in Synthesis Example 1, polymerization was performed to obtain a polymer containing a sodium sulfonate group. The polymer had a weight average molecular weight of 160000.

The resulting polymer was made into a membrane according to the same method as that of Example 4. Solubility of a sulfonic acid group-containing polymer before molding was good. After the membrane was immersed in a 10 wt % aqueous sulfuric acid solution at 25° C. for 24 hrs to perform proton substitution, this was immersed in a largely excessive amount of pure water for 24 hrs to sufficiently wash the membrane, and whereby a polymer electrolyte membrane including a sulfonic acid group-containing polymer having the formula (G9) was obtained.

The sulfonic acid group-containing polymer having the formula (G9) contained 100 mol % of the constituent unit having the formula (51), among constituent units containing a sulfonic acid group.

The resulting membrane had a thickness of 25 μm, and an ion exchange capacity obtained from neutralization titration of 3.3 meq/g. The membrane was a free standing membrane, and was a membrane which was transparent and uniform visually. The membrane had a proton conductivity of 370 mS/cm at 80° C. and a relative humidity of 85%, and had that of 0.7 mS/cm at 80° C. and a relative humidity of 25%, and it was excellent in low humidification proton conductivity.

Example 9

Sulfonic Acid Group-Containing Polymer Having Following Formula (G10)

[Chemical Formula 39]

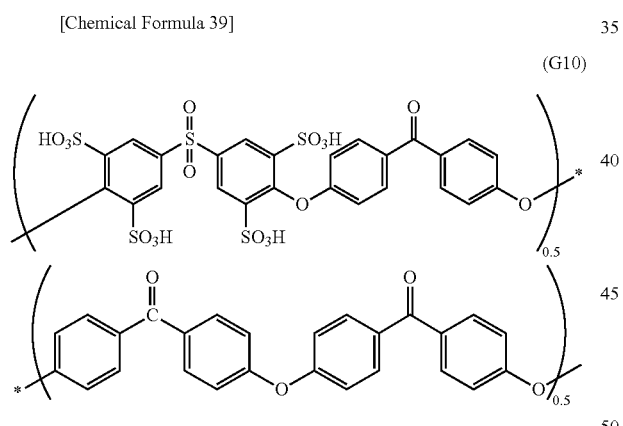

(G10)

According to the same method as that of Example 4 except that 7.0 g of the sulfonic acid group-containing aromatic compound having the formula (G3), which was obtained in Example 2, was placed in place of the sulfonic acid group-containing aromatic compound having the formula (G2), which was obtained in Example 1, polymerization was performed to obtain a precursor polymer having a ketal group. The precursor polymer had a weight average molecular weight of 200000.

The resulting precursor polymer was made into a membrane according to the same method as that of Example 4. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G10) was obtained.

The sulfonic acid group-containing polymer having the formula (G10) contained 100 mol % of the constituent unit having the formula (S1), among constituent units containing a sulfonic acid group.

The resulting membrane had a thickness of 25 μm, and an ion exchange capacity obtained from neutralization titration of 3.5 meq/g. Although weak in comparison with the membrane in Example 4, the membrane was a free standing membrane, and was a membrane which was transparent and uniform visually. The membrane had a proton conductivity of 360 mS/cm at 80° C. and a relative humidity of 85%, and had that of 0.65 mS/cm at 80° C. and a relative humidity of 25%, and it was excellent in low humidification proton conductivity.

Example 10

Sulfonic Acid Group-Containing Polymer Having Following Formula (G11)

[Chemical Formula 40]

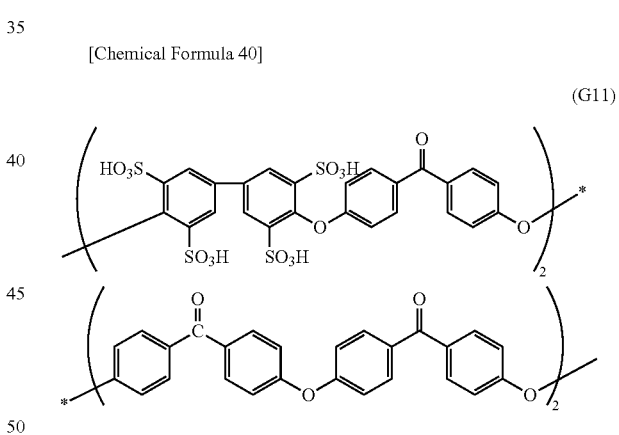

(G11)

According to the same method as that of Example 4 except that 6.0 g of the sulfonic acid group-containing aromatic compound having the formula (G4), which was obtained in Example 2, was placed in place of the sulfonic acid group-containing aromatic compound having the formula (G2), which was obtained in Example 1, polymerization was performed to obtain a precursor polymer having a ketal group. The precursor polymer had a weight average molecular weight of 190000.

The resulting precursor polymer was made into a membrane according to the same method as that of Example 4. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G11) was obtained.

The sulfonic acid group-containing polymer having the formula (G11) contained 100 mol % of the constituent unit having the formula (S1), among constituent units containing a sulfonic acid group.

The resulting membrane had a thickness of 25 μm, and an ion exchange capacity obtained from neutralization titration of 3.6 meq/g. Although weak in comparison with the membrane in Example 4, the membrane was a free standing membrane, and was a membrane which was transparent and uniform visually. The membrane had a proton conductivity of 350 mS/cm at 80° C. and a relative humidity of 85%, and had that of 0.6 mS/cm at 80° C. and a relative humidity of 25%, and it was excellent in low humidification proton conductivity.

g of potassium carbonate (Aldrich reagent, 8 mmol), and 20.0 g (2 mmol) of the oligomer a1 not containing a sulfonic acid group (terminal hydroxyl group), and replaced with nitrogen, and thereafter, dehydration was performed at 100° C. in 100 mL of N-methylpyrrolidone (NMP) and 30 mL of cyclohexane, thereafter, a temperature was raised to remove the cyclohexane, and 4.0 g of decafluorobiphenyl (Aldrich reagent, 12 mmol) was placed to perform a reaction at 105° C. for 1 hr. Purification was performed by re-precipitation with a large amount of isopropyl alcohol, to obtain an oligomer a1' not containing a sulfonic acid group having the following formula (G12) (terminal fluoro group). The oligomer had a number average molecular weight of 11000, and a number average molecular weight of the oligomer a1 not containing a sulfonic acid group was obtained as value 10400, the value being obtained by subtracting a linker site (molecular weight 630).

[Chemical Formula 41]

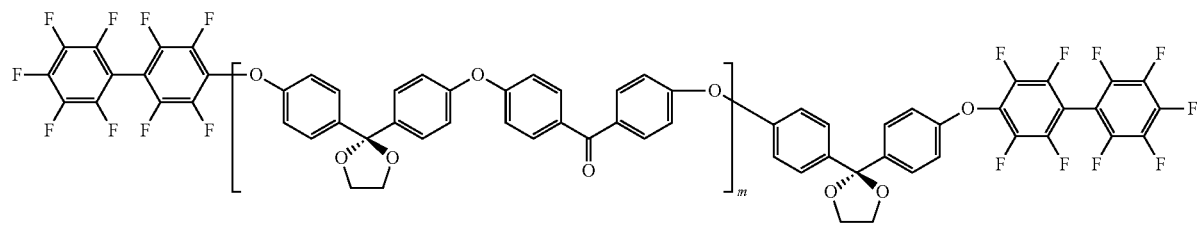

(G12)

Example 11

Synthesis of Oligomer a1' not Containing Sulfonic Acid Group Having Following Formula (G12)

A 1000 mL 3-neck flask equipped with a stirrer, a nitrogen introducing tube and a Dean-Stark trap was charged with 16.59 g of potassium carbonate (Aldrich reagent, 120 mmol), 25.8 g (100 mmol) of the K-DHBP obtained in Synthesis Example 1 and 20.3 g of 4,4'-difluorobenzophenone (Aldrich reagent, 93 mmol), and replaced with nitrogen, and thereafter, dehydration was performed at 160° C. in 300 mL of N-methylpyrrolidone (NMP) and 100 mL of toluene, thereafter, a temperature was raised to remove the toluene, and polymerization was performed at 180° C. for 1 hr. Purification was performed by re-precipitation with a large amount of methanol, to obtain an oligomer a1 not containing a sulfonic acid group (terminal hydroxyl group). The oligomer had a number average molecular weight of 10000.

A 500 mL 3-neck flask equipped with a stirrer, a nitrogen introducing tube and a Dean-Stark trap was charged with 1.1

Synthesis of Oligomer a2 Containing Sulfonic Acid Group Having Following Formula (G13)

A 1000 mL 3-neck flask equipped with a stirrer, a nitrogen introducing tube and a Dean-Stark trap was charged with 41.5 g of potassium carbonate (Aldrich reagent, 300 mmol), 12.9 g (50 mmol) of the K-DHBP obtained in Synthesis Example 1, 9.3 g of 4,4'-biphenol (Aldrich reagent, 50 mmol), 58.3 g (93 mmol) of the sulfonic acid group-containing aromatic compound obtained in Example 1, and 49.1 g of 18-crown-6 (Wako Pure Chemical Industries, Ltd. 186 mmol), and replaced with nitrogen, and thereafter, dehydration was performed at 170° C. in 400 mL of N-methylpyrrolidone (NMP) and 150 mL of toluene, thereafter, a temperature was raised to remove the toluene, and polymerization was performed at 220° C. for 1 hr. Purification was performed by re-precipitation with a large amount of isopropyl alcohol, to obtain an oligomer a2 containing a sulfonic acid group having the following formula (G13) (terminal hydroxyl group). The oligomer had a number average molecular weight of 16000.

[Chemical Formula 42]

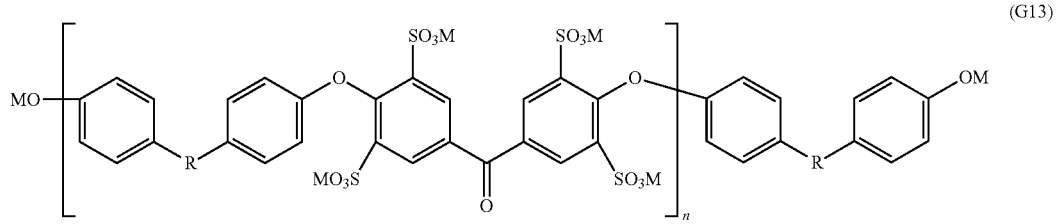

(G13)

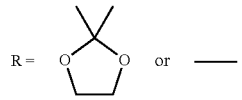 or ——

In the formula (G13), M is Na or K. Hereinafter, M indicates the same.

Synthesis of Block Copolymer b1 Containing Oligomer a2 as Segment Containing Sulfonic Acid Group (B1), Oligomer a1 as Segment not Containing Sulfonic Acid Group (B2), and Octafluorobiphenylene as Linker Site A 500 mL 3-neck flask equipped with a stirrer, a nitrogen introducing tube and a Dean-Stark trap was charged with 0.56 g of potassium carbonate (Aldrich reagent, 4 mmol), and 16 g (1 mmol) of the oligomer a2 containing a sulfonic acid group (terminal hydroxyl group), and replaced with nitrogen, and thereafter, dehydration was performed at 100° C. in 100 mL of N-methylpyrrolidone (NMP) and 30 mL of cyclohexane, thereafter, a temperature was raised to remove the cyclohexane, and 11 g (1 mmol) of the oligomer a1' not containing a sulfonic acid group (terminal fluoro group) was placed to perform a reaction at 105° C. for 24 hrs. Purification was performed by re-precipitation with a large amount of isopropyl alcohol, to obtain a block copolymer b1. The block copolymer had a weight average molecular weight of 230000.

A 25 wt % N-methylpyrrolidone (NMP) solution in which the resulting block polymer b1 had been dissolved was pressure-filtered using a glass fiber filter, and casting-coated on a glass substrate, and this was dried at 100° C. for 4 hrs, and heat-treated at 150° C. for 10 minutes under nitrogen to obtain a polyketal ketone membrane (thickness 25 μm). Solubility of a polymer was extremely good. After the membrane was immersed in a 10 wt % aqueous sulfuric acid solution at 95° C. for 24 hrs to perform proton substitution and a deprotection reaction, this was immersed in a largely excessive amount of pure water for 24 hrs to sufficiently wash the membrane, and whereby a polymer electrolyte membrane was obtained.

The membrane contained 100 mol % of the constituent unit having the formula (S1), among constituent units containing a sulfonic acid group. The membrane had an ion exchange capacity obtained from neutralization titration of 2.5 meq/g, and remaining of a ketal group was not recognized. The membrane was an extremely tough electrolyte membrane, and was a membrane which was transparent and uniform visually. The membrane had a proton conductivity of 900 mS/cm at 80° C. and a relative humidity of 85%, and had that of 50 mS/cm at 80° C. and a relative humidity of 25%, and it was excellent in low humidification proton conductivity. In addition, a dimensional change rate was small as 15%, and the membrane was also excellent in hot water resistance.

Further, in TEM observation, a cocontinuity-like phase-separated structure having a domain size of 25 nm could be confirmed. Both of a domain containing a sulfonic acid group and a domain not containing a sulfonic acid group formed a continuous phase.

Example 12

Synthesis of Oligomer a3' not Containing Sulfonic Acid Group Having the Formula (G6)

According to the method described in Example 11 except that a charging amount of 4,4'-difluorobenzophenone was changed to 20.7 g (Aldrich reagent, 95 mmol), an oligomer a3 not containing a sulfonic acid group (terminal hydroxyl group) was synthesized. The oligomer had a number average molecular weight of 15000.

According to the method described in Example 11 except that 30.0 g (2 mmol) of the oligomer a3 not containing a sulfonic acid group (terminal hydroxyl group) was charged in place of the oligomer a1 not containing a sulfonic acid group (terminal hydroxyl group), an oligomer a3' not containing a sulfonic acid group having the formula (G12) (terminal fluoro group) was synthesized. The oligomer had a number average molecular weight of 16000, and a number average molecular weight of the oligomer a3 not containing a sulfonic acid group was obtained as value 15400, the value being obtained by subtracting a linker site (molecular weight 630).

Synthesis of Oligomer a4 Containing a Sulfonic Acid Group Having the Formula (G13)

According to the method described in Example 11 except that a charging amount of the sulfonic acid group-containing aromatic compound obtained in Example 1 was changed to 59.5 g (95 mmol), and a charging amount of bisphenols was changed to 25.8 g (100 mmol) of K-DHBP, an oligomer a4 containing a sulfonic acid group having the formula (G13) (terminal hydroxyl group) was obtained. The oligomer had a number average molecular weight of 21000.

Synthesis of Block Copolymer b2 Containing Oligomer a4 as Segment Containing Sulfonic Acid Group (B1), Oligomer a3 as Segment not Containing Sulfonic Acid Group (B2), and Octafluorobiphenylene as Linker Site According to the method described in Example 11 except that 21 g (1 mmol) of the oligomer a4 containing a sulfonic acid group (terminal hydroxyl group) was placed in place of the oligomer a2 containing a sulfonic acid group (terminal hydroxyl group), and 16 g (1 mmol) of the oligomer a3' not containing a sulfonic acid group (terminal fluoro group) was placed in place of the oligomer a1' not containing a sulfonic acid group (terminal fluoro group), a block copolymer b2 was obtained. The block copolymer had a weight average molecular weight of 250000.

Using a 25 wt % N-methylpyrrolidone (NMP) solution in which the resulting block polymer b2 had been dissolved, a polymer electrode membrane was made by the method described in Example 11.

The membrane contained 100 mol % of the constituent unit having the formula (51), among constituent units containing a sulfonic acid group. The membrane had an ion exchange capacity obtained from neutralization titration of 2.2 meq/g, and remaining of a ketal group was not recognized. The membrane was an extremely tough electrolyte membrane, and was a membrane which was transparent and uniform visually. The membrane had a proton conductivity of 600 mS/cm at 80° C. and a relative humidity of 85%, and had that of 20 mS/cm at 80° C. and a relative humidity of 25%, and it was excellent in low humidification proton conductivity. In addition, a dimensional change rate was small as 10%, and the membrane was also excellent in hot water resistance.

Further, in TEM observation, a cocontinuity-like phase-separated structure having a domain size of 35 nm could be confirmed. Both of a domain containing a sulfonic acid group and a domain not containing a sulfonic acid group formed a continuous phase.

Example 13

Synthesis of Oligomer a5' not Containing Sulfonic Acid Group Having the Formula (G12)

According to the method described in Example 11 except that a charging amount of 4,4'-difluorobenzophenone was changed to 20.7 g (Aldrich reagent, 95 mmol), an oligomer a5 not containing a sulfonic acid group (terminal hydroxyl group) was synthesized. The oligomer had a number average molecular weight of 15000.

According to the method described in Example 11 except that 30.0 g (2 mmol) of the oligomer a5 not containing a sulfonic acid group (terminal hydroxyl group) was charged in place of the oligomer a1 not containing a sulfonic acid group (terminal hydroxyl group), an oligomer a5' not containing a sulfonic acid group having the formula (G12) (terminal fluoro group) was synthesized. The oligomer had a number average molecular weight of 16000, and a number average molecular weight of the oligomer a5 not containing a sulfonic acid group was obtained as value 15400, the value being obtained by subtracting a linker site (molecular weight 630).

Synthesis of Oligomer a6 Containing Sulfonic Acid Group

According to the method described in Example 11 except that a charging amount of the sulfonic acid group-containing aromatic compound obtained in Example 1 was changed to 30.0 g (47.5 mmol), 20.1 g (47.5 mmol) of the disodium 3,3'-disulfonate-4,4'-difluorobenzophenone having the formula (H1), which was obtained in Synthesis Example 2, was added, and a charging amount of bisphenols was changed to 25.8 g (100 mmol) of K-DHBP, an oligomer a6 containing a sulfonic acid group (terminal hydroxyl group) was obtained. The oligomer had a number average molecular weight of 20000.

Synthesis of Block Copolymer b3 Containing Oligomer a6 as Segment Containing Sulfonic Acid Group (B1), Oligomer a5 as Segment not Containing Sulfonic Acid Group (B2), and Octafluorobiphenylene as Linker Site According to the method described in Example 11 except that 20 g (1 mmol) of the oligomer a6 containing a sulfonic acid group (terminal hydroxyl group) was placed in place of the oligomer a2 containing a sulfonic acid group (terminal hydroxyl group), and 16 g (1 mmol) of the oligomer a5' not containing a sulfonic acid group (terminal fluoro group) was placed in place of the oligomer a1' not containing a sulfonic acid group (terminal fluoro group), a block copolymer b3 was obtained. The block copolymer had a weight average molecular weight of 320000.

Using a 25 wt % N-methylpyrrolidone (NMP) solution in which the resulting block polymer b3 had been dissolved, a polymer electrolyte membrane was made by the method described in Example 11.

The membrane contained 50 mol % of the constituent unit having the formula (S1), among constituent units containing a sulfonic acid group. The membrane had an ion exchange capacity obtained from neutralization titration of 1.8 meq/g, and remaining of a ketal group was not recognized. The membrane was an extremely tough electrolyte membrane, and was a membrane which was transparent and uniform visually. The membrane had a proton conductivity of 450 mS/cm at 80° C. and a relative humidity of 85%, and had that of 9 mS/cm at 80° C. and a relative humidity of 25%, and it was excellent in low humidification proton conductivity. In addition, a dimensional change rate was small as 7%, and the membrane was excellent in hot water resistance.

Further, in TEM observation, a cocontinuity-like phase-separated structure having a domain size of 30 nm could be confirmed. Both of a domain containing a sulfonic acid group and a domain not containing a sulfonic acid group formed a continuous phase.

Example 14

Synthesis of Oligomer a7' not Containing Sulfonic Acid Group Having the Formula (G12)

According to the method described in Example 11 except that a charging amount of 4,4'-difluorobenzophenone was changed to 20.7 g (Aldrich reagent, 95 mmol), an oligomer a5 not containing a sulfonic acid group (terminal hydroxyl group) was synthesized. The oligomer had a number average molecular weight of 15000.

According to the method described in Example 11 except that 30.0 g (2 mmol) of the oligomer a5 not containing a sulfonic acid group (terminal hydroxyl group) was charged in place of the oligomer a1 not containing a sulfonic acid group (terminal hydroxyl group), an oligomer a5' not containing a sulfonic acid group having the formula (G12) (terminal fluoro group) was synthesized. The oligomer had a number average molecular weight of 16000, and a number average molecular weight of the oligomer a5 not containing a sulfonic acid group was obtained as value 15400, the value being obtained by subtracting a linker site (molecular weight 630).

Synthesis of Oligomer a8 Containing Sulfonic Acid Group

According to the method described in Example 11 except that a charging amount of the sulfonic acid group-containing aromatic compound obtained in Example 1 was changed to 17.9 g (28.5 mmol), 28.1 g (66.5 mmol) of disodium 3,3'-disulfonate-4,4'-difluorobenzophenone having the formula (H1), which was obtained in Synthesis Example 2, was added, and a charging amount of bisphenols was changed to 25.8 g (100 mmol) of K-DHBP, an oligomer a6 containing a sulfonic acid group (terminal hydroxyl group) was obtained. The oligomer had a number average molecular weight of 19000.

Synthesis of Block Copolymer b4 Containing Oligomer a6 as Segment Containing Sulfonic Acid Group (B1), Oligomer a5 as Segment not Containing Sulfonic Acid Group (B2), and Octafluorobiphenylene as Linker Site According to the method described in Example 11 except that 19 g (1 mmol) of an oligomer a8 containing a sulfonic acid group (terminal hydroxyl group) was placed in place of the oligomer a2 containing a sulfonic acid group (terminal hydroxyl group), and 16 g (1 mmol) of an oligomer a7' not containing a sulfonic acid group (terminal fluoro group) was placed in place of the oligomer a1' not containing a sulfonic acid group (terminal fluoro group), a block copolymer b4 was obtained. The block copolymer had a weight average molecular weight of 360000.

Using a 25 wt % N-methylpyrrolidone (NMP) solution in which the resulting block polymer b4 had been dissolved, a polymer electrolyte membrane was made by the method described in Example 11.

The membrane contained 30 mol % of the constituent unit having the formula (S1), among constituent units containing a sulfonic acid group. The membrane had an ion exchange capacity obtained from neutralization titration of 1.7 meq/g, and remaining of a ketal group was not recognized. The membrane was an extremely tough electrolyte membrane, and was a membrane which was transparent and uniform visually. The membrane had a proton conductivity of 250 mS/cm at 80° C. and a relative humidity of 85%, and had that of 2 mS/cm at 80° C. and a relative humidity of 25%, and it was excellent in low humidification proton conductivity. In addition, a dimensional change rate was small as 6%, and the membrane was excellent in hot water resistance.

Further, in TEM observation, a cocontinuity-like phase-separated structure having a domain size of 25 nm could be confirmed. Both of a domain containing a sulfonic acid group and a domain not containing a sulfonic acid group formed a continuous phase.

Example 15

Synthesis of Oligomer a9' not Containing Sulfonic Acid Group Having Following Formula (G14)

According to the same method as that of Example 11 except that 26.7 g (93 mmol) of 4,4'-dichlorodiphenyl sulfone was placed in place of 4,4'-difluorobenzophenone, an oligomer a9' not containing a sulfonic acid group (terminal fluoro group) was obtained. The oligomer had a number average molecular weight of 11000, and a number average molecular weight of an oligomer a9 not containing a sulfonic acid group was obtained as value 10400, the value being obtained by subtracting a linker site (molecular weight 630).

Synthesis of Block Copolymer b5 Containing Oligomer a2 as Segment Containing Sulfonic Acid Group (B1), Oligomer a9 as Segment not Containing Sulfonic Acid Group (B2), and Octafluorobiphenylene as Linker Site According to the method described in Example 11 except that 11 g (1 mmol) of the oligomer a9' not containing a sulfonic acid group (terminal fluoro group) was placed in place of the oligomer a1' not containing a sulfonic acid group (terminal fluoro group), a block copolymer b5 was obtained. The block copolymer had a weight average molecular weight of 200000.

Using a 25 wt % N-methylpyrrolidone (NMP) solution in which the resulting block polymer b5 had been dissolved, a polymer electrolyte membrane was made by the method described in Example 11.

The membrane contained 100 mol % of the constituent unit having the formula (S1), among constituent units containing a sulfonic acid group. The membrane had an ion exchange capacity obtained from neutralization titration of 2.3 meq/g, and remaining of a ketal group was not recognized. The membrane was a free standing membrane, and was a membrane which was transparent and uniform visually. The membrane had a proton conductivity of 650 mS/cm at 80° C. and a relative humidity of 85%, and had that of 10 mS/cm at 80° C. and a relative humidity of 25%, and it was relatively excellent in low humidification proton conductivity. In addition, a dimensional change rate was greater as 30% in comparison with Example 11. Further, in TEM observation, a phase-separated structure having a domain size of 35 nm could be confirmed.

Example 16

Synthesis of Oligomer a10 Containing Sulfonic Acid Group Having Following Formula (G15)

According to the same method as that of Example 11 except that 64.7 g (93 mmol) of the sulfonic acid group-containing aromatic compound obtained in Example 2 was placed in place of the sulfonic acid group-containing aromatic compound obtained in Example 1, an oligomer a10 containing a sulfonic acid group having the following formula (G15) (terminal hydroxyl group) was obtained. The oligomer had a number average molecular weight of 16000.

[Chemical Formula 43]

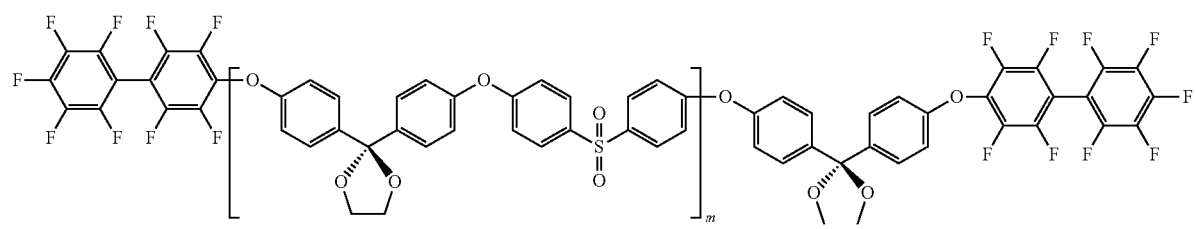

(G14)

[Chemical Formula 44]

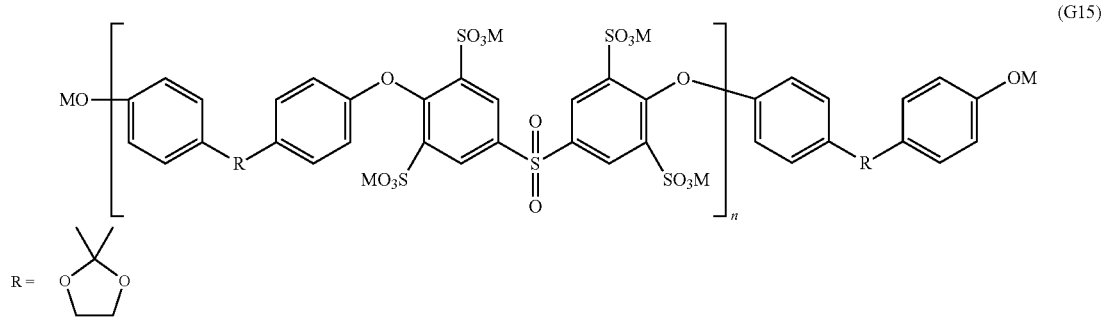

(G15)

Synthesis of Block Copolymer b6 Containing Oligomer a10 as Segment Containing Sulfonic Acid Group (B1), Oligomer a1 as Segment not Containing Sulfonic Acid Group (B2), and Octafluorobiphenylene as Linker Site According to the method described in Example 11 except that 16 g (1 mmol) of the oligomer a10 containing a sulfonic acid group (terminal hydroxyl group) was placed in place of an oligomer a12 containing a sulfonic acid group (terminal hydroxyl group), a block copolymer b6 was obtained. The block copolymer had a weight average molecular weight of 220000.

Using a 25 wt % N-methylpyrrolidone (NMP) solution in which the resulting block polymer b6 had been dissolved, a polymer electrolyte membrane was made by the method described in Example 11.

The membrane contained 100 mol % of the constituent unit having the formula (S1), among constituent units containing a sulfonic acid group. The membrane had an ion exchange capacity obtained from neutralization titration of 2.4 meq/g, and remaining of a ketal group was not recognized. The membrane was an extremely tough electrolyte membrane, and was a membrane which was transparent and uniform visually. The membrane had a proton conductivity of 700 mS/cm at 80° C. and a relative humidity of 85%, and had that of 15 mS/cm at 80° C. and a relative humidity of 25%, and it was excellent in low humidification proton conductivity. In addition, a dimensional change rate was relatively small as 20%, and the membrane was excellent in hot water resistance.

Further, in TEM observation, a cocontinuity-like phase-separated structure having a domain size of 30 nm could be confirmed. Both of a domain containing a sulfonic acid group and a domain not containing a sulfonic acid group formed a continuous phase.

Comparative Example 2

Using a commercially available Nafion (registered trademark) NRE211CS membrane (manufactured by Du Pont), various properties were evaluated. The membrane had an ion exchange capacity obtained from neutralization titration of 0.9 meq/g. The membrane was a membrane which was transparent and uniform visually, and a clear phase-separated structure was not confirmed in TEM observation. The membrane had a proton conductivity of 100 mS/cm at 80° C. and a relative humidity of 85%, and had that of 3 mS/cm at 80° C. and a relative humidity of 25%. When the membrane was immersed in hot water, it was vigorously swollen and handling was difficult, and when the membrane was grasped, it was broken in some cases.

Comparative Example 3

Synthesis of Polyether Ketone Oligomer c1 not Containing Sulfonic Acid Group and Ketal Group According to the method described in Example 5 except that 21.4 g (100 mmol) of DHBP was placed in place of 25.8 g (100 mmol) of K-DHBP, synthesis of a polyether ketone oligomer not containing a sulfonic acid group was tried. From a polymerization initial stage, an oligomer was precipitated, and polymerization was difficult. Since the oligomer was insoluble in a solvent, polymerization of a block polymer was difficult, and the oligomer could not be evaluated as an electrolyte membrane.

Comparative Example 4

By the method described in Journal of Polymer Science A Polymer Chemistry, 48, 2757, 2010, a polyether sulfone block copolymer was synthesized. That is, first, 4,4-dichlorodiphenyl sulfone was reacted in fuming sulfuric acid and, after completion of the reaction, salting out was performed using sodium chloride, to obtain 3,3'-sodium disulfonate-4,4'-dichlorodiphenyl sulfone (hereinafter, referred to as "SDCDPS"). Then, under the nitrogen atmosphere, a 1-neck eggplant flask equipped with a Dean-Stark tube was charged with 3.16 g (6.0 mmol) of the SDCDPS, 1.34 g (7.2 mmol) of 4,4'-biphenol, 1.49 g (10.8 mmol) of potassium carbonate, 23 ml of NMP, and 20 ml of toluene, and a temperature was kept at 150° C. for 2 hrs to azeotropically remove water in the system. Thereafter, the temperature was raised to 180° C. to perform a reaction for 16 hrs. After being allowed to cool, the reaction solution was poured into water, and potassium chloride was added thereto. The precipitate was recovered by filtration, and dried at 60° C. under reduced pressure to obtain a hydrophilic oligomer having OH groups on both ends.

Then, under the nitrogen atmosphere, a 1-neck eggplant flask equipped with a Dean-Stark tube was charged with 4.31 g (15.0 mmol) of 4,4'-dichlorodiphenyl sulfone, 3.05 g (16.4 mmol) of 4,4'-biphenol, 3.39 g (24.5 mmol) of potassium carbonate, 35 ml of NMP, and 20 ml of toluene, and a temperature was kept at 150° C. for 2 hrs to azeotropically remove water in the system. Thereafter, a temperature was raised to 180° C. to perform a reaction for 12 hrs. After being allowed to cool, the reaction solution was poured into water, and the resulting precipitate was filtered and, further, washed with methanol. The precipitate was dried at 100° C. under reduced pressure to obtain a hydrophobic oligomer having OH groups on both ends.

Under the nitrogen atmosphere, a 1-neck eggplant flask equipped with a 3-way cock was charged with 0.45 g of the hydrophilic oligomer, 0.20 g of the hydrophobic oligomer, and 5.5 ml of NMP, and the hydrophilic oligomer and the hydrophobic oligomer were dissolved at 80° C. After cooling with air, 0.02 g (0.06 mmol) of decafluorobiphenyl and 0.01 g (0.07 mmol) of potassium carbonate were added to perform a reaction at 120° C. for 18 hrs. After being allowed to cool, the reaction solution was diluted with NMP, and poured into isopropanol, and the resulting precipitate was filtered and washed with water. Then, the resulting polymer was treated with an acid. After the resulting polymer was stirred in a 1.0 M aqueous sulfuric acid solution at room temperature for 2 days, the polymer was recovered by filtration. The polymer was washed well with pure water, and dried at 60° C. for 10 hrs to obtain a pale brown polymer. The polymer had a weight average molecular weight of 150000, and it was difficult to have a high molecular weight.

Further, the resulting polymer was reacted in concentrated sulfuric acid at 45° C. for 6 hrs, and then a biphenyl unit was sulfonated, and washed well with pure water.

The membrane had an ion exchange capacity obtained from neutralization titration of 2.7 meq/g. It was a hard and brittle electrolyte membrane, and was a membrane which was opaque and ununiform visually. The membrane had a proton conductivity of 200 mS/cm at 80° C. and a relative humidity of 85%, and had that of 0.1 mS/cm at 80° C. and a relative humidity of 25%, and it was inferior in low humidification proton conductivity in comparison with Example 1 to 4. In addition, a dimensional change rate L2/L1 was great as 150%, and the membrane was inferior in hot water resistance.

Comparative Example 5

Synthesis of Oligomer c2' not Containing Sulfonic Acid Group Having Following Formula (G16)

According to the method described in Example 11 except that 33.6 (100 mmol) of 2,2-bis(4-hydroxyphenyl)hexafluoropropane was added in place of 25.8 (100 mmol) of K-DHBP, an oligomer c2 not containing a sulfonic acid group (terminal hydroxyl group) was synthesized. The oligomer had a number average molecular weight of 13000.

According to the method described in Example 12 except that the oligomer c2 not containing a sulfonic acid group (terminal hydroxyl group) (2 mmol) was charged in place of the oligomer a1 not containing a sulfonic acid group (terminal hydroxyl group), an oligomer c2' not containing a sulfonic acid group having the following formula (G16) (terminal fluoro group) was synthesized. The oligomer had a number average molecular weight of 14000, and a number average molecular weight of the oligomer c2' not containing a sulfonic acid group was obtained as value 13400, the value being obtained by subtracting a linker site (molecular weight 630).

[Chemical Formula 45]

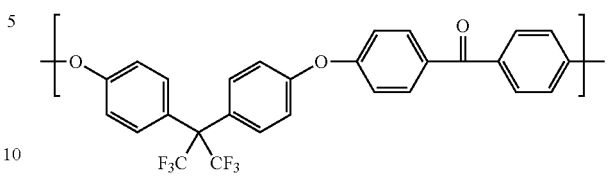

(G16)

Synthesis of Oligomer c3 Containing Sulfonic Acid Group Having Following Formula (G17)

According to the method described in Example 1 except that 33.6 (100 mmol) of 2,2-bis(4-hydroxyphenyl)hexafluoropropane was added in place of 12.9 g (50 mmol) of K-DHBP and 9.3 g of 4,4'-biphenol (Aldrich reagent, 50 mmol), an oligomer c3 containing a sulfonic acid group having the following formula (G17) (terminal hydroxyl group) was obtained. The oligomer had a number average molecular weight of 19000.

[Chemical Formula 46]

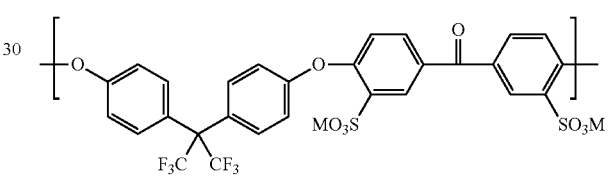

(G17)

Synthesis of Block Copolymer d1

According to the method described in Example 14 except that 19 g (1 mmol) of the oligomer c3 containing a sulfonic acid group (terminal hydroxyl group) was placed in place of the oligomer a2 containing a sulfonic acid group (terminal hydroxyl group), and 14 g (1 mmol) of the oligomer c2' not containing a sulfonic acid group (terminal fluoro group) was placed in place of the oligomer a1' not containing a sulfonic acid group (terminal fluoro group), a block copolymer d1 was obtained. The block copolymer had a weight average molecular weight of 160000.

Using a 25 wt % N-methylpyrrolidone (NMP) solution in which the resulting block polymer d1 had been dissolved, a polymer electrolyte membrane was made by the method described in Example 11.

The membrane contained 0 mol % of the constituent unit having the formula (S1), among constituent units containing a sulfonic acid group. The membrane had an ion exchange capacity obtained from neutralization titration of 2.3 meq/g. When the membrane was immersed in hot water, it was vigorously swollen and handling was difficult, and when the membrane was grasped, it was broken in some cases.

Comparative Example 6

Synthesis of Oligomer c4 Containing Sulfonic Acid Group

According to the method described in Example 11 except that a charging amount of the sulfonic acid group-containing aromatic compound obtained in Example 1 was changed to 8.93 g (14.25 mmol), 34.1 g (80.75 mol) of disodium 3,3'-disulfonate-4,4'-difluorobenzophenone having the formula (H1), which was obtained in Synthesis Example 2, was added, and a charging amount of bisphenols was changed to 25.8 g (100 mmol) of K-DHBP, an oligomer c4 containing a sulfonic acid group (terminal hydroxyl group) was obtained. The oligomer had a number average molecular weight of 19000.

Synthesis of Block Copolymer d2 Containing Oligomer c4 as Segment Containing Sulfonic Acid Group (B1), Oligomer a7 as Segment not Containing Sulfonic Acid Group (B2), and Octafluorobiphenylene as Linker Site According to the method described in Example 11 except that 19 g (1 mmol) of the oligomer c4 containing a sulfonic acid group (terminal hydroxyl group) was placed in place of the oligomer a2 containing a sulfonic acid group (terminal hydroxyl group), and 16 g (1 mmol) of an oligomer a7' not containing a sulfonic acid group (terminal fluoro group) was placed in place of the oligomer a1' not containing a sulfonic acid group (terminal fluoro group), a block copolymer d2 was obtained. The block copolymer had a weight average molecular weight of 180000.

Using a 25 wt % N-methylpyrrolidone (NMP) solution in which the resulting block polymer d2 had been dissolved, a polymer electrolyte membrane was made by the method described in Example 11.

The membrane contained 15 mol % of the constituent unit having the formula (S1), among constituent units containing a sulfonic acid group. The membrane had an ion exchange capacity obtained from neutralization titration of 1.5 meq/g, and remaining of a ketal group was not recognized. The membrane was an extremely tough electrode membrane, and was a membrane which was transparent and uniform visually. The membrane had a proton conductivity of 200 mS/cm at 80° C. and a relative humidity of 85%, and had that of 1 mS/cm at 80° C. and a relative humidity of 25%, and was inferior to Examples of the block copolymer. On the other hand, a dimensional change rate was small as 5%, and the membrane was excellent in hot water resistance.

Further, in TEM observation, a cocontinuity-like phase-separated structure having a domain size of 22 nm could be confirmed. Both of a domain containing a sulfonic acid group and a domain not containing a sulfonic acid group formed a continuous phase.

Raw Materials Used in the Examples:

4,4'-Difluorobenzophene purchased from Aladdin-reagent Co.:

[Chemical Formula 47]

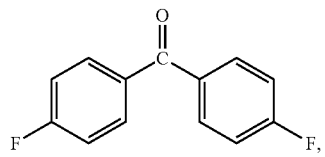

4,4'-Dichlorobenzophene purchased from Aladdin-reagent Co.:

[Chemical Formula 48]

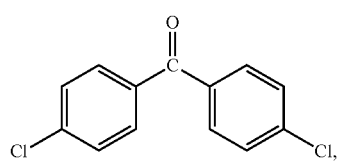

4,4'-Dibromobenzophene purchased from Aladdin-reagent Co.:

[Chemical Formula 49]

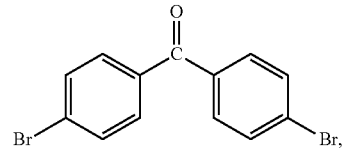

Sodium 5,5'-carbonylbis(2-fluorobenzenesulfonate) synthesized according to the method disclosed in CN101717354A:

[Chemical Formula 50]

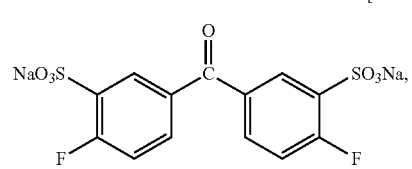

(e) Fuming sulfuric acid ($H_2SO_4/SO_3$): a fuming sulfuric acid solution with a sulfur trioxide concentration of 20% by weight was purchased from Sinopharm Chemical Reagent Co; a fuming sulfuric acid solution with a sulfur trioxide concentration of 50% by weight from Sinopharm Chemical Reagent Co; a fuming sulfuric acid solution with a sulfur trioxide concentration of 65% by weight from Aladdin-reagent Co.

(f) Organic solvents: dimethyl sulfoxide (DMSO), methanol, ethanol and acetone were purchased from Sinopharm Chemical Reagent Co.

(g) Base: sodium hydroxide, potassium hydroxide, sodium carbonate, potassium carbonate, sodium bicarbonate, potassium bicarbonate and ammonia water were purchased from Sinopharm Chemical Reagent Co.

The structures of sulfonated products obtained in the Examples and the Comparative Examples were analyzed and characterized by H-Nuclear magnetic resonance (NMR): ECX-400p JEOL, 400 MHZ, DMSO-$d_6$ as solvent.

Example 17

(1) 4,4'-Difluorobenzophenone (22.9 mmol) and fuming sulfuric acid with a sulfur trioxide concentration of 50% by weight containing 126.1 mmol $SO_3$ were placed in an autoclave, and reacted at 175° C. and under a pressure of 0.15 MPa for 16 hrs. After the reaction finished, the reaction mixture was poured into deionized water, and then neutralized with sodium hydroxide until the pH value thereof reached to 7.0, and then a crude product was obtained by vaporizing the mixture solution.

(2) The crude product obtained from the step (1) was entirely dissolved in DMSO and the undissolved matter was separated by centrifugation. The DMSO solution of reaction product was precipitated in ethanol, and filtered and dried at 120° C. in vacuum for 24 hrs, the resulting product was obtained.

Figure 2:
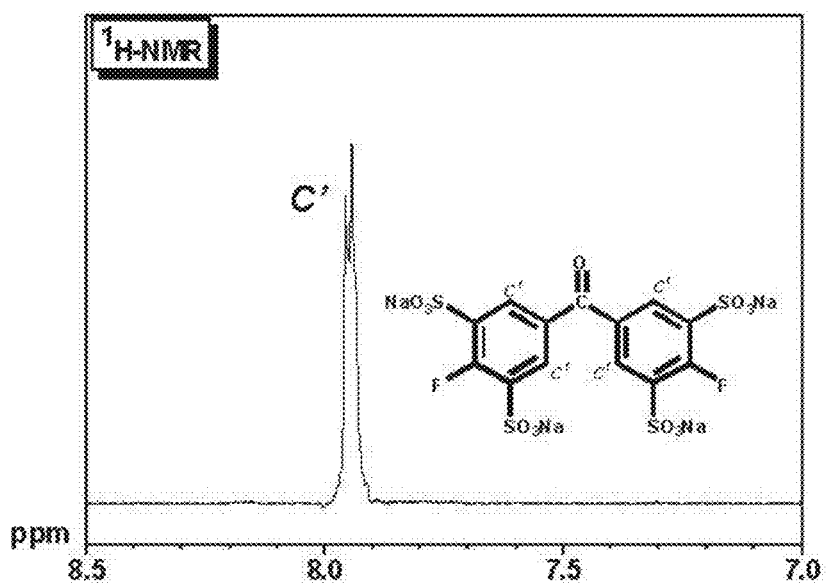
FIG. 2 shows the $^1$H-NMR spectrum of the reaction product of Example 17.

(3) The product obtained in the step (2) was recrystallized in a mixture of ethanol and deionized water (volume ratio of 2:1) and purified 4,4'-difluoro-3,3',5,5'-tetrasulfonate benzophenone-tetrasodium was obtained and its structure was determined by NMR (as shown in FIG. 2)

Example 18

(1) 4,4'-Dichlorobenzophene (25 mmol) and fuming sulfuric acid with a sulfur trioxide concentration of 65% by weight containing 150 mmol $SO_3$ were placed in an autoclave, and reacted at 200° C. and under a pressure of 0.9 MPa for 6 hrs. After the reaction finished, the reaction mixture was poured into deionized water, and then neutralized with sodium carbonate until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in methanol, and filtered and dried at 100° C. in vacuum for 72 hrs, the resulting product was obtained.

(3) The product obtained in the step (2) was recrystallized in a mixture of ethanol and deionized water (volume ratio of 3:1) and purified 4,4'-dichloro-3,3',5,5'-tetrasulfonate benzophenone-tetrasodium was obtained and its structure was determined by NMR.

Example 19

(1) 4,4'-4,4'-Dibromobenzophene (26.7 mmol) and fuming sulfuric acid with a sulfur trioxide concentration of 50% by weight containing 260 mmol $SO_3$ were placed in an autoclave, and reacted at 165° C. and under a pressure of 0.7 MPa for 22 hrs. After the reaction finished, the reaction mixture was poured into deionized water, and then neutralized with sodium bicarbonate, until the pH value thereof reached to 7.0, and then a crude product was obtained by vaporizing the mixture solution.

(2) The crude product obtained from the step (1) was entirely dissolved in DMSO and the dissolved matter was separated by centrifugation. The DMSO solution of the reaction product was precipitated in methanol, and filtered and dried at 110° C. in vacuum for 48 hrs, the resulting product was obtained.

(3) The product obtained in the step (2) was recrystallized in a mixture of ethanol and deionized water (volume ratio of 1:1) and purified 4,4'-dibromo-3,3',5,5'-tetrasulfonate benzophenone-tetrasodium was obtained and its structure was determined by NMR.

Example 20

(1) 4,4'-Difluorobenzophenone (22.9 mmol) and fuming sulfuric acid with a sulfur trioxide concentration of 50% by weight containing 190 mmol $SO_3$ were placed in an autoclave, and reacted at 200° C. and under a pressure of 1.6 MPa for 6 hrs. After the reaction finished, the reaction mixture was poured into deionized water, and then neutralized with potassium hydroxide until the pH value thereof reached to 7.4, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in acetone, and filtered and dried at 150° C. in vacuum for 6 hrs, the resulting product was obtained.

(3) The product obtained in the step (2) was recrystallized in a mixture of ethanol and deionized water (volume ratio of 2.7:1) and purified 4,4'-difluoro-3,3',5,5'-tetrasulfonate benzophenone-tetrapotassium was obtained and its structure was determined by NMR.

Example 21

(1) 4,4'-Difluorobenzophenone (45 mmol) and fuming sulfuric acid with a sulfur trioxide concentration of 50% by weight containing 495 mmol $SO_3$ were placed in an autoclave, and reacted at 200° C. and under a pressure of 2.4 MPa for 6 hrs. After the reaction finished, the reaction mixture was poured into deionized water, and then neutralized with potassium carbonate until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in methanol, and filtered and dried at 120° C. in vacuum for 36 hrs, the resulting product was obtained.

(3) The product obtained in the step (2) was recrystallized in a mixture of methanol and deionized water (volume ratio of 1:1) and purified 4,4'-difluoro-3,3',5,5'-tetrasulfonate benzophenone-tetrapotassium was obtained and its structure was determined by NMR.

Example 22

(1) 4,4'-Difluorobenzophenone (50 mmol) and fuming sulfuric acid with a sulfur trioxide concentration of 20% by weight containing 1500 mmol $SO_3$ were placed in an autoclave, and reacted at 150° C. and under a pressure of 2.9 MPa for 24 hrs. After the reaction finished, the reaction mixture was poured into deionized water, and then neutralized with potassium bicarbonate until the pH value thereof reached to 7.0, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in methanol, and filtered and dried at 120° C. in vacuum for 20 hrs, the resulting product was obtained.

Figure 3:
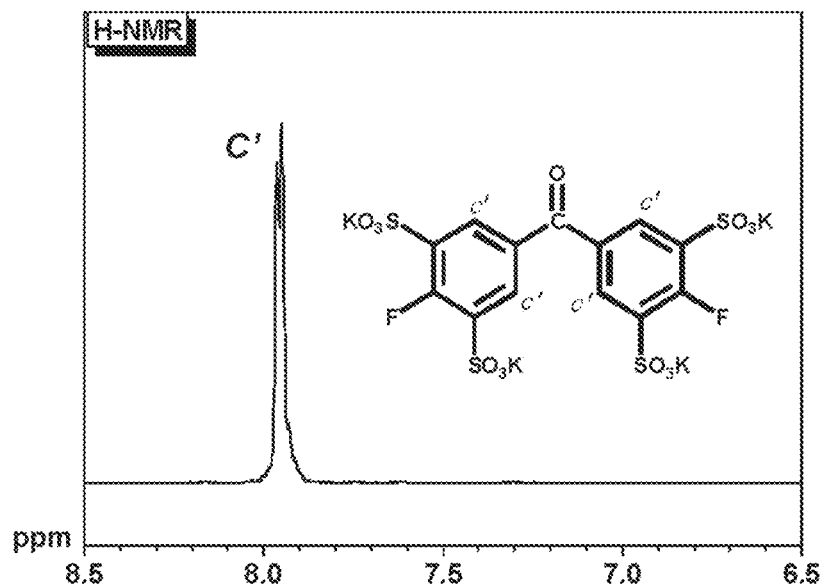
FIG. 3 shows the $^1$H-NMR spectrum of the reaction product of Example 22.

(3) The product obtained in the step (2) was recrystallized in a mixture of ethanol and deionized water (volume ratio of 3.2:1) and purified 4,4'-difluoro-3,3',5,5'-tetrasulfonate benzophenone-tetrapotassium was obtained and its structure was determined by NMR (as shown in FIG. 3).

Example 23

(1) 4,4'-Difluorobenzophenone (25 mmol) and fuming sulfuric acid with a sulfur trioxide concentration of 50% by weight containing 140 mmol $SO_3$ were placed in an autoclave, and reacted at 250° C. under a pressure of 2.0 MPa for 1 hr. After the reaction finished, the reaction mixture was poured into deionized water, and then neutralized with sodium hydroxide until the pH value thereof reached to 7.0, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in methanol, and filtered and dried at 120° C. in vacuum for 16 hrs, the resulting product was obtained.

(3) The product obtained in the step (2) was recrystallized in a mixture of ethanol and deionized water (volume ratio of 2.1:1) and purified 4,4'-difluoro-3,3',5,5'-tetrasulfonate benzophenone-tetrasodium was obtained and its structure was determined by NMR.

Example 24

(1) 4,4'-Difluorobenzophenone (25 mmol) and fuming sulfuric acid with sulfur trioxide concentration of 50% by weight containing 275 mmol SO₃ were placed in an autoclave, and reacted at 175° C. for 16 hrs and under a pressure of 0.4 MPa. After the reaction finished, the reaction mixture was poured into deionized water, and then neutralized with ammonia water until the pH value thereof reached to 7.3, and then a crude product was obtained by vaporizing the mixture solution.

(2) The crude product obtained from the step (1) was entirely dissolved in DMSO and the dissolved matters was separated by centrifugation. The DMSO solution of the reaction product was precipitated in acetone, and filtered and dried at 120° C. in vacuum for 24 hrs, the resulting product was obtained.

(3) The product obtained in the step (2) was recrystallized in a mixture of ethanol and deionized water (volume ratio of 2:1) and purified 4,4'-difluoro-3,3',5,5'-tetrasulfonate benzophenone-tetraammonium was obtained and its structure was determined by NMR.

Example 25

(1) Sodium 5,5'-carbonylbis(2-fluorobenzenesulfonate) (25 mmol) and fuming sulfuric acid with a sulfur trioxide concentration of 50% by weight containing 50 mmol SO₃ were placed in an autoclave, and reacted at 200° C. and under a pressure of 1.3 MPa for 12 hrs. After the reaction finished, the reaction mixture was poured into deionized water, and then neutralized with sodium hydroxide until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in acetone, and filtered and dried at 120° C. in vacuum for 24 hrs, the resulting product was obtained.

Figure 4:
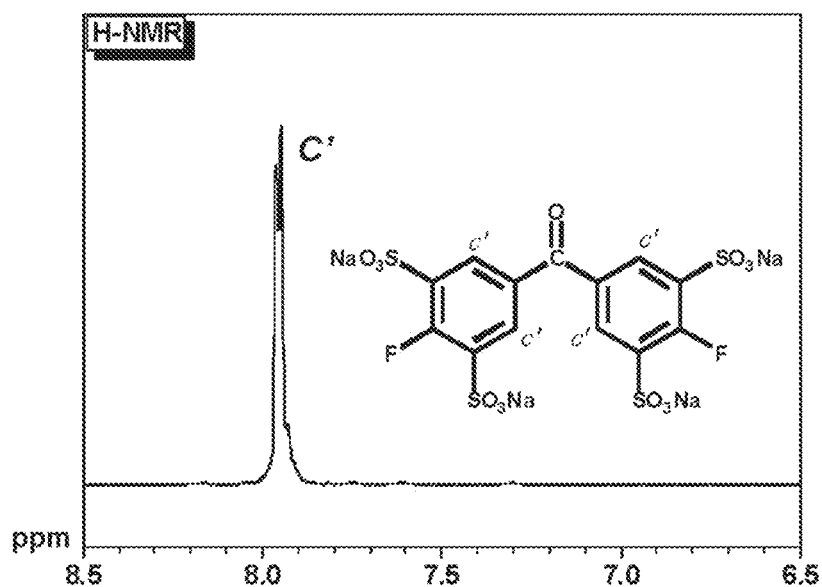
FIG. 4 shows the $^1$H-NMR spectrum of the reaction product of Example 25.

(3) The product obtained in the step (2) was recrystallized in deionized water, and purified 4,4'-difluoro-3,3',5,5'-tetrasulfonate benzophenone-tetrasodium was obtained and its structure was determined by NMR (as shown in FIG. 4).

Example 26

(1) 4,4'-Difluorobenzophenone (25 mmol) and fuming sulfuric acid with a sulfur trioxide concentration of 65% by weight containing 200 mmol SO₃ were placed in an autoclave, and reacted at 120° C. and under a pressure of 3.0 MPa for 48 hrs. After the reaction finished, the reaction mixture was poured into deionized water, and then neutralized with sodium hydroxide until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in acetone, and filtered and dried at 110° C. in vacuum for 20 hrs, the resulting product was obtained.

(3) The product obtained in the step (2) was recrystallized in deionized water and purified 4,4'-difluoro-3,3',5,5'-tetrasulfonate benzophenone-tetrasodium was obtained and its structure was determined by NMR.

Example 27

(1) 4,4'-Dichlorobenzophene (25 mmol) and fuming sulfuric acid with a sulfur trioxide concentration of 65% by weight containing 137.5 mmol SO₃ were placed in an autoclave, and reacted at 200° C. and under a pressure of 1.2 MPa for 6 hrs. After the reaction finished, the reaction mixture was poured into deionized water, and then neutralized with sodium carbonate until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in methanol, and filtered and dried at 100° C. in vacuum for 72 hrs, the resulting product was obtained.

(3) The product obtained in the step (2) was recrystallized in a mixture of ethanol and deionized water (volume ratio of 3:1) and purified 4,4'-dichloro-3,3',5,5'-tetrasulfonate benzophenone-tetrasodium was obtained and its structure was determined by NMR.

Comparative Example 7

(1) 4,4'-Difluorobenzophenone (25 mmol) and fuming sulfuric acid with a sulfur trioxide concentration of 50% by weight containing 800 mmol SO₃ were placed in a 3-neck flask, and reacted at 200° C. under a normal atmosphere for 6 hrs. After the reaction finished, the reaction mixture was poured into deionized water, and then neutralized with sodium hydroxide until the pH value thereof reached to 7.1, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in ethanol, and filtered and dried at 120° C. in vacuum for 12 hrs, the resulting product was obtained.

Figure 5:
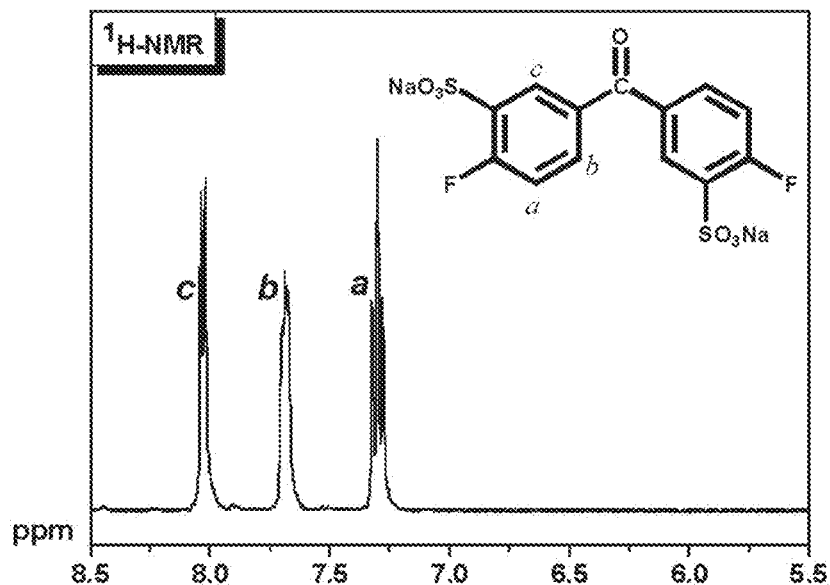
FIG. 5 shows the $^1$H-NMR spectrum of the reaction product of Comparative Example 7.

(3) The product obtained in the step (2) was recrystallized in a mixture of ethanol and deionized water (volume ratio of 2:1) and purified disodium 5,5'-carbonyl bis (2-fluorobenzenesulfonate) was obtained and its structure was determined by NMR (as shown in FIG. 5).

Comparative Example 8

(1) 4,4'-Difluorobenzophenone (25 mmol) and fuming sulfuric acid with a sulfur trioxide concentration of 50% by weight containing 200 mmol SO₃ were placed in an autoclave, and reacted at 260° C. and under a pressure of 0.5 MPa for 50 hrs. After the reaction finished, the reaction mixture was poured into deionized water, and then neutralized with sodium hydroxide until the pH value thereof reached to 7.4, and then a crude product was obtained by vaporizing the mixture solution.

(2) The crude product obtained from the step (1) was entirely dissolved in DMSO and the undissolved matter was separated by centrifugation. The DMSO solution of the reaction product was precipitated in ethanol, and filtered and dried at 120° C. in vacuum for 12 hrs, the resulting product was obtained.

Figure 6:
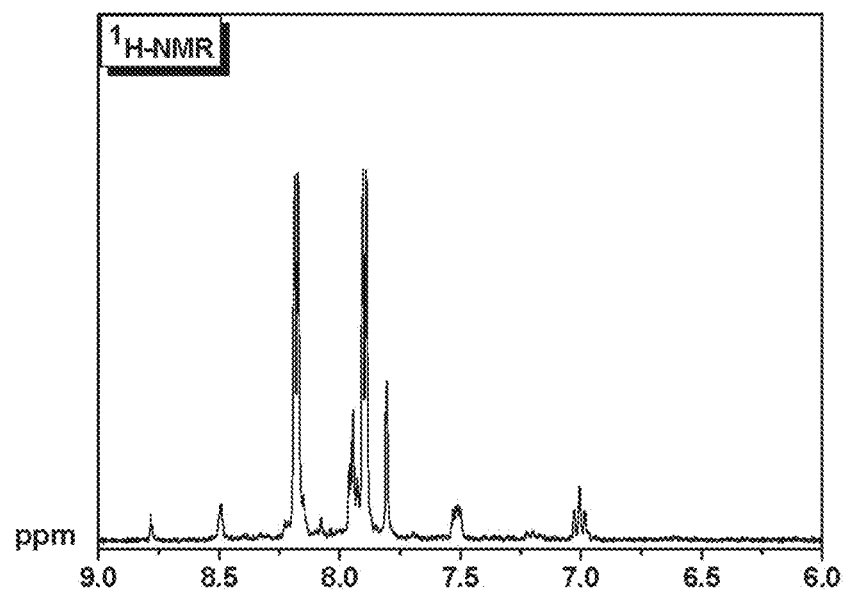
FIG. 6 shows the $^1$H-NMR spectrum of the reaction product of Comparative Example 8.

(3) The product obtained in the step (2) was recrystallized in a mixture of ethanol and deionized water (volume ratio of 2:1). No crystallization occurred, and the structure of the product obtained in the step (2) was characterized by NMR (as shown in FIG. 6). The result reveals that the product is not 4,4'-difluoro-3,3',5,5'-tetrasulfonate benzophenone-tetrasodium, and may be a decomposition product of an unknown structure.

Comparing the products obtained in the Examples 17-27 and the Comparative Examples 7-8, it can be seen that according to the invention, multi-substituted sulfonated aromatic compounds can be obtained by reacting an aromatic compound with fuming sulfuric acid having a sulfur trioxide concentration of 20% to 65% by weight at 120° C. to 250° C. in a closed system under an elevated pressure. Multi-substituted sulfonated aromatic compounds are important monomers necessary for preparing sulfonated poly(ether ether ketone)s (SPEEKs) with higher sulfonation degrees.

Example 28

Sulfonic Acid Group-Containing Polymer Having Formula (G6)

In a 500 mL 3-neck flask equipped with a stirrer, a nitrogen introducing tube and a Dean-Stark trap, using 3.9 g of potassium carbonate, 5.2 g of the 2,2-bis(4-hydroxyphenyl)-1,3-dioxane mixture obtained in Synthesis Example 1, 1.3 g of 4,4'-difluorobenzophenone, 8.8 g of the sulfonic acid group-containing aromatic compound having the formula (G2), which was obtained in Example 17, and 3.6 g of 18-crown-6-ether, dehydration was performed at 145° C. in 60 mL of dimethyl sulfoxide (DMSO)/40 mL of toluene, a temperature was raised to remove the toluene, and polymerization was performed at 160° C. for 14 hrs. Purification was performed by re-precipitation with a large amount of water, to obtain a precursor polymer having a ketal group. The polymer had a weight average molecular weight of 195000.

A 25 wt % N-methylpyrrolidone (NMP) solution in which the resulting precursor polymer had been dissolved was casting-coated on a glass substrate, and this was dried at 100° C. for 4 hrs, and heat-treated at 150° C. for 30 minutes under nitrogen to obtain a membrane. Solubility of a sulfonic acid group-containing polymer before molding was extremely good. After the membrane was immersed in a 10 wt % aqueous sulfuric acid solution at 25° C. for 24 hrs to perform proton substitution and a deprotection reaction, this was immersed in a largely excessive amount of pure water for 24 hrs to sufficiently wash the membrane, and whereby a polymer electrolyte membrane including a sulfonic acid group-containing polymer having the formula (G6) was obtained.

The sulfonic acid group-containing polymer having the formula (G6) contained 100 mol % of the constituent unit having the formula (S1), among constituent units containing a sulfonic acid group.

The resulting membrane had a thickness of 25 μm, and an ion exchange capacity obtained from neutralization titration of 4.2 meq/g, and remaining of a ketal group was not recognized. The membrane was a free standing membrane, and was a membrane which was transparent and uniform visually. The membrane had a proton conductivity of 700 mS/cm at 80° C. and a relative humidity of 85%, and had that of 1.5 mS/cm at 80° C. and a relative humidity of 25%, and it was excellent in low humidification proton conductivity.

Example 29

Synthesis of Oligomer a1' not Containing Sulfonic Acid Group Having Formula (G12)

According to the same method as that of Example 11 an oligomer a1' not containing a sulfonic acid group (terminal fluoro group) was obtained. The oligomer had a number average molecular weight of 11000, and a number average molecular weight of an oligomer a1 not containing a sulfonic acid group was obtained as value 10400, the value being obtained by subtracting a linker site (molecular weight 630).

Synthesis of Oligomer a2 Containing Sulfonic Acid Group Having Formula (G13)

A 1000 mL 3-neck flask equipped with a stirrer, a nitrogen introducing tube and a Dean-Stark trap was charged with 41.5 g of potassium carbonate (Aldrich reagent, 300 mmol), 12.9 g (50 mmol) of the K-DHBP obtained in Synthesis Example 1, 9.3 g of 4,4'-biphenol (Aldrich reagent, 50 mmol), 58.3 g (93 mmol) of the sulfonic acid group-containing aromatic compound obtained in Example 17, and 49.1 g of 18-crown-6 (Wako Pure Chemical Industries, Ltd. 186 mmol), and replaced with nitrogen, and thereafter, dehydration was performed at 140° C. in 180 mL of dimethyl sulfoxide (DMSO) and 90 mL of toluene, thereafter, a temperature was raised to remove the toluene, and polymerization was performed at 165° C. for 12 hr. Purification was performed by re-precipitation with a large amount of acetone to obtain an oligomer a2 containing a sulfonic acid group having the following formula (G13) (terminal hydroxyl group). The oligomer had a number average molecular weight of 15000.

Synthesis of Block Copolymer b1 Containing Oligomer a2 as Segment Containing Sulfonic Acid Group (B1), Oligomer a1 as Segment not Containing Sulfonic Acid Group (B2), and Octafluorobiphenylene as Linker Site According to the method described in Example 11 a block copolymer b1 was obtained. The block copolymer had a weight average molecular weight of 250000.

A 25 wt % N-methylpyrrolidone (NMP) solution in which the resulting block polymer b1 had been dissolved was pressure-filtered using a glass fiber filter, and casting-coated on a glass substrate, and this was dried at 100° C. for 4 hrs, and heat-treated at 150° C. for 10 minutes under nitrogen to obtain a polyketal ketone membrane (thickness 25 μm). Solubility of a polymer was extremely good. After the membrane was immersed in a 10 wt % aqueous sulfuric acid solution at 95° C. for 24 hrs to perform proton substitution and a deprotection reaction, this was immersed in a largely excessive amount of pure water for 24 hrs to sufficiently wash the membrane, and whereby a polymer electrolyte membrane was obtained.

The membrane contained 100 mol % of the constituent unit having the formula (S1), among constituent units containing a sulfonic acid group. The membrane had an ion exchange capacity obtained from neutralization titration of 2.5 meq/g, and remaining of a ketal group was not recognized. The membrane was an extremely tough electrolyte membrane, and was a membrane which was transparent and uniform visually. The membrane had a proton conductivity of 900 mS/cm at 80° C. and a relative humidity of 85%, and had that of 50 mS/cm at 80° C. and a relative humidity of 25%, and it was excellent in low humidification proton conductivity. In addition, a dimensional change rate was small as 15%, and the membrane was also excellent in hot water resistance.

Further, in TEM observation, a cocontinuity-like phase-separated structure having a domain size of 25 nm could be confirmed. Both of a domain containing a sulfonic acid group and a domain not containing a sulfonic acid group formed a continuous phase.

INDUSTRIAL APPLICABILITY

The polymer electrolyte material and polymer electrolyte membrane of the present invention can be applied to a variety of electrochemical apparatuses (e.g., a fuel cell, a water electrolysis apparatus, a chloroalkali electrolysis apparatus, etc.). Among these apparatuses, they are suitable for a fuel cell and, particularly, suitable for a fuel cell using hydrogen as a fuel.

Further, applications of the solid polymer fuel cell of the present invention are not particularly limited, and the solid polymer fuel cell is preferably used as a substitute for a previous primary cell or secondary cell such as an electric power supply source and a stationary electric power generator of potable devices including a potable phone, a personal computer, PDA, a video camera and a digital camera and the like; electric appliances including a cordless cleaner and the like; toys; and moving bodies including vehicles, for example, an electric bicycle, a motorcycle, an automobile, a bus, and a truck; ships and trains; or as a hybrid electric power supply with the previous primary cell or secondary cell.

DESCRIPTION OF THE REFERENCE NUMERALS AND SYMBOLS m1: Cocontinuous structure
m2: Lamella structure
m3: Cylinder structure
m4: Sea island structure

The invention claimed is:

1. A sulfonic acid group-containing polymer comprising a constituent unit containing a sulfonic acid group (A1), and a constituent unit not containing a sulfonic acid group (A2), wherein the constituent unit containing a sulfonic acid group (A1) contains one or more identical or different constituent units having formula (S1) at 25 mol % or more based on the total molar amount thereof:

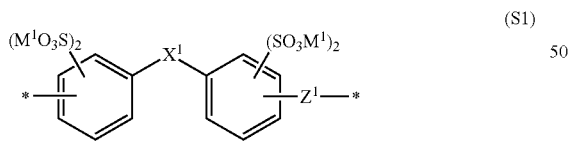
(S1)

wherein in the constituent units having the formula (S1), each $X^1$ is independently one of a ketone group, a sulfone group, —PO($R^1$)— (where $R^1$ is an organic group), —(CF$_2$)$_f$— (where f is an integer from 1 to 5) or —C(CF$_3$)$_2$—; and each $Z^1$ is independently O or S; each $M^1$ is independently hydrogen, a metal cation, an ammonium cation or a hydrocarbon group having 1 to 20 carbon atoms; and * is a bonding site with a moiety having the formula (S1) or other constituent units, wherein (S1) is a derivative of a compound having formula (M1), wherein a content of a compound having formula (M2) is 5% by weight or less

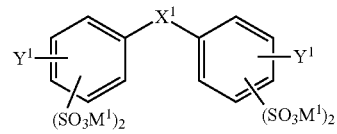
(M1)

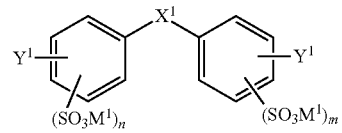
(M2)

wherein in the formulas (M1) and (M2), each $X^1$ is independently one of a ketone group, a sulfone group, —PO($R^1$)— (where $R^1$ is an organic group), —(CF$_2$)$_f$— (where f is an integer from 1 to 5) or —C(CF$_3$)$_2$—; each $Y^1$ is independently at least one of F, Cl, Br, and I; each $M^1$ is independently hydrogen, a metal cation, an ammonium cation or a hydrocarbon group having 1 to 20 carbon atoms; m is 0 or 1, n is 0 or 1.

2. The sulfonic acid group-containing polymer according to claim 1, wherein the polymer has one or more identical or different repeating structures having formula (S2):

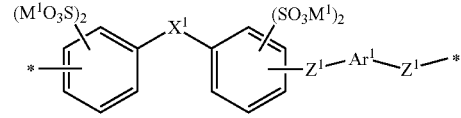
(S2)

wherein in the repeating structures having the formula (S2), each $X^1$ is independently one of a ketone group, a sulfone group, a direct linkage, —PO($R^1$)— (where $R^1$ is an organic group), —(CF$_2$)$_f$— (where f is an integer from 1 to 5) or —C(CF$_3$)$_2$—; and each $Z^1$ is independently O or S, each $M^1$ is independently hydrogen, a metal cation, an ammonium cation or a hydrocarbon group having 1 to 20 carbon atoms; each $Ar^1$ is independently a divalent group having formula (q1) or formula (q2); and * is a bonding site with a moiety having the formula (S2) or other repeating structures;

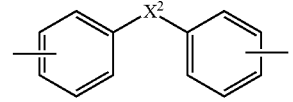
(q1)

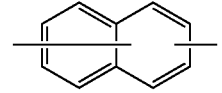
(q2)

wherein in the formula (q1), $X^2$ is one of a ketone group, a sulfone group, a direct linkage, —PO($R^1$)— (where $R^1$ is an organic group), —(CF$_2$)$_f$— (where f is an integer from 1 to 5) or —C(CF$_3$)$_2$; a group having formula (q1) or (q2) may be substituted.

3. The sulfonic acid group-containing polymer according to claim 2, wherein the repeating structures having the formula (S2) is a repeating structure having formula (S3):

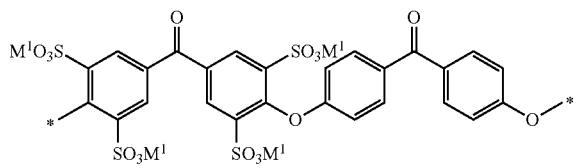

(S3)

wherein in the formula (S3), each $M^1$ is independently hydrogen, a metal cation, an ammonium cation or a hydrocarbon group having 1 to 20 carbon atoms, and * is a bonding site with a moiety having the formula (S3) or other repeating structures.

4. The sulfonic acid group-containing polymer according to claim 1, wherein in the formula (S1), the $X^1$ is a ketone group, the $Z^1$ is O, and all the sulfonic acid groups are in the meta-position of the $X^1$.

5. The sulfonic acid group-containing polymer according to claim 1, wherein the sulfonic acid group-containing polymer comprises a block copolymer containing one or more segments containing a sulfonic acid group (B1), and one or more segments not containing a sulfonic acid group (B2).

6. The sulfonic acid group-containing polymer according to claim 5, wherein the segments not containing a sulfonic acid group (B2) have a repeating structure having the formula (P1):

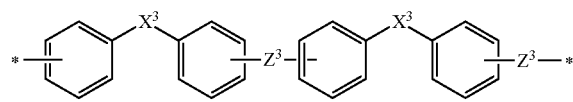

(P1)

wherein a site having the formula (P1) may be optionally substituted, but does not contain a sulfonic acid group, $X^3$ is an electron withdrawing group, $Z^3$ is an electron withdrawing group, O or S, and * is a bonding site with a moiety having the formula (P1) or other repeating structures.

7. The sulfonic acid group-containing polymer according to claim 6, wherein the repeating structure having formula (P1) is a repeating structure having formula (P2):

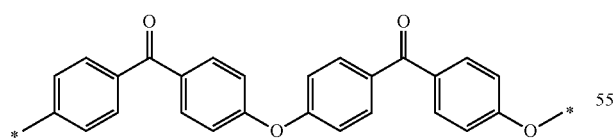

(P2)

wherein * is a bonding site with a moiety having the formula (P2) or other repeating structures.

8. The sulfonic acid group-containing polymer according claim 5, wherein the sulfonic acid group-containing polymer contains one or more linker sites linking the segments.

9. A polymer electrolyte material comprising the sulfonic acid group-containing polymer according to claim 1.

10. A polymer electrolyte molded product comprising the polymer electrolyte material according to claim 9.

11. A solid polymer fuel cell comprising the polymer electrolyte material according to claim 9.

12. A polymer electrolyte product comprising the polymer electrolyte material according to claim 9.

13. A composition comprising a sulfonic acid group-containing aromatic compound having formula (M1), wherein a content of an aromatic compound having formula (M2) is 5 wt % or less,

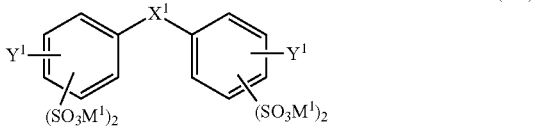

(M1)

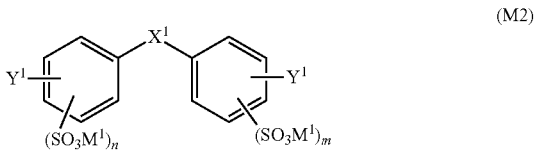

(M2)

wherein in the formulas (M1) and (M2), each $X^1$ is independently one of a ketone group, a sulfone group, —PO($R^1$)— (where $R^1$ is an organic group), —($CF_2$)$_f$— (where f is an integer from 1 to 5) or —C($CF_3$)$_2$—; and each $Y^1$ is independently at least one of F, Cl, Br, and I; each $M^1$ is independently hydrogen, a metal cation, an ammonium cation or a hydrocarbon group having 1 to 20 carbon atoms; m is 0 or 1, n is 0 or 1.

14. The sulfonic acid group-containing aromatic compound according to claim 13, wherein in the formula (M1), $X^1$ is a ketone group, $Y^1$ is F, and all the sulfonic acid groups are in the meta-position of the $X^1$ group.

15. A composition comprising a sulfonic acid group-containing aromatic compound having formula (M1), wherein a content of an aromatic compound having formula (M2) is 5 wt % or less,

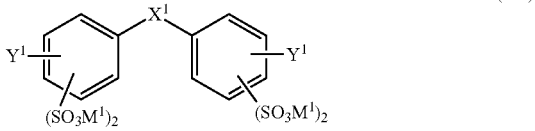

(M1)

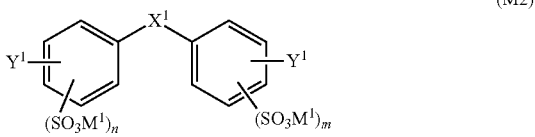

(M2)

wherein in the formulas (M1) and (M2), each $X^1$ is independently one of a ketone group, a sulfone group, —PO($R^1$)— (where $R^1$ is an organic group), —($CF_2$)$_f$— (where f is an integer from 1 to 5) or —C($CF_3$)$_2$—; and each $Y^1$ is independently at least one of F, Cl, Br, and I; each $M^1$ is independently hydrogen, a metal cation, an ammonium cation or a hydrocarbon group having 1 to 20 carbon atoms; m is 0 or 1, n is 0 or 1;

wherein the sulfonic acid group-containing aromatic compound having formula (M1) is made by a method of making a sulfonic group-containing aromatic compound, comprising reacting an aromatic compound having formula (M2) with fuming sulfuric acid, wherein the reaction is carried out at 120° C. to 250° C. in a closed system under an elevated pressure; and wherein the sulfonic group-containing aromatic compound has formula (M1) as shown below:

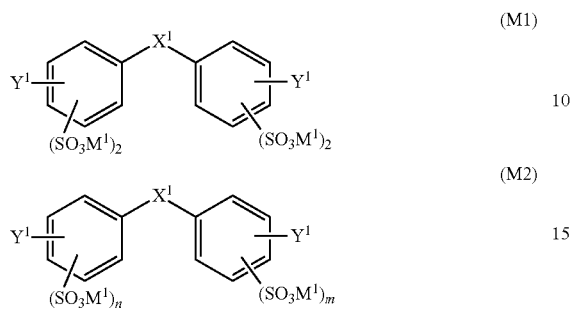

wherein in the formulas (M1) and (M2), each $X^1$ is independently one of a ketone group, a sulfone group, —PO($R^1$)— (where $R^1$ is an organic group), —(CF$_2$)$_f$— (where f is an integer from 1 to 5) or —C(CF$_3$)$_2$—; and each $Y^1$ is independently at least one of F, Cl, Br, and I; each $M^1$ is independently hydrogen, a metal cation, an ammonium cation or a hydrocarbon group having 1 to 20 carbon atoms; m is 0 or 1, n is 0 or 1.

* * * * *